US005942517A

United States Patent [19]
Nagarathnam et al.

[11] Patent Number: 5,942,517
[45] Date of Patent: Aug. 24, 1999

[54] 5-(HETEROCYCLIC ALKYL)-6-ARYL-DIHYDROPYRIMIDINES

[75] Inventors: Dhanapalan Nagarathnam, Ramsey; George Chiu, Bridgewater; T. G. Murali Dhar; Wai C. Wong, both of River Edge; Mohammad R. Marzabadi, Saddle Brook; Charles Gluchowski, Wayne, all of N.J.

[73] Assignee: Synaptic Pharmaceutical Corporation, Paramus, N.J.

[21] Appl. No.: 08/978,682

[22] Filed: Nov. 26, 1997

Related U.S. Application Data

[63] Continuation of application No. 08/340,611, Nov. 16, 1994, abandoned.

[51] Int. Cl.$^6$ ...................... A61K 31/505; C07D 239/32
[52] U.S. Cl. ................. 514/274; 514/258; 514/269; 544/230; 544/316; 544/330; 544/331; 544/332
[58] Field of Search ...................... 514/256, 269, 514/274; 544/316, 330, 331, 332, 230

[56] References Cited

U.S. PATENT DOCUMENTS

| 4,684,653 | 8/1987 | Taylor et al. | 514/258 |
|---|---|---|---|
| 4,845,216 | 7/1989 | Taylor et al. | 544/279 |
| 4,855,301 | 8/1989 | Atwal et al. | 514/269 |
| 4,882,334 | 11/1989 | Shih et al. | 514/258 |
| 4,902,796 | 2/1990 | Taylor et al. | 544/279 |
| 4,946,846 | 8/1990 | Nomura et al. | 514/258 |
| 5,202,330 | 4/1993 | Atwal et al. | 514/274 |

FOREIGN PATENT DOCUMENTS

| 0236902 | 9/1986 | European Pat. Off. . |
|---|---|---|
| 0234830 | 9/1987 | European Pat. Off. . |
| 0400665 | 12/1990 | European Pat. Off. . |
| 0459666 | 12/1991 | European Pat. Off. . |
| 0622366 | 11/1994 | European Pat. Off. . |
| 0622369 | 11/1994 | European Pat. Off. . |
| 0627427 | 12/1994 | European Pat. Off. . |
| 2610625 | 8/1988 | France . |
| 9200741 | 1/1992 | WIPO . |
| WO9214453 | 9/1992 | WIPO . |
| 9410989 | 5/1994 | WIPO . |
| 9422829 | 10/1994 | WIPO . |

OTHER PUBLICATIONS

Boer, R., et al., "(+)-Niguldipine binds with very high affinity to Ca$^{2+}$ channels and to a subtype of $\alpha_1$-adrenoceptors," *European Journal of Pharmacology—Molecular Pharmacology Section* (1989) 172: 131–145 (Exhibit 6).

Wetzel, J.M., et al., "Discovery of $\alpha_{1a}$-Adrenergic Receptor Antagonists Based on the L–Type Ca$^{2+}$ Channel Antagonist Niguldipine" *Journal of Medicinal Chemistry* (1995) 38(10): 1579–1581 (Exhibit 7).

Atwal, K.S. et al., "Dihydropyrimidine Calcium Channel Blockers. 2. 3–Substituted–4–aryl–1, 4–dihydro–6–methyl–5–pyrimidinecarboxylic Acid Esters as Potent Mimics of Dihydropyridines," Journal of Medicinal Chemistry (1990), vol. 33, pp. 2629–2635.

Atwal, K.S. et al., "Dihydropyrimidine Calcium Channel Blockers. 3. 3–Carbamoyl–4–aryl–1,2,3, 4–tetrahydro–6–methyl–5–pyrimidinecarboxylic Acid Esters as Orally Effective Antihypertensive Agents," Journal of Medicinal Chemistry (1991), vol. 34, pp. 806–811.

Atwal, K.S. et al., "Dihydropyrimidine Calcium Channel Blockers: 2–Heterosubstituted 4–Aryl–1, 4–dihydro–6–methyl–5–pyrimidinecarboxylic Acid Esters as Potent Mimics of Dihydropyridines" Journal of Medicinal Chemistry (1990), vol. 33, pp. 1510–1515.

Atwal, K.S. et al., "Substituted 1,4–Dihydropyrimidines. 3. Synthesis of Selectively Functionalized 2–Hetero–1,4–dihydropyrimidines," Journal of Organic Chemistry (1989), vol. 54, pp. 5898–5907.

Atwal, K.S. et al., "Synthesis of Substituted 1,2,3, 4–Tetrahydro–6–Methyl–2–Thioxo–5–Pyrimidinecarboxylic Acid Esters," (1987), vol. 26, pp. 1189–1192.

Cho, H. et al, "Dihydropyrimidines: Novel Calcium Antagonists with Potent and Long–Lasting Vasodilative and Antihypertensive Activity," Journal of Medicinal Chemistry (1989), vol. 32, pp. 2399–2406.

(List continued on next page.)

*Primary Examiner*—Yogendra N. Gupta
*Attorney, Agent, or Firm*—John P. White; Cooper & Dunham LLP

[57] ABSTRACT

This invention is directed to dihydropyrimidine compounds which are selective antagonists for human $\alpha_{1C}$ receptors and which have the structure:

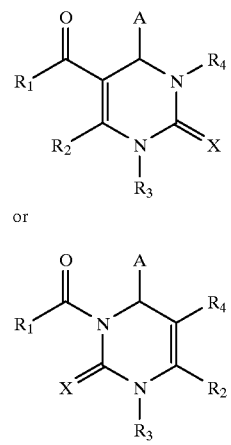

wherein A is aryl; $R_1$, $R_2$ and $R_3$ are alkyl or heteroalkyl; $R_4$ is heterocyclic alkyl; and X is S, O or $NR_3$. This invention also relates to use of these compounds for the treatment of benign prostatic hyperplasia and other diseases where antagonism of the human $\alpha_{1C}$ receptor is useful. The invention further provides pharmaceutical compositions comprising a therapeutically effective amount of such a compound and a pharmaceutically acceptable carrier.

29 Claims, No Drawings

OTHER PUBLICATIONS

D'Eletto, R.D. and Javitt, N.B. "Effect of Doxazosin on Cholesterol Synthesis In Cell Culture," Journal of Cardiovascular Pharmacology (1989), vol. 13, Supplement 2, pp. S1–S4.

McGrath, J.C. et al., "Alpha–Adrenoceptors: A Critical Review," Medicinal Research Reviews (1989), vol. 9, No. 4, pp. 407–533.

Rovnyak, G.C. et al., "Dihydropyrimidine Calcium Channel Blockers. 4. Basic 3–Substituted–4–aryl–1, 4–dihydropyrimidine–5–carboxylic Acid Esters. Potent Antihypertensive Gents," Journal of Medicinal Chemistry (1992), vol. 35, pp. 3254–3263.

Spiers, J.P. et al., "UK–52,046 (a Novel $\alpha_1$–Adrenoceptor Antagonist) and the Role of $\alpha$–Adrenoceptor Stimulation and Blockade on Atrioventricular Conduction," Journal of Cardiovascular Pharmacology (1990), vol. 16, pp. 824–830.

Triggle, D.J., "Dihydropyrimidine Calcium Channel Blockers. 2. 3–Substituted–4–aryl–1, 4–dihydro–6–methyl–5–pyrimidinecarboxylic Acid Esters as Potent Mimics of Dihydropyridines," Chemtracts—Organic Chemistry (Jan./Feb. 1991), pp. 68–72.

Zhan, G.–L. et al., "Bunazosin Reduces Intraocular Pressure By Increasing Uveoscleral Outflow In Rabbits," Investigative Ophthalmology and Visual Science (1993), vol. 34, Abst. No. 1133–49, p.928.

5-(HETEROCYCLIC ALKYL)-6-ARYL-DIHYDROPYRIMIDINES

This is a continuation division of application Ser. No. 08/340,611, filed Nov. 16, 1994.

BACKGROUND OF THE INVENTION

Throughout this application, various references are referred to within parentheses. Disclosures of these publications in their entireties are hereby incorporated by reference into this application to more fully describe the state of the art to which this invention pertains.

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., Urol. Clinics North Amer., 17, 651 (1990)). Over 400,000 prostatectomies are performed annually (data from 1986). A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

α-Adrenergic receptors (McGrath, et. al.Med. Res. Rev., 9, 407–533, 1989) are specific neuroreceptor proteins located in the peripheral and central nervous systems on tissues and organs throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (treatment of hypertension), naphazoline (nasal decongestant), and apraclonidine (treating glaucoma). α-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adrenergic receptors—$\alpha_1$ and $\alpha_2$—existed in the central and peripheral nervous systems. Since 1988, new techniques in molecular biology have led to the identification of at least six α-adrenergic receptors which exist throughout the central and peripheral nervous systems: $\alpha_{1A}$, $\alpha_{1B}$, $\alpha_{1C}$, $\alpha_{2A}$, $\alpha_{2B}$, and $\alpha_{2C}$ (Bylund, D. B., FASEB J., 6, 832 (1992)). In many cases, it is not known precisely which physiological responses in the body are controlled by each of these receptors. In addition, current α-adrenergic drugs are not selective for any particular α-adrenergic receptor. Many of these drugs produce untoward side effects which may be attributed to their poor α-adrenergic receptor selectivity.

Since the mid 1970's, nonselective α-antagonists have been prescribed to treat BPH. In 1976, M. Caine, et al. (Brit. J. Urol., 48, 255 (1976)), reported that the nonselective α-antagonist phenoxybenzamine was useful in relieving the symptoms of BPH. This drug may produce its effects by interacting with α-receptors located on the prostate. However, this drug also produces significant side effects such as dizziness and asthenia which severely limit its use in treating patients on a chronic basis. More recently, the α-adrenergic antagonists prazosin and terazosin have also been found to be useful for treating BPH. However, these drugs also produce untoward side effects. It has recently been discovered that the alc receptor is responsible for mediating the contraction of human prostate smooth muscle (Gluchowski, C. et. al., WO 94/10989, 1994; Forray, C. et. al., Mol. Pharmacol. 45, 703, 1994). This discovery indicates that the $\alpha_{1C}$ antagonists may be effective agents for the treatment of BPH with decreased side effects.

This invention is directed to dihydropyrimidine compounds which are selective antagonists for cloned human $\alpha_{1C}$ receptors. This invention is also related to uses of these compounds for lowering intraocular pressure (Zhan, et. al. Ophthalmol. Vis. Sci., 34 Abst. #1133, 928, 1993), inhibiting cholesterol synthesis (D'Eletto and Javitt, J. Cardiovascular Pharmacol., 13 (Suppl. 2) S1–S4, 1989), benign prostatic hyperplasia, impotency (Milne and Wyllie, EP 0 459 666 A2, 1991), sympathetically mediated pain (Campbell, WO 92/14453, 1992), cardiac arrhythmia (Spiers, et. al.,J. Cardiovascular Pharmacol., 16, 824–830, 1990) and for the treatment of any disease where antagonism of the $\alpha_{1C}$ receptor may be useful.

SUMMARY OF THE INVENTION

This invention is directed to dihydropyrimidine compounds which are selective antagonists for cloned human $\alpha_{1C}$ receptors. This invention is also related to uses of these compounds for lowering intraocular pressure, inhibiting cholesterol synthesis, the treatment of benign prostatic hyperplasia, impotency, cardiac arrhythmia and for the treatment of any disease where antagonism of the $\alpha_{1C}$ receptor may be useful. The invention further provides a pharmaceutical composition comprising a therapeutically effective amount of the above-defined compounds and a pharmaceutically acceptable carrier.

DETAILED DESCRIPTION OF THE INVENTION

The present invention is directed to compounds having the structures:

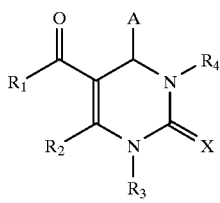

or

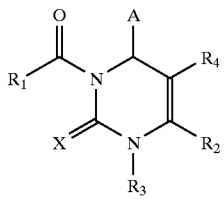

where A is

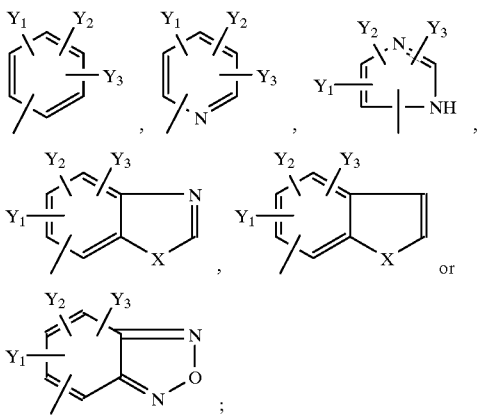

where each of $Y_1$, $Y_2$ and $Y_3$ is independently H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl; —F, —Cl, —Br, —I, —$NO_2$, —$N_3$, —CN —$OR_6$, —$OCOR_6$, —$COR_6$, —$CONHR_6$, —$CON(R_6)_2$, —$COOR_6$, —$CF_3$ or together constitute a methylenedioxy group;

where X is S, O or NH;

where $R_1$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl; —$NHR_6$, —$N(R_6)_2$ or —$OR_6$;

where $R_2$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl; $C_3$–$C_{10}$ cycloalkyl-$C_1$–$C_{10}$-alkyl, cycloalkyl-$C_1$–$C_{10}$-monofluoroalkyl or cycloalkyl-$C_1$–$C_{10}$-polyfluoroalkyl; —CN, —$CH_2XR_6$, —$CH_2X(CH_2)_nNHR_6$, —$(CH_2)_nNHR_6$, —$CH_2X(CH_2)_nN(R_6)_2$, —$CH_2X(CH_2)_nN_3$ or —$CH_2X(CH_2)_nNHCXR_7$;

where n is an integer from 0 to 5 and where X is as defined above;

where $R_3$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl;

where $R_4$ is

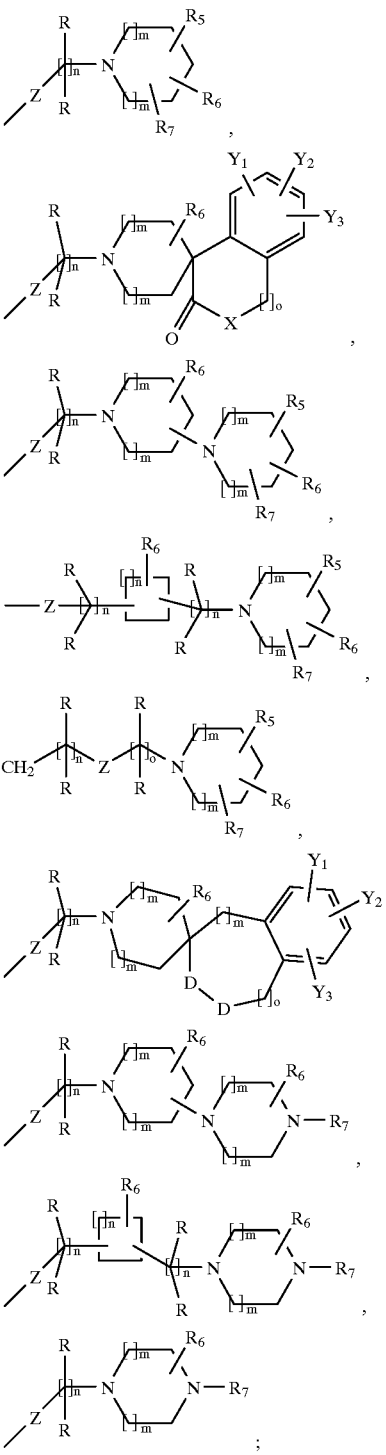

where each R is independently H; F; straight chained or branched $C_1$–$C_7$ alkyl, monofluoroalkyl or polyfluoroalkyl, $C_2$–$C_7$ alkenyl or alkynyl;

where $R_5$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl; phenyl, thiophenyl, pyridyl, pyrrolyl, furanyl, imidazolyl or indolyl; —COOR$_6$, —COR$_6$, —CONHR$_6$, —CN, —OH or —OR$_6$;

where each m is independently an integer from 0 to 3; where o is an integer from 1 to 3; where each n is independently an integer from 0 to 5;

where each R$_6$ is independently H; straight chained or branched C$_3$–C$_7$ alkyl, monofluoroalkyl or polyfluoroalkyl, C$_2$–C$_7$ alkenyl or alkynyl; C$_3$–C$_7$ cycloalkyl, monofluorocylcoalkyl, polyfluorocycloalkyl or cycloalkenyl;

where R$_7$ is phenyl, pyridyl, thiophenyl, furanyl, pyrazinyl, pyrrolyl, naphthyl, indolyl, imidazolyl, benzfurazanyl, benzfuranyl or benzyimidazolyl; C$_1$–C$_7$ alkyl, monofluoroalkyl or polyfluoroalkyl, C$_2$–C$_7$ alkenyl or alkynyl wherein the alkyl, monofluoroalkyl, polyfluoroalkyl, alkenyl or alkynyl is substituted with phenyl, pyridyl, thiophenyl, furanyl, pyrazinyl, pyrrolyl, naphthyl, indolyl, imidazolyl, benzfurazanyl, benzfuranyl or benzimidazolyl;

where each of Y$_1$, Y$_2$ and Y$_3$ is as defined above; where X is as defined above;

where Z is C$_2$ alkenyl or alkynyl, CH$_2$, O, CO, CO$_2$, CONR$_6$, S, SO, SO$_2$ or NR$_6$; and where each D is independently CH$_2$, O, S, NR$_6$, CO or CS; or a pharmaceutically acceptable salt thereof.

In a preferred embodiment, the compound may have the structures:

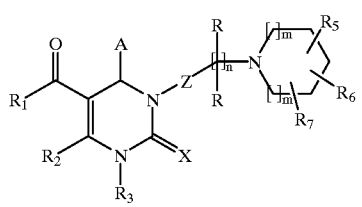

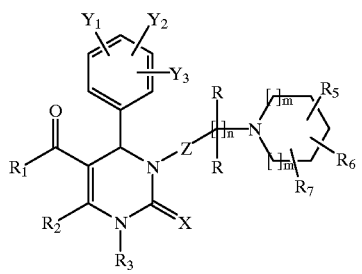

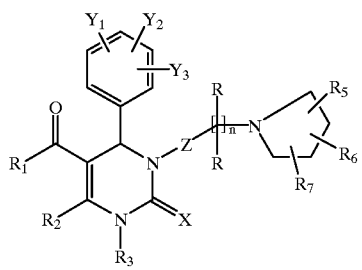

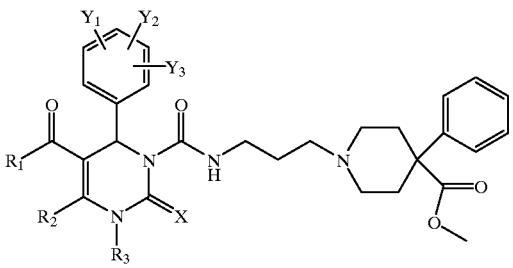

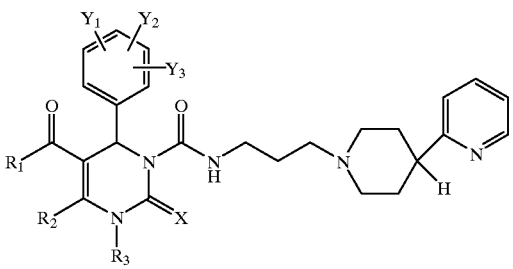

Where A, X, Z, Y$_1$, Y$_2$, Y$_3$, R, R$_1$, R$_2$, R$_3$, R$_5$, R$_6$, R$_7$, n and m are as defined above.

In preferred embodiments, the compounds may have the structures:

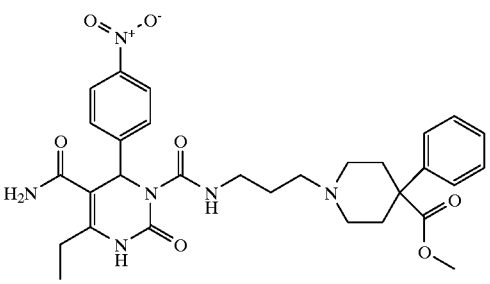

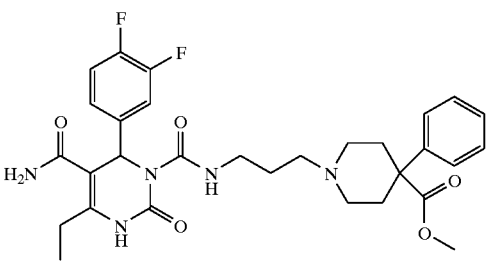

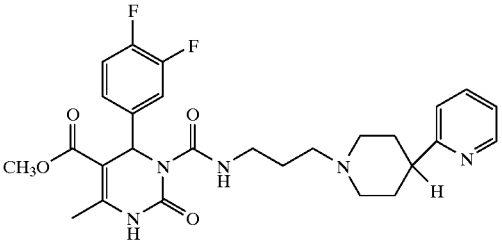

-continued

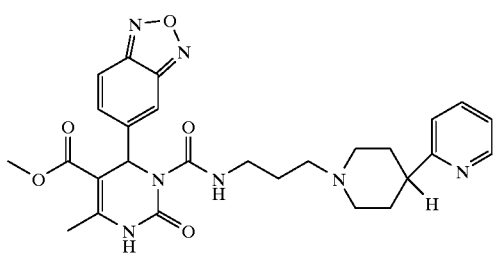

Other embodiments of the invention include compounds having the following structures:

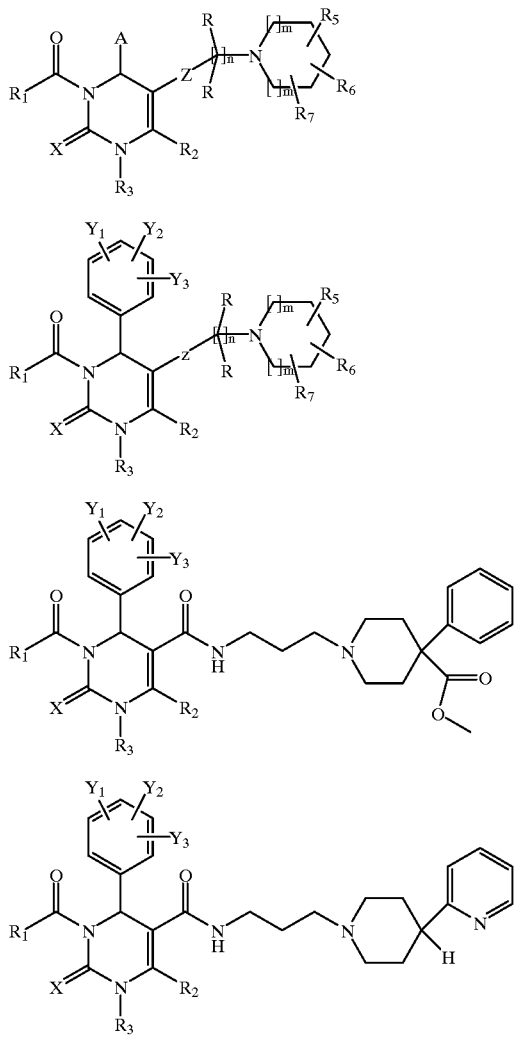

Where A, X, Z, $Y_1$, $Y_2$, $Y_3$, R, $R_1$, $R_2$, $R_3$, $R_5$, $R_6$, $R_7$, n and m are as defined above.

The invention also provides for compounds having the following structures:

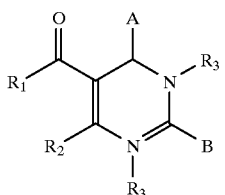

or

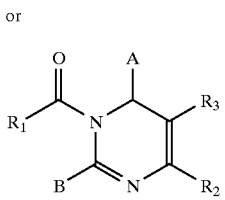

where A is

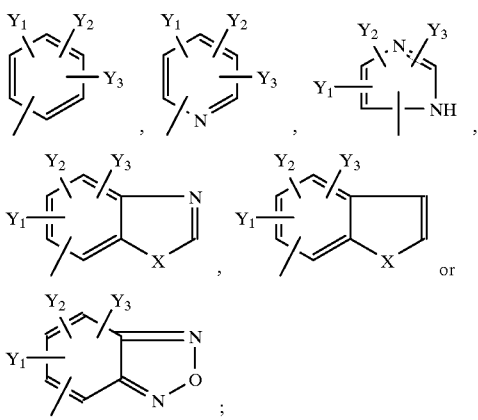

where each of $Y_1$, $Y_2$ and $Y_3$ is independently H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl; —F, —Cl, —Br, —I, —$NO_2$, —$N_3$, —CN, —$OR_4$, —$OCOR_4$, —$COR_4$, —$CONHR_4$, —$CON(R_4)_2$, —$COOR_4$, —$CF_3$ or together constitute a methylenedioxy group;

where X is S, O or NH;

where B is H; straight chained or branched $C_1$–$C_7$ alkyl, monofluoroalkyl, polyfluoroalkyl, alkoxy or thioalkyl, $C_2$–$C_7$ alkenyl, —$SCH_2C_6H_4OR_4$, —$(CH_2)_nC_6H_5$, —$CH_2X(CH_2)_nNHR_4$ or —$(CH_2)_nNHR_4$;

where n is an integer from 0 to 5;

where $R_1$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl; —$NHR_4$, —$N(R_4)_2$ or —$OR_4$;

where $R_2$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl; $C_3$–$C_{10}$ cycloalkyl-$C_1$–$C_{10}$-alkyl, $C_3$–$C_{10}$ cycloalkyl-$C_1$–$C_{10}$-monofluoroalkyl or cycloalkyl-$C_1$–$C_{10}$-polyfluoroalkyl; —CN, —$CH_2XR_4$, —$CH_2X(CH_2)_nNHR_4$, —$(CH_2)_nNHR_4$, —$CH_2X(CH_2)_nN(R_4)_2$, —$CH_2X(CH_2)_nN_3$ or —$CH_2X(CH_2)_nNHCXR_6$;

where $R_3$ is

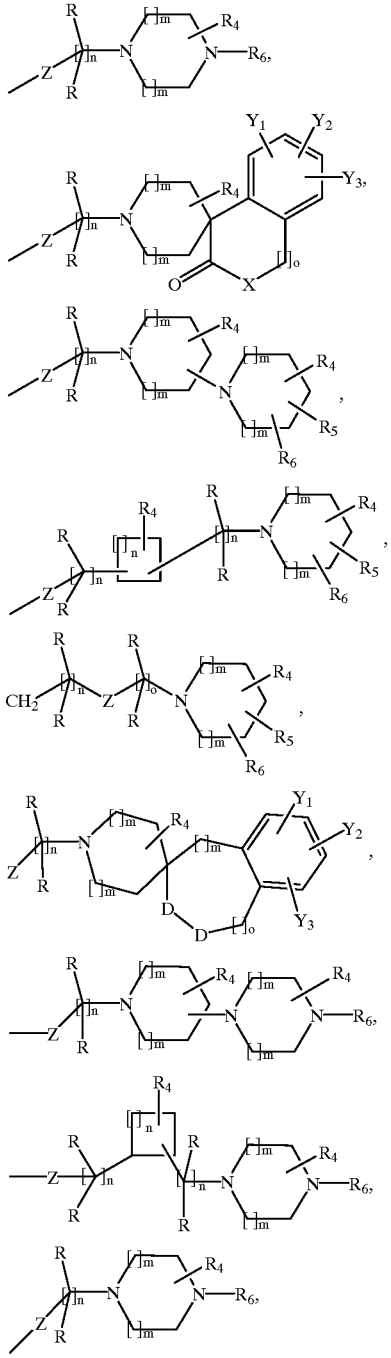

where each R is independently H; F; straight chained or branched $C_1$–$C_7$ alkyl, monofluoroalkyl or polyfluoroalkyl, $C_2$–$C_7$ alkenyl or alkynyl;

where each $R_4$ is independently H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl;

where $R_5$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocylcoalkyl, polyfluorocycloalkyl or cycloalkenyl; phenyl, thiophenyl, pyridyl, pyrrolyl, furanyl, imidazolyl or indolyl; —$COOR_4$, —$COR_4$, —$CONHR_4$, —CN, —OH or —$OR_4$;

where each m is independently an integer from 0 to 3;

where o is an integer from 0 to 5;

where each n is independently an integer from 0 to 5;

where $R_6$ is phenyl, pyridyl, thiophenyl, furanyl, pyrazinyl, pyrrolyl, naphthyl, indolyl, imidazolyl, benzfurazanyl, benzfuranyl or benzimidazolyl; $C_1$–$C_7$ alkyl, monofluoroalkyl or polyfluoroalkyl, $C_2$–$C_7$ alkenyl or alkynyl wherein the alkyl, monofluoroalkyl, polyfluoroalkyl, alkenyl or alkynyl is substituted with phenyl, pyridyl, thiophenyl, furanyl, pyrazinyl, pyrrolyl, naphthyl, indolyl, imidazolyl, benzfurazanyl, benzfuranyl or benzimidazolyl;

where each of $Y_1$, $Y_2$ and $Y_3$ is as defined above;

where Z is $C_2$ alkenyl or alkynyl, $CH_2$, O, CO, $CO_2$, $CONR_4$, S, SO, $SO_2$ or $NR_4$; and where each D is independently $CH_2$, O, S, $NR_4$, CO or CS; or a pharmaceutically acceptable salt thereof.

Other embodiments of the invention include the compounds having the following structures:

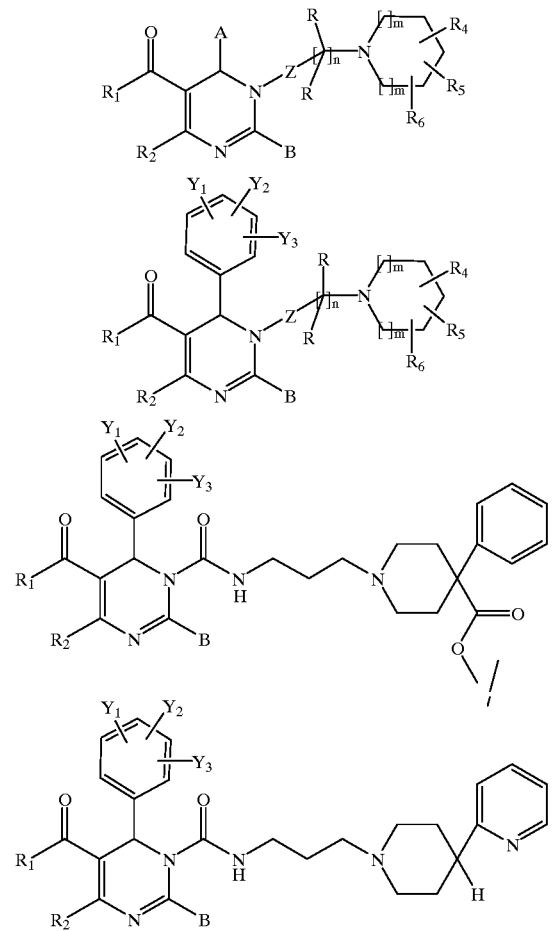

-continued

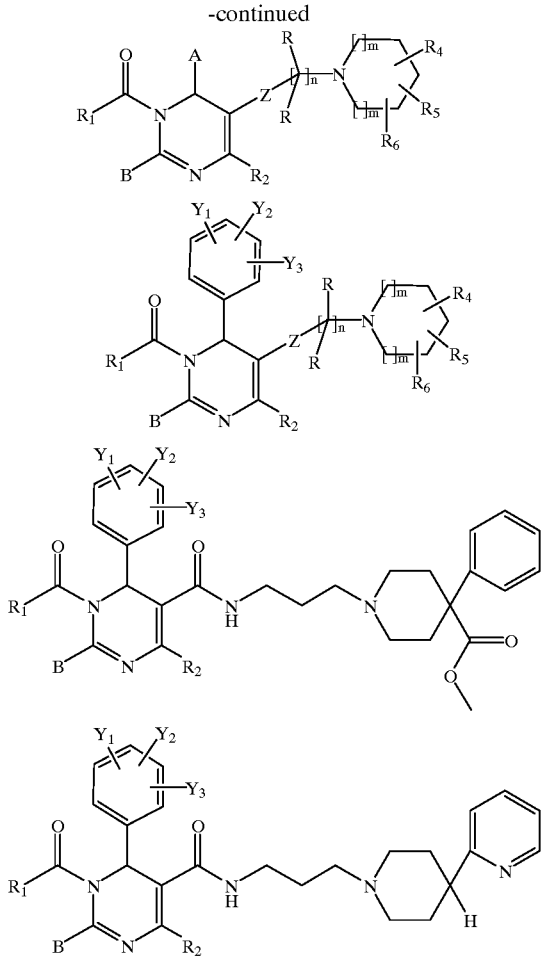

Where A, B, Z, $Y_1$, $Y_2$, $Y_3$, R, $R_1$, $R_2$, $R_4$, $R_5$, $R_6$, n and m are as defined above.

The invention provides for the preferred embodiment having the following structure.

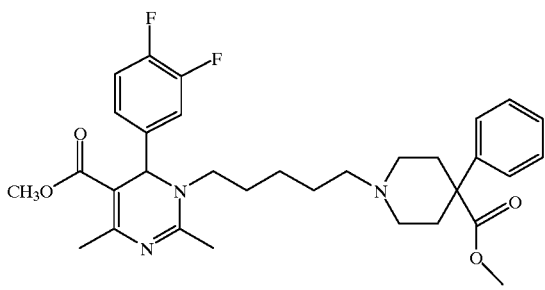

The invention also provides for the (−) and (+) enantiomers of all compounds of the subject application described herein. Included in this invention are pharmaceutically acceptable salts and complexes of all of the compounds described herein. The salts include but are not limited to the following acids and bases. The following inorganic acids; hydrochloric acid, hydrofluoric acid, hydrobromic acid, hydroiodic acid, sulfuric acid and boric acid. The organic acids; acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid and mandelic acid. The following inorganic bases; ammonia, hydroxyethylamine and hydrazine. The following organic bases; methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The invention also provides a pharmaceutical composition comprising a therapeutically effective amount of the compounds described above and a pharmaceutically acceptable carrier. In the subject invention a "therapeutically effective amount" is any amount of a compound which, when administered to a subject suffering from a disease against which the compounds are effective, causes reduction, remission, or regression of the disease. In one embodiment the therapeutically effective amount is an amount from about 0.01 mg per subject per day to about 500 mg per subject per day, preferably from about 0.1 mg per subject per day to about 60 mg per subject per day and most preferably from about 1 mg per subject per day to about 20 mg per subject per day. In the practice of this invention the "pharmaceutically acceptable carrier" is any physiological carrier known to those of ordinary skill in the art useful in formulating pharmaceutical compositions.

The invention also provides for pharmaceutical composition comprising a therapeutically effective amount of the any of the compounds described herein in combination with a therapeutically effective amount of finasteride and a pharmaceutically acceptable carrier. In one embodiment the pharmaceutical composition is a therapeutically effective amount from about 0.01 mg per subject per day to about 500 mg per subject per day of any one of the compounds described herein and a therapeutically effective amount of the finasteride of about 5 mg per subject per day. A more preferred embodiment of the pharmaceutical composition is a therapeutically effective amount from about 0.1 mg per subject per day to about 60 mg per subject per day of any one of the compounds described herein and a therapeutically effective amount of the finasteride of about 5 mg per subject per day. The most preferred embodiment of the pharmaceutical composition is a therapeutically effective amount from about 1 mg per subject per day to about 20 mg per subject per day of any one of the compounds described herein and a therapeutically effective amount of the finasteride of about 5 mg per subject per day.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

The invention further provides a method of treating a subject suffering from benign prostatic hyperplasia which comprises administering to the subject an amount of the one the compounds described above effective to treat benign prostatic hyperplasia.

The invention also provides a method of treating a subject suffering from high intraocular pressure which comprises administering to the subject an amount of any of the compounds described above effective to lower intraocular pressure.

This invention also provides a method of treating a subject suffering a disorder associated with high cholesterol which comprises administering to the subject an amount of any of the compounds described above effective to inhibit cholesterol synthesis.

This invention also provides a method of treating a disease which is susceptible to treatment by antagonism of the $\alpha_{1C}$ receptor which comprises administering to the subject an amount of any the compounds described above effective to treat the disease.

This invention also provides a method of treating a subject suffering from impotency which comprises administering to the subject an amount of any of the compounds described above effective to treat impotency.

This invention also provides a method of treating a subject suffering from sympathetically mediated pain which comprises administering to the subject an amount of any of the compounds described above effective to treat sympathetically mediated pain.

This invention also provides a method of treating a subject suffering from cardiac arrhythmia which comprises administering to the subject an amount of any of the compounds described above effective to treat cardiac arrhythmia.

This invention also provides a method of treating a subject suffering from benign prostatic hyperplasia which comprises administering to the subject an amount of any of the compounds described above in combination with a 5 alpha-reductase inhibitor effective to treat benign prostatic hyperplasia. The 5-alpha reductase inhibitor is finasteride. The dosage administered to the subject is about 0.01 mg per subject day to 50 mg per subject per day of finasteride in combination with an $\alpha_{1C}$ antagonist. A preferred dosage administered to the subject is about 0.2 mg per subject per day to 10 mg per subject per day of finasteride in combination with an $\alpha_{1C}$ antagonist. A more preferred dosage administered to the subject is about 1 mg per subject per day to 7 mg per subject per day of finasteride in combination with an $\alpha_{1C}$ antagonist. The most preferred dosage administered to the subject is about 5 mg per subject per day of finasteride in combination with an $\alpha_{1C}$ antagonist.

One skilled in the art will readily appreciate that appropriate biological assays will be used to determine the therapeutic potential of the claimed compounds for the treating the above noted disorders.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

For Examples 1–17 Scheme 1 describes the general synthetic preparation. All NMRs were obtained using a 300 MHz GE QEPLUS NMR machine.

EXAMPLE 1

1,6-Dihydro-5-methoxycarbonyl-2-[{(4-methoxyphenyl)methyl}thio]-4-methyl-6-(4-nitrophenyl)-1-{N-[3-(4,4-diphenylpiperidin-1-yl) propyl]}carboxamido pyrimidine.

a. 4,4-Diphenylpiperidine hydrochloride.

A mixture of 4-piperidone monohydrate hydrochloride (15.0 g, 0.0976 mol) and AlCl$_3$ (130 g, 0.976 mol, 10.0 eq)

in anhydrous benzene (600 mL) were stirred at reflux for 4 hours. The mixture was cooled to room temperature, poured into ice (300 g) and water (50 mL), and filtered. The solid was washed with toluene and dried to afford 19.2 g (72%) of an off-white solid, which was characterized spectroscopically.

b. 3-(4,4-Diphenylpiperidin-1-yl)propionitrile.

To a suspension of 4,4-diphenylpiperidine hydrochloride (0.195 g, 0.712 mmol) in EtOH (1.5 mL) was added $Et_3N$ (0.25 mL, 1.8 mmol, 2.6 eq) followed by acrylonitrile (0.13 mL, 2.01 mmol, 2.8 eq). The resulting solution was stirred at room temperature under argon for 15 min and then concentrated. Water was added, and the mixture was extracted with EtOAc (3×10 mL). The combined organic extracts were dried ($MgSO_4$) and concentrated to give 170 mg (87%) of a tan solid, which was characterized spectroscopically and used in the next reaction without purification.

c. 3-(4,4-Diphenylpiperidin-1-yl)propylamine.

To a stirred solution of 3-(4,4-diphenylpiperidin-1-yl)propionitrile (2.00 g, 6.89 mmol) in anhydrous THF (20 mL) under argon was added a solution of $BH_3$ in THF (1.0M, 24.1 mL, 24 mmol, 3.5 eq) at room temperature. The mixture was refluxed for 4.5 hours and then cooled to room temperature. Aqueous HCl (6N, 50 mL) was added and stirring was continued for 1 hour. The mixture was basified to pH 9 by addition of 6N aq. NaOH, extracted with $CH_2Cl_2$ (3×10 mL), dried ($MgSO_4$) and concentrated. The residue was purified by flash chromatography ($SiO_2$, EtOAc-MeOH-isopropylamine 9:1:0 to 4:1:0.2) to give 1.35 g (66%) of tan solid, which was characterized spectroscopically.

d. 2-(4-Methoxybenzyl)-2-thiopseudourea hydrochloride.

To a well-stirred suspension of thiourea (7.6 g, 0.1 mol) in THF (50 mL) at 0° C., 4-methoxybenzyl chloride (16 g, 0.1 mol) was added in 10 min and the mixture was allowed to warm to room temperature. After 2 hours the mixture was heated to 65° C. and kept at that temperature for 5 hours. It was cooled to room temperature and diluted with diethyl ether (200 mL). The white precipitate formed was filtered and dried (22.5 g, 96%); m. p. 161–163° C.

e. Methyl 2-{(4-nitrophenyl)methylene}-3-oxobutyrate.

A mixture of 4-nitrobenzaldehyde (15.1 g, 0.1 mol), methyl acetoacetate (12.773 g, 0.11 mol), piperidine (0.41 g, 476 mL, 4.8 mmol), and acetic acid (0.288 g, 274 mL, 4.8 mmol) in 2-propanol (400 mL) was stirred at room temperature for 48 hours. The white solid, methyl 2-{(4-nitrophenyl)methylene}-3-oxobutyrate, formed was filtered, washed with 2-propanol (2×50 mL) and dried (21.80 g, 93%).

f. 1,6-Dihydro-5-methoxycarbonyl-2-[{(4-methoxyphenyl)methyl}thio]-4-methyl-6-(4-nitrophenyl)pyrimidine.

A mixture of methyl 2-{(4-nitrophenyl)methylene}-3-oxobutyrate (8.96 g, 0.04 mol), 2-(4-methoxybenzyl)-2-thiopseudourea hydrochloride (9.28 g, 0.04 mol), and NaOAc (3.28 g, 0.04 mol) in DMF (100 mL) was stirred and heated at 70–75° C. for 4.5 hours. The mixture was cooled, poured into ice-water (300 mL), extracted with EtOAc (2×400 mL). The combined EtOAc extracts were washed with 10% $NaHCO_3$ solution (2×60 mL), brine (100 mL), and dried ($MgSO_4$). Solvent was evaporated and the crude product was purified by flash column chromatography on silica gel using 10% through 30% EtOAc in hexane as the gradient eluent, to leave the product as an oil, which on trituration with EtOAc/hexane became a yellow solid (11.4 g, 66.7%); m.p. 138–139° C.; $^1$H-NMR ($CDCl_3$): δ 2.15 (s, 3 H), 3.62 (s, 3 H), 3.72 (s, 3 H), 4.05, 5.78 (s, d, J=3 Hz, 1 H), 4.08, 4.20 (AB q, J=12.5 Hz, 2 H), 4.21, 6.40 (s, d, J=3 Hz, 1 H), 6.66 (2 d, J=8.5 Hz, 2 H), 7.08 (2 d, J=8.5 Hz, 2 H), 7.37 (2 d, J=8.8 Hz, 2 H), 8.7 (2 d, J=8.8 Hz, 2 H); Anal. Calcd. for $C_{21}H_{21}N_3O_5S$: C, 59.00; H, 4.95; N, 9.83. Found: C, 59.02; H, 4.93; N, 9.77.

g. 1,6-Dihydro-5-methoxycarbonyl-2-[{(4-methoxyphenyl)methyl)}thio]-4-methyl-6-(4-nitrophenyl)-1-[(4-nitrophenyloxy)carbonyl]pyrimidine.

To a well-stirred mixture of 1,6-dihydro-5-methoxy carbonyl-2-[{(4-methoxyphenyl)methyl}thio]-4-methyl-6-(4-nitrophenyl)pyrimidine (4.5 g, 0.0105 mol), $NaHCO_3$ (3.69 g, 0.044 mol), $CH_2Cl_2$ (200 mL), and water (50 mL) at 0–5° C., 4-nitrophenyl chloroformate (2.4 g, 0.0119 mol) was added in 5 min and the mixture was allowed to warm to room temperature. After 10 hours, the TLC analysis of the reaction mixture showed the presence of a small amount of starting pyrimidine, therefore, more 4-nitrophenyl chloroformate (0.65 g, 0.0032 mol) was added and the stirring continued for an additional 4 hours. The two layers were separated, the $CH_2Cl_2$ layer was washed with saturated aqueous $NaHCO_3$ solution (3×50 mL), dried ($MgSO_4$), and the solvent evaporated. The residue was recrystallized from $CH_2Cl_2$ and hexane to give the product as white crystals (5.5 g, 88.4%); m.p. 156–157° C.; $^1$H-NMR ($CDCl_3$): δ 2.53 (s, 3 H), 3.70 (s, 3 H), 3.81 (s, 3 H), 4.06, 4.36 (AB q, J=13.5 Hz, 2 H), 6.30 (s, 1 H), 6.78 (d, J=8.7 Hz, 2 H), 7.17 (d, J=8.5 Hz, 2 H), 7.20 (d, J=8.7 Hz, 2 H), 7.32 (d, J=8.8 Hz, 2 H), 7.97 (d, J=8.8 Hz, 2 H), 8.25 (d, J=8.8 Hz, 2 H); Anal. Calcd. for $C_{28}H_{24}N_4O_9S$: C, 56.75; H, 4.08; N, 9.45. Found: C, 56.49; H, 4.28; N, 9.25.

h. 1,6-Dihydro-5-methoxycarbonyl-2-[{(4-methoxyphenyl)methyl}thio]-4-methyl-6-(4-nitrophenyl)-1-{N-[3-(4,4-diphenylpiperidin-1-yl)prop-yl]}carboxamidopyrimidine.

To a stirred solution of 1,6-dihydro-5-methoxycarbonyl-2-[{(4-methoxyphenyl)methyl}thio]-4-methyl-6-(4-nitrophenyl)-1-[(4-nitrophenyloxy)carbonyl]pyrimidine (0.592 g, 1 mmol) in anhydrous THF (10 mL) at room temperature under argon atmosphere, a solution of 3-[4,4-diphenylpiperidin-1-yl]propylamine (0.441 g, 1.5 mmol, 1.5 eq) in THF (5 mL) was added and the stirring continued for 1 hours. Solvent was evaporated from the reaction mixture and the residue was redissolved in $CH_2Cl_2$ (50 mL), washed with 5% $NaHCO_3$ (3×25 mL), brine (50 mL), and dried ($MgSO_4$). Solvent was evaporated and the residue was purified by flash chromatography on silica gel using 10% methanol in EtOAc as the eluent to give the desired product as an oil, which on trituration with hexane and drops of EtOAc became a white powder (0.32 g, 43%); m.p. 79–80° C.; $^1$H-NMR ($CDCl_3$): δ 1.61–1.82 (m, 4 H), 2.27 (s, 3 H), 2.30–2.51 (m, 8 H), 3.19–3.36 (m, 1 H), 3.42–3.60 (m, 1 H), 3.68 (s, 3 H), 3.76 (s, 3 H), 3.95, 4.22 (AB q, J=13.6 Hz, 2 H), 6.16 (s, 1 H), 6.70 (d, J=8.6 Hz, 2 H), 7.04 (d, J=8.6 Hz, 2 H), 7.11–7.29 (m, 12 H), 7.68 (br t, 1 H, NH), 7.91 (d, J=8.8 Hz, 2 H) ; Anal. Calcd. for $C_{42}H_{45}N_5O_6S \cdot 0.33 CH_2Cl_2$: C, 65.52; H, 5.93; N, 9.03. Found: C, 65.52; H, 6.01; N, 9.20.

EXAMPLE 2

1,6-Dihydro-5-methoxycarbonyl-2-[{(4-methoxyphenyl)methyl}thio]-4-methyl-6-(4-nitrophenyl)-1-{N-[3-(4-phenylpiperidin-1-yl)propyl]}carboxamidopyrimidine.

a. 3-(4-Phenylpiperidin-1-yl)propionitrile.

Acrylonitrile (3.1 mL, 44 mmol, 2.5 eq) was added to a solution of 4-phenylpiperidine (3.0 g, 18 mmol) in EtOH (40 mL) and the mixture was stirred at room temperature for 1.5 hours. The volatiles were removed to give 3.8 g of pure product (brown oil, 99%), which was characterized spectroscopically.

b. 3-(4-Phenylpiperidin-1-yl)propylamine.

To a stirred solution of 3-(4-phenylpiperidin-1-yl) propionitrile (5.1 g, 24 mmol) in anhydrous THF (20 mL) under argon was added a solution of $BH_3$ in THF (1.0M, 83 mL, 83 mmol, 3.5 eq) at room temperature. The mixture was refluxed for 4.5 hours and then cooled to room temperature. Aqueous HCl (6N, 130 mL) was added and stirring was continued for 2 hours at 50–70° C. The mixture was basified to pH 9 by addition of 6N aq. NaOH and extracted with EtOAc (100 mL) and $CH_2Cl_2$ (3×100 mL). The combined organic extracts were dried ($MgSO_4$) and concentrated. The residue was dissolved in $CH_2Cl_2$ (20 mL) and treated with HCl in ether (1.0M, 50 mL). The solvents were removed, ether (250 mL) was added, the mixture was filtered, and the filter cake was washed with ether. Water (60 mL) was added to the resulting white solid, the pH was adjusted to 10–11 with 1N NaOH, and the aqueous phase was extracted with $CH_2Cl_2$ (3×50 mL). The combined extracts were dried ($MgSO_4$) and the solvents evaporated to give 4.5 g (87%) of pure product (light brown solid), which was characterized spectroscopically.

c. 1,6-Dihydro-5-methoxycarbonyl-2-[{(4-methoxyphenyl) methyl}thio]-4-methyl-6-(4-nitrophenyl)-1-{N-[3-(4-phenylpiperidin-1-yl)propyl]}carboxamidopyrimidine.

This compound was prepared from 1,6-dihydro-5-methoxycarbonyl-2-[{(4-methoxyphenyl)methyl}thio]-4-methyl-6-(4-nitrophenyl)-1-[(4-nitrophenyloxy)carbonyl] pyrimidine (0.77 g, 1.3 mmol), 3-[4-phenylpiperidin-1-yl] propylamine (0.34 g, 1.56 mmol, 1.2 eq) and purified using similar conditions described in Example 1 (0.63 g, 72%); m.p. 123–124° C.; $^1$H-NMR ($CDCl_3$): δ 1.65–2.10 (m, 8 H), 2.41 (s, 3 H), 2.41–2.55 (m, 3 H), 2.99–3.06 (m, 2 H), 3.2–3.35 (m, 1 H), 3.45–3.60 (m, 1 H), 3.67 (s, 3 H), 3.75 (s, 3 H), 4.10, 4.33 (AB q, J=13.6 Hz, 2 H), 6.19 (s, 1 H), 6.71 (d, J=8.6 Hz, 2 H), 7.09 (d, J=8.6 Hz, 2 H), 7.20–7.34 (m, 7 H), 7.97 (br t, 1 H, NH), 7.97 (d, J=8.8 Hz, 2 H); Anal. Calcd. for $C_{36}H_{41}N_5O_6S \cdot 0.25\ CH_2Cl_2$: C, 62.82; H, 6.04; N, 10.11. Found: C, 62.54; H, 6.13; N, 10.03.

EXAMPLE 3

1-{N-[3-(4-Cyano-4-phenylpiperidin-1-yl)propyl]}carboxamido-1,6-dihydro-5-methoxycarbonyl-2-[{(4-methoxyphenyl)methyl}thio]-4-methyl-6-(4-nitrophenyl)pyrimidine.

a. 3-(4-Cyano-4-phenylpiperidinlyl)propylamine.

4-Cyano-4-phenylpiperidine hydrochloride (5.01 g, 22.5 mmol) was added to water (100 mL), and the solution was basified to pH 10–11 by addition of 6N aqueous NaOH. The mixture was extracted with $CH_2Cl_2$ (3×100 mL). The combined organic extracts were dried ($MgSO_4$) and concentrated. To the residue were added 3-bromopropylamine hydrobromide (4.92 g, 22.5 mmol), anhydrous $K_2CO_3$ (3.42 g, 24.8 mmol, 1.10 eq), and 1,4-dioxane (100 mL). The mixture was stirred at reflux for 24 hours under a $CaSO_4$ drying tube. The solvent was evaporated, and the product was purified by flash chromatography ($SiO_2$, $CHCl_3$/MeOH/2M $NH_3$ in MeOH (100:8:4 to 100:20:8) to give 3.23 g (59%) of colorless oil, which was characterized spectroscopically.

b. 1-{N-[3-(4-Cyano-4-phenylpiperidin-1-yl)propyl]}carboxamido-1,6-dihydro-5-methoxycarbonyl-2[{(4-methoxy-phenyl)methyl}thio]-4-methyl-6-(4-nitrophenyl) pyrimidine.

This compound was prepared from 1,6-dihydro-5-methoxycarbonyl-2-[{(4-methoxyphenyl)methyl}thio]-4-methyl-6-(4-nitrophenyl)-1-[(4-nitrophenyloxy)carbonyl] pyrimidine (0.592 g, 1 mmol), 3-[4-cyano-4-phenylpiperidin-1-yl]propylamine (0.292 g, 1.2 mmol, 1.2 eq) and purified using similar conditions described in Example 1 (0.445 g, 64%); m.p. 143–144° C.; $^1$H-NMR ($CDCl_3$): δ 1.70–1.86 (m, 2 H), 2.02–2.09 (m, 4 H), 2.38 (s, 3 H), 2.41–2.56 (m, 4 H), 2.95–3.02 (m, 2 H), 3.24–3.40 (m, 1 H), 3.42–3.58 (m, 1 H), 3.68 (s, 3 H), 3.76 (s, 3 H), 4.08, 4.23 (AB q, J=13.5 Hz, 2 H), 6.23 (s, 1 H), 6.72 (d, J=8.6 Hz, 2 H), 6.94 (br t, 1 H, NH), 7.08 (d, J=8.6 Hz, 2 H), 7.29 (d, J=8.7 Hz, 2 H), 7.33–7.49 (m, 5 H), 7.94 (d, J=8.8 Hz, 2 H); Anal. Calcd. for $C_{37}H_{40}N_6O_6S$: C, 63.78; H, 5.79; N, 12.06. Found: C, 63.86; H, 5.90; N, 11.92.

EXAMPLE 4

1,6-Dihydro-5-methoxycarbonyl-1-{N-[3-(4-methoxycarbonyl-4-phenylpiperidin-1-yl)propyl]}carboxamido-2-[{(4-methoxyphenyl)methyl}thio]-4-methyl-6-(4-nitrophenyl)pyrimidine.

a. 4-Methoxycarbonyl-4-phenylpiperidine.

To a stirred solution of $H_2SO_4$ (16 mL) in MeOH (400 mL), 4-phenyl-4-piperidinecarboxylic acid 4-methylbenzenesulfonate (37.7 g, 0.1 mole) was added and the mixture was stirred and refluxed for 8 hours. Excess methanol was evaporated at reduced pressure and the residue was poured into a mixture of ice and 6N NaOH. The pH was adjusted to 10–11 by adding more 6N NaOH and extracted with $CH_2Cl_2$ (3×150 mL). The combined $CH_2Cl_2$ extracts were dried ($MgSO_4$) and the solvent evaporated to leave the desired product as a viscous oil. The product (20.2 g, 92%) was used without further purification.

b. 3-(4-Methoxycarbonyl-4-phenylpiperidin-1-yl) propylamine.

A mixture of 4-methoxycarbonyl-4-phenylpiperidine (8.5 g, 0.039 mol), 3-bromopropylamine hydrobromide (12.7 g, 0.058 mol), potassium carbonate (13.475 g, 0.0957 mole), and KI (3.24 g, 0.0195 mol) in 1,4-dioxane (200 mL) was stirred and refluxed for 24 hours. Dioxane was evaporated at reduced pressure, the residue was treated with ice-cold 6N NaOH (400 mL) and extracted with $CH_2Cl_2$ (4×120 mL). Solvent was evaporated from the combined dried ($K_2CO_3$) extracts and the residue was purified by column chromatography on silica gel using $CHCl_3$/MeOH/2M $NH_3$ in MeOH (20:2:1) as the eluent to afford the product as a viscous oil (7.8 g, 72%).

c. 1,6-Dihydro-5-methoxycarbonyl-1-{N-[3-(4-methoxycarbonyl-4-phenylpiperidin-1-yl)propyl]}carboxamido-2-[{(4-methoxyphenyl)methyl}thio]-4-methyl-6-(4-nitrophenyl)pyrimidine.

This compound was prepared from 1,6-dihydro-5-methoxycarbonyl-2-[{(4-methoxyphenyl)methyl}thio]-4-methyl-6-(4-nitrophenyl)-1-[(4-nitrophenyl-oxy)carbonyl] pyrimidine (1.0 g, 1.69 mmol), 3-[4-methoxycarbonyl-4-phenylpiperidin-1-yl]propylamine (0.56 g, 2.03 mmol, 1.2 eq) and purified using similar conditions described in Example 1 (1.085 g, 88%); m.p. 140–141° C.; $^1$H-NMR ($CDCl_3$): δ 1.62–1.74 (m, 2 H), 1.82–2.18 (m, 4 H), 2.21 (s, 3 H), 2.35–2.58 (m, 4 H), 2.75–2.89 (m, 2 H), 3.18–3.30 (m, 1 H), 3.42–3.58 (m, 1 H), 3.61 (s, 3 H), 3.66 (s, 3 H), 3.75 (s, 3 H), 3.91, 4.15 (AB q, J=13.6 Hz, 2 H), 6.14 (s, 1 H), 6.69 (d, J=8.6 Hz, 2 H), 7.02 (d, J=8.6 Hz, 2 H), 7.20–7.37 (m, 7 H), 7.56 (br t, 1 H, NH), 7.90 (d, J=8.8 Hz, 2 H); Anal. Calcd. for $C_{38}H_{43}N_5O_8S$: C, 62.54; H, 5.94; N, 9.60. Found: C, 62.41; H, 6.06; N, 9.34.

EXAMPLE 5

5-Methoxycarbonyl-4-methyl-6-(4-nitrophenyl)-1-{N-[3-(4,4-diphenyl-piperidin-1-yl)propyl]}carboxamido-1,2,3,6-tetrahydro-2-thioxo-pyrimidine.

To a stirred solution of 1,6-dihydro-6-methoxycarbonyl-2-[{(4-methoxyphenyl)methyl}thio]-4-methyl-6-(4- nitrophenyl)-1-{N-[3-(4,4-diphenylpiperidin-1-yl)propyl]}carboxamidopyrimidine (0.14 g, 0.187 mmol) and ethanethiol (0.5 mL) in CH$_2$Cl$_2$ (5 mL) at 5° C. under argon, TFA (0.5 mL) was added and the mixture was allowed to warm to room temperature. After 3 hours, solvents were evaporated completely, the residue was redissolved in EtOAc (10 mL), washed with 5% NaHCO$_3$ (5×1 mL) and dried (MgSO$_4$). Solvent was evaporated and the residue was purified by column chromatography using 1:1 hexane/EtOAc to 100% EtOAc as gradient eluent. The oily product was crystallized from hexane and EtOAc (0.096 g, 82%); m.p. 130–131° C.; $^1$H-NMR (CDCl$_3$): δ 1.65–1.80 (m, 2 H), 2.31 (s, 3 H), 2.31–2.49 (m, 10 H), 3.25–3.55 (m, 2 H), 3.76 (s, 3 H), 7.01 (s, 1 H), 7.09–7.29 (m, 6 H), 7.41 (d, J=8.2 Hz, 2 H), 8.11 (d, J=8.8 Hz, 2 H), 9.76 (br t, 1 H, NH); Anal. Calcd. for C$_{34}$H$_{37}$N$_5$O$_6$S.0.3 H$_2$O: C, 64.50; H, 5.89; N, 11.06. Found: C, 64.45; H, 6.05; N, 10.87.

EXAMPLE 6

5-Methoxycarbonyl-4-methyl-6-(4-nitrophenyl)-1-{N-[3-(4-phenyl-piperidin-1-yl)propyl]}carboxamido-1,2,3,6-tetrahydro-2-thioxo-pyrimidine.

This compound was prepared from 1,6-dihydro-3-{N-[3-(4-phenylpiperidin-1-yl)propyl]}carboxamido-6-methoxycarbonyl-2-[{(4-methoxyphenyl)methyl}thio]-6-(4-nitrophenyl)-4-methylpyrimidine (0.15 g, 0.223 mmol) using the procedure described in Example 5 and purified by flash column chromatography (0.102 g, 83%); m.p. 134–135° C.; $^1$H-NMR (CDCl$_3$): δ 1.72–1.94 (m, 4 H), 1.96–2.11 (m, 2 H), 2.36 (s, 3 H), 3.0–3.09 (m, 2 H), 3.32–3.49 (m, 2 H), 3.76 (s, 3 H), 7.06 (s, 1 H), 7.17–7.30 (m, 6 H), 7.42 (d, J=8.7 Hz, 2 H), 8.11 (d, J=8.8 Hz, 2 H), 9.80 (br t, 1 H, NH) ; Anal. Calcd. for C$_{28}$H$_{33}$N$_5$O$_5$S: C, 60.96; H, 6.03; N, 12.70. Found: C, 60.63; H, 5.78; N, 12.55.

EXAMPLE 7

1-{N-[3-(4-Cyano-4-phenylpiperidin-1-yl)propyl]}carboxamido-5-methoxycarbonyl-4-methyl-6-(4-nitrophenyl)-1,2,3,6-tetrahydro-2-thioxopyrimidine.

This compound was prepared from 1-{N-[3-(4-cyano-4-phenylpiperidin-1-yl)propyl]}carboxamido-1,6-dihydro-6-methoxycarbonyl-2-[{(4-methoxyphenyl)methyl}thio]-6-(4-nitrophenyl)-4-methylpyrimidine (0.15 g, 0.215 mmol) using the procedure described in Example 5 and purified by flash column chromatography (0.118 g, 95%); m.p. 137–138° C.; $^1$H-NMR (CDCl$_3$): δ 1.69–1.85 (m, 2 H), 2.07–2.20 (m, 4 H), 2.37 (s, 3 H), 2.37–2.60 (m, 4 H), 2.96–3.06 (m, 2 H), 3.31–3.86 (m, 2 H), 3.76 (s, 3 H), 7.09 (s, 1 H), 7.31–7.49 (m, 7 H), 7.92 (br s, 1 H, NH), 8.12 (d, J=8.8 Hz, 2 H), 9.84 (br t, 1 H, NH); Anal. Calcd. for C$_{29}$H$_{32}$N$_6$O$_5$S: C, 60.53; H, 5.74; N, 14.49. Found: C, 60.53; H, 5.74; N, 14.48.

EXAMPLE 8

5-Methoxycarbonyl-1-{N-[3-(4-methoxycarbonyl-4-phenylpiperidin-1-yl)propyl]}carboxamido-4-methyl-6-(4-nitrophenyl)-1,2,3,6-tetrahydro-2-thioxopyrimidine This compound was prepared from 1,6-dihydro-6-methoxycarbonyl-3-{N-[4-methoxycarbonyl-phenyl-piperidin-1-yl]propyl}carboxamido-2-[{(4-methoxyphenyl)methyl}thio]-6-(4-nitrophenyl)-4-methylpyrimidine (0.730 g, 1 mmol) using the procedure described in Example 5 and purified by flash column chromatography (0.57 g, 94%); m.p. 135–136° C.; $^1$H-NMR (CDCl$_3$): δ 1.62–2.13 (m, 6 H), 2.32 (s, 3 H), 2.33–2.39 (m, 4 H), 2.76–2.84 (m, 2H), 3.34–3.43 (m, 2 H), 3.61 (s, 3 H), 3.75(s, 3 H), 7.04 (s, 1 H), 7.21–7.35 (m, 5 H), 7.40 (d, J=8.6 Hz, 2 H), 7.82 (br s, 1 H, NH), 8.10 (d, J=8.9 Hz, 2 H), 9.76 (br t, 1 H, NH); Anal. Calcd. for C$_{30}$H$_{35}$N$_5$O$_7$S: C, 59.10; H, 5.79; N, 11.49. Found: C, 59.08; H, 5.91; N, 11.31.

EXAMPLE 9

1-{N-[3-(4-(4-Methoxyphenyl)-4-phenylpiperidin-1-yl)propyl]}carboxamido-5-methoxycarbonyl-4-methyl-6-(4-nitrophenyl)-1,2,3,6-tetrahydro-2-thioxopyrimidine.

a. 4-(4-Methoxyphenyl)-4-phenylpiperidine.

4-Hydroxy-4-phenylpiperidine (5.00 g, 28.2 mmol) was added to a suspension of AlCl$_3$ (18.8 g, 0.141 mol, 5.00 eq) in anhydrous anisole (100 mL). The mixture was stirred at room temperature for 1 hours and then heated to 50° C. for 3.5 hours. It was cooled to room temperature and poured cautiously into ice-water. The mixture was basified to pH 11 by addition of 6N aqueous NaOH, and extracted with EtOAc (3×75 mL). The combined organic extracts were applied directly to a flash chromatography column, which was eluted with CH$_2$Cl$_2$/0.67M NH$_3$ in MeOH (4:1) to afford 1.683 g (22%) of light yellow oil, which was characterized spectroscopically.

b. 3-[4-(4-Methoxyphenyl)-4-phenylpiperidin-1-yl]propionitrile.

Acrylonitrile (1.03 mL, 15.7 mmol, 2.50 eq) was added at 0° C. to a solution of 4-(4-methoxyphenyl)-4-phenylpiperidine (1.68 g, 6.28 mmol) in EtOH (20 mL) and the resulting solution was stirred for 1.5 hours at room temperature. After removal of the solvent, the residue was purified by flash chromatography (SiO$_2$, EtOAc-CHCl$_3$ 1:3) to give 1.41 g (70%) of colorless oil, which was characterized spectroscopically.

c. 3-[4-(4-Methoxyphenyl)-4-phenylpiperidin-1-yl]propylamine.

To a stirred solution of 3-[4-(4-methoxyphenyl)-4-phenylpiperidin-1-yl]propionitrile (1.41 g, 4.40 mmol) in anhydrous THF (10 mL) under argon was added a solution of BH$_3$ in THF (1.0M, 11.0 mL, 2.5 eq) at room temperature. The mixture was refluxed for 4.5 hours and then cooled to room temperature. Aqueous HCl (6N, 15 mL) was added and stirring was continued for 2 h at 55–60° C. The mixture was basified to pH 9 by addition of 6N aq. NaOH and extracted with CH$_2$Cl$_2$ (3×75 mL). The combined organic solutions were dried (MgSO$_4$) and concentrated. The residue was dissolved in CH$_2$Cl$_2$ (10 mL) and treated with HCl in ether (1.0M, 9.0 mL, 2.0 eq). The solvents were removed, ether (30 mL) was added, the mixture was filtered, and the filter cake was washed with ether (2×10 mL). Water (20 mL) was added to the resulting white solid, the pH was adjusted to 10 with 1 N NaOH, and the aqueous phase was extracted with CH$_2$Cl$_2$ (3×40 mL). The combined organic extracts were dried (MgSO$_4$) and concentrated to give 610 mg (43%) of white solid, which was characterized spectroscopically.

d. 1-{N-[3-(4-(4-Methoxyphenyl)-4-phenylpiperidin-1-yl) propyl]}carboxamido-5-methoxycarbonyl-4-methyl-6-(4-nitrophenyl)-1,2,3,6-tetrahydro-2-thioxopyrimidine.

To a stirred mixture of 1,6-dihydro-5-methoxycarbonyl-2-[{(4-methoxyphenyl)methyl}thio]-4-methyl-6-(4-nitrophenyl)-1-[(4-nitrophenyloxy)carbonyl]pyrimidine (0.592 g, 1 mmol) and K$_2$CO$_3$ (0.276 g, 2 mmol) in anhydrous THF (10 mL) at room temperature under argon atmosphere, a solution of 3-[4-(4-methoxyphenyl)-4-phenylpiperidin-1-yl]propylamine (0.390 g, 1.2 mmol, 1.2 eq) in THF (10 mL) was added and the stirring was continued for 1 hour. Solvent was evaporated from the reaction mixture and the residue was redissolved in $CH_2Cl_2$ (50 mL), washed with 5% $NaHCO_3$ (3×25 mL), brine (50 mL), and dried ($MgSO_4$). The $CH_2Cl_2$ solution was filtered and cooled to 5° C. To this, ethanethiol (0.5 mL) and TFA (0.5 mL) were added and the mixture was stirred and allowed to warm to room temperature. After 3 hours, solvents were evaporated completely, the residue was redissolved in EtOAc (10 mL), washed with 5% $NaHCO_3$ (5×1 mL), and dried ($MgSO_4$). Solvent was evaporated and the residue was purified by column chromatography using 1:1 hexane/EtOAc to 100% EtOAc as gradient eluent. The oily product was crystallized from hexane and EtOAc (0.41 g, 62%); m.p. 120–121° C.; $^1$H-NMR ($CDCl_3$): δ 1.60–1.80 (m, 2 H), 2.31 (s, 3 H), 2.31–2.51 (m, 8 H), 3.32–3.43 (m, 2 H), 3.75 (s, 3 H), 3.76 (s, 3 H), 6.77 (d, J=8.8 Hz, 2 H), 7.02 (s, 1 H), 7.12 (d, J=8.6 Hz, 2 H), 7.20–7.27 (m, 6 H), 7.41 (d, J=8.6 Hz, 2 H), 8.11 (d, J=8.8 Hz, 2 H), 9.76 (br t, 1 H, NH); Anal. Calcd. for $C_{35}H_{39}N_5O_6S$: C, 63.91; H, 5.98; N, 10.65. Found: C, 64.19; H,6.22; N, 10.36.

EXAMPLE 10 a. 4-Ethoxycarbonyl-4-phenylpiperidine.

To a stirred solution of $H_2SO_4$ (1.62 g, 16.56 mmol) in EtOH (200 mL), 4-phenyl-4-piperidine-carboxylic acid 4-methylbenzenesulfonate (25 g, 66.23 mmol) was added and the mixture was stirred and refluxed for 12 hours. Excess ethanol was evaporated at reduced pressure and the residue was poured into a mixture of ice and 6N NaOH. The pH was adjusted to 10–11 by adding more 6N NaOH and extracted with $CH_2Cl_2$ (3×100 mL). The combined $CH_2Cl_2$ extracts were dried ($MgSO_4$) and the solvent evaporated to leave the desired product as a colorless viscous oil, the $^1$H-NMR showed it to be pure (14.68 g, 95%) and was used without any further purification.

b. 3-(4-Ethoxycarbonyl-4-phenylpiperidin-1-yl) propylamine.

A mixture of 4-ethoxycarbonyl-4-phenylpiperidine (30.5 g, 0.131 mol), 3-bromopropylamine hydrobromide (42.93 g, 0.196 mol), potassium carbonate (36.14 g, 0.241 mole), and KI (10.8 g, 0.065 mol) in 1,4-dioxane (500 mL) was stirred and refluxed for 24 hours. Dioxane was evaporated at reduced pressure, the residue was treated with ice-cold 6N NaOH (400 mL) and extracted with $CH_2Cl_2$ (4×120 mL). Solvent was evaporated from the combined dried ($K_2CO_3$) $CH_2Cl_2$ extracts and the residue was purified by column chromatography on silica gel using $CHCl_3$/MeOH/2 M $NH_3$ in MeOH (20:2:1) as the eluent to afford the product as a viscous oil (24.2 g, 83.3%).

c. 1-{N-[3-(4-Ethoxycarbonyl-4-phenylpiperidin-1-yl) propyl]}carboxamido-5-methoxycarbonyl-4-methyl-6-(4-nitrophenyl)-1,2,3,6-tetra-hydro-2-thioxopyrimidine.

This compound was prepared from 1,6-dihydro-5-methoxycarbonyl-2-[{(4-methoxyphenyl)methyl}thio]-4-methyl-6-(4-nitrophen-yl)-1-[(4-nitrophenyloxy)carbonyl] pyrimidine (0.592 g, 1 mmol), $K_2CO_3$ (0.276 g, 2 mmol), 3-[4-ethoxycarbonyl-4-phenylpiperidin-1-yl]proylamine (0.350 g, 1.2 mmol, 1.2 eq), ethanethiol (0.5 mL), and TFA (0.5 mL) using the procedure described in Example 10 and purified by flash column chromatography (0.295 g, 47%); m.p. 125–126° C.; $^1$H-NMR ($CDCl_3$): δ 1.13 (t, J=7 Hz, 3 H), 1.62–1.80 (m, 2 H), 1.87–2.0 (m, 2 H), 2.06–2.18 (m, 2 H), 2.31 (s, 3 H), 2.34–2.39 (m, 2 H), 2.50–2.55 (m, 2 H), 2.79–2.83 (m, 2 H), 3.30–3.51 (m, 2 H), 3.74 (s, 3 H), 4.07 (q, J=7 Hz, 2 H), 7.03 (s, 1 H), 7.18–7.36 (m, 6 H), 7.40 (d, J=8.8 Hz, 2 H), 8.08 (d, J=8.8 Hz, 2 H), 9.78 (br t, 1 H, NH) ; Anal. Calcd. for $C_{31}H_{37}N_5O_7S$: C, 59.70; H, 5.98; N, 11.23. Found: C, 59.55; H, 5.99; N, 11.43.

EXAMPLE 11

1, 6-Dihydro-1-{N-[3-(4,4-diphenylpiperidin-1-yl) propyl]}carboxamido-2-methoxy-5-methoxycarbonyl-4-methyl-6-(4-nitrophenyl) pyrimidine.

To a stirred mixture of 1,6-dihydro-2-methoxy-5-methoxycarbonyl-4-methyl-6-(4-nitrophenyl)-1-[(4-nitrophenyloxy)carbonyl]pyrimidine (0.940 g, 2 mmol) and $K_2CO_3$ (0.552 g, 4 mmol) in anhydrous THF (20 mL) at room temperature under argon atmosphere, a solution of 3-[4,4-diphenylpiperidin-1-yl]propylamine (0.882 g, 3 mmol, 1.5 eq) in THF (5 mL) was added and the stirring was continued for 1 hour. Solvent was evaporated from the reaction mixture, the residue was redissolved in $CH_2Cl_2$ (50 mL), washed with 5% $NaHCO_3$ (3×25 mL), brine (50 mL), and dried ($MgSO_4$). Solvent was evaporated and the residue was purified by flash chromatography on silica gel using 10% methanol in EtOAc as the eluent to give the desired product as an oil, which on trituration with hexane and drops of EtOAc became a white powder (1.10 g, 88%); m.p. 95–96° C.; $^1$H-NMR ($CDCl_3$): δ 1.61–1.71 (m, 2 H), 2.26–2.33 (m, 2 H), 2.38 (s, 3 H), 2.39–2.50 (m, 8 H), 3.20–3.41 (m, 2 H), 3.65 (s, 3 H), 3.89 (s, 3 H), 6.65 (s, 1 H), 6.84 (br t, 1 H, NH), 7.08–7.29 (m, 10 H), 7.40 (d, J=8.7 Hz, 2 H), 8.03 (d, J=8.6 Hz, 2 H) ; Anal. Calcd. for $C_{35}H_{39}N_5O_6 \cdot 0.75\ CH_2Cl_2$: C, 62.28; H, 5.92; N, 10.16. Found: C, 62.23; H, 5.76; N, 10.12.

EXAMPLE 12

5-Methoxycarbonyl-4-methyl-6-(4-nitrophenyl)-1-{N-[3-(4,4-diphenyl-piperidin-1-yl)propyl]}carboxamido2-oxo-1,2,3,6-tetrahydropyrimid-ine.

a. 1,6-Dihydro-5-methoxycarbonyl-2-methoxy-4-methyl-6-(4nitro-phenyl)pyrimidine.

A mixture of methyl 2-{(4-nitrophen-yl)methylene}-3-oxobutyrate (12.46 g, 0.05 mol), O-methylisourea hydrogen sulfate (10.32 g, 0.06 mol), and NaOAc (9.84 g, 0.06 mol) in DMF (50 mL) was stirred and heated at 70–75° C. for 4 hours. The mixture was cooled and poured into ice-water (300 mL). The precipitate formed was filtered, washed with water, and dried. The crude product was purified by flash column chromatography on silica gel using 10% through 30% EtOAc in hexane as the gradient eluent (9.8 g, 64%). The $^1$H-NMR analysis of the product showed it to be a 19:1 mixture of the amine/imine tautomers which was used as such in the next step. $^1$H-NMR ($CDCl_3$): δ 2.32, 2.38 (2 s, 3 H), 3.59, 3.70 (2 s, 3 H), 3.70, 3.85 (2 s, 3 H), 5.40, 5.66 (s, d, J=3 Hz, 1 H), 5.50, 6.08 (s, d, J=3 Hz, 1 H), 7.43, 7.45 (2 d, J=9 Hz, 2 H), 8.10, 8.11 (2 d, J=9 Hz, 2 H).

b. 1,6-Dihydro-2-methoxy-5-methoxycarbonyl-4-methyl-6-(4nitrophenyl)-1-[(4-nitrophenyloxy)carbonyl]pyrimidine.

To a well-stirred mixture of 1,6-dihydro-2-methoxy-5-methoxycarbonyl-4-methyl-6-(4-nitrophenyl)pyrimidine (5.7 g, 0.0187 mol), $NaHCO_3$ (6.27 g, 0.074 mol), $CH_2Cl_2$ (200 mL), and water (50 mL) at 0–5° C., 4-nitrophenyl chloroformate (3.76 g, 0.0186 mol) was added in 5 min and the mixture was allowed to warm to room temperature. After 10 hours, the TLC analysis of the reaction mixture showed the presence of a small amount of starting pyrimidine, therefore, more 4-nitrophenyl chloroformate (0.65 g, 0.0032 mol) was added and the stirring continued for an additional 4 hours. The two layers were separated, the $CH_2Cl_2$ layer was washed with saturated aqueous $NaHCO_3$ solution (3×50 mL), dried ($MgSO_4$), and the solvent evaporated. The residue was recrystallized from $CH_2Cl_2$ and hexane to give the product as white crystals (12.8 g, 89%); $^1$H-NMR ($CDCl_3$): δ 2.48 (s, 3 H), 3.69 (s, 3 H), 3.94 (s, 3 H), 6.34 (s, 1 H), 7.36 (d, J=9.1 Hz, 2 H), 7.46 (d, J=8.7 Hz, 2 H), 8.14 (d, J=8.7 Hz, 2 H), 8.26 (d, J=9.1 Hz, 2 H); m.p. 168–169° C. Anal. Calcd. for $C_{21}H_{18}N_4O_9$: C, 53.62; H, 3.86; N, 11.91. Found: C, 53.69; H, 3.92; N, 11.85.

c. 5-Methoxycarbonyl-4-methyl-6-(4-nitrophenyl)-1-{N-[3(4,4-di-phenylpiperidin-1-yl)propyl]}carboxamido2-oxo-1,2,3,6-tetrahydro-pyrimidine.

To a stirred solution of 1,6-dihydro-2-methoxy-6methoxycarbonyl-4-methyl-6-(4-nitrophenyl)-1-{N-[3(4,4-diphenylpiperidin-1-yl)propyl]}carboxamidopyrimidine (0.208 g, 0.33 mmol) in THF (10 mL) at 5° C. under argon, 3N HCl (6 mL) was added and the mixture was allowed to warm to room temperature. After 2 hours, solvents were evaporated completely, the residue was treated with 40 mL of 10% $NaHCO_3$, the product was extracted with $CH_2Cl_2$ (2×15 mL) and the combined extracts were dried ($MgSO_4$). Solvent was evaporated and the residue was crystallized from hexane and EtOAc (0.20 g, 97%); m.p. 197–198° C.; $^1$HNMR ($CDCl_3$): δ 1.63–1.67 (m, 2 H), 2.23–2.28 (m, 2 H), 2.34 (s, 3 H), 2.37–2.42 (m, 8 H), 3.20–3.41 (m, 2 H), 3.69 (s, 3 H), 6.75 (s, 1 H), 7.08–7.26 (m, 11 H), 7.46 (d, J=8.7 Hz, 2 H), 8.08 (d, J=8.7 Hz, 2 H), 8.77 (br t, 1 H, NH); Anal. Calcd. for $C_{34}H_{37}N_5O_6$: C, 66.76; H. 6.10; N, 11.45. Found: C, 66.48; H, 5.97; N, 11.25.

EXAMPLE 13

1-{N-[3-(4-(4-Methoxyphenyl)-4-phenylpiperidin-1-yl)propyl]}carboxamido-5-methoxycarbonyl-4-methyl-6-(4-nitrophenyl)-2-oxo-1,2,3,6-tetrahydropyrimidine.

To a stirred mixture of 1,6-dihydro-2-meth-oxy-5-methoxycarbonyl-4-methyl-6-(4-nitrophenyl)-1-[(4-nitrophenyloxy)carbonyl]pyrimidine (0.47 g, 1 mmol) and $K_2CO_3$ (0.552 g, 4 mmol) in anhydrous THF (10 mL) at room temperature under argon atmosphere, a solution of 3-[4-(4-methoxyphenyl)-4-phenylpiperidin-1-yl]propyl-amine (0.390 g, 1.2 mmol, 1.2 eq) in THF (10 mL) was added and the stirring was continued for 2 hours. The solid was removed by filtration and the solution was cooled to 0–5° C. 6N HCl (2 mL) was added to the solution and stirring was continued. After 3 hours, solvents were evaporated completely, the residue was redissolved in $CH_2Cl_2$ (20 mL), washed with 10% $NaHCO_3$ (2×10 mL), and dried ($MgSO_4$). Solvent was evaporated and the residue was purified by column chromatography using 1:1 hexane/EtOAc to 100% EtOAc as gradient eluent. The oily product was crystallized from hexane and EtOAc (0.55 g, 86%); m.p. 100–102° C.; $^1$H-NMR ($CDCl_3$): δ 1.65–1.80 (m, 2 H), 2.26–2.31 (m, 2 H), 2.35 (s, 3 H), 2.39–2.44 (m, 6 H), 3.18–3.40 (m, 2 H), 3.69 (s, 3 H), 3.73 (s, 3 H), 6.75 (s, 1 H), 7.60 (d, J=8.7 Hz, 2 H), 6.84 (br s, 1 H, NH), 7.10 (d, J=8.7 Hz, 2 H), 7.18–7.26 (m, 5 H), 7.46 (d, J=8.6 Hz, 2 H), 8.08 (d, J=8.6 Hz, 2 H), 8.78 (br t, 1 H, NH) ; Anal. Calcd. for $C_{35}H_{39}N_5O_7$·0.12 $CH_2Cl_2$·0.12 EtOAc: C, 64.54; H, 6.12; N, 10.57. Found: C, 64.44; H, 6.12; N, 10.28.

EXAMPLE 14

1-{N-[3-(4-Methoxycarbonyl-4-phenylpiperidin-1yl)propyl]}carboxamido-5-methoxycarbonyl-4-methyl-6-(4-nitrophenyl)-2-oxo-1,2,3,6-tetrahydropyrimidine (Scheme 2).

To a stirred mixture of 1,6-dihydro-2-methoxy-5methoxycarbonyl-4-methyl-6-(4-nitrophenyl)-1-[(4-nitrophenyloxy)carbonyl]pyrimidine (0.47 g, 1 mmol), $K_2CO_3$ (0.276 g, 2 mmol) in anhydrous THF (10 mL) at room temperature under argon atmosphere, a solution of 3-[4methoxycarbonyl-4-phenylpiperidin-1-yl]propylamine (0.332 g, 1.2 mmol, 1.2 eq) in THF (10 mL) was added and the stirring was continued for 2 hours. The solid was removed by filtration and the solution was cooled to 0–5° C. To this, 6N HCl (2 mL) was added and the stirring continued. After 3 hours, solvents were evaporated completely, the residue was redissolved in $CH_2Cl_2$ (20 mL), washed with 10% $NaHCO_3$ (2×10 mL), and dried ($MgSO_4$).

Solvent was evaporated and the residue was purified by column chromatography using 1:1 hexane/EtOAc to 100% EtOAc as gradient eluent. The oily product was crystallized from hexane and EtOAc (0.55 g, 86%); m.p. 180–181° C.; $^1$H-NMR ($CDCl_3$): δ 1.60–1.80 (m, 2 H), 1.85–1.95 (m, 2 H), 2.03–2.10 (m, 2 H), 2.28–2.33 (m, 2 H), 2.35 (s, 3 H), 2.48–2.50 (m, 2 H), 3.20–3.40 (m, 2 H), 3.60 (s, 3 H), 3.68 (s, 3 H), 6.75 (s, 1 H), 7.20–7.34 (m, 6 H), 7.46 (d, J=8.8 Hz, 2 H), 8.07 (d, J=8.8 Hz, 2 H), 8.78 (br t, 1 H, NH); Anal. Calcd. for $C_{30}H_{35}N_5O_8$: C, 60.70; H, 5.94; N, 11.80. Found: C, 60.71; H, 5.99; N, 11.43.

EXAMPLE 14a & 14b (+)-1-{N-[3-(4-Methoxycarbonyl-4-phenylpiperidin-1-yl)propyl]}carboxamido-5-methoxycarbonyl-4-methyl-6(4-nitrophenyl)-2-oxo-1,2,3,6-tetrahydropyrimidine and (−)-1-{N-[3-(4-Methoxycarbonyl-4-phenyl-piperidin-1-yl)propyl]}carboxamido-5-methoxycarbonyl-4-methyl-6-(4nitrophenyl)-2-oxo-1,2,3,6-tetrahydropyrimidine (Scheme 3).

a. (−)-1,6-Dihydro-2-methoxy-5-methoxycarbonyl-4-methyl6-(4-nitro-phenyl)-1-{N-[(2-phenyl)ethyl]}carboxamidopyrimidine and (+)-1,6-Dihydro-2-methoxy-5-methoxycarbonyl-4-methyl-6-(4-nitrophenyl)-1-{N-[(2-phenyl)ethyl]}carboxamidopyrimidine.

To a stirred solution of (±)-1,6-dihydro-2-methoxy-5methoxycarbonyl-4-methyl-6-(4-nitrophenyl)-1-[(4-nitrophenyloxy)carbonyl]pyrimidine (2.66 g, 5.6 mmol) in anhydrous THF (80 mL) at room temperature under argon atmosphere, a solution of (S)-(−)-α-methylbenzylamine (0.82 g, 6.78 mmol, 1.2 eq) in THF (5 mL) was added and the stirring was continued for 6 hours. Solvent was evaporated from the reaction mixture, the residue was redissolved in $CH_2Cl_2$ (50 mL), washed with 5% $NaHCO_3$ (3×25 mL), brine (50 mL), and dried ($MgSO_4$). Solvent was evaporated and the residue was purified by flash chromatography on silica gel using 5% to 30% EtOAc in hexane as the gradient eluent. The first major product to elute was (−)-1,6-dihydro-2-methoxy-5-methoxycarbonyl-4-methyl-6-(4-nitrophenyl)-1-({N-[(2-phenyl)ethyl]}carboxamidopyrimidine and this compound was crystallized from isopropyl ether (0.85 g, 33.6w); m.p. 119–120° C.; $[α]_D$=−329.32 ($CH_2Cl_2$, 10.3 g/100 mL) ; $^1$H-NMR ($CDCl_3$): δ 1.47 (d, J=7 Hz, 3 H), 2.40 (s, 3 H), 3.61 (s, 3 H), 3.95 (s, 3 H), 4.96 (quint, J=6.5 Hz, 2 H), 6.66 (s, 1 H), 6.82 (d, J=6.8 Hz, 1 H, NH), 7.22–7.36 (m, 5 H), 7.43 (d, J=8.6 Hz, 2 H), 8.09 (d, J=8.6 Hz, 2 H); Anal. Calcd. for $C_{23}H_{24}N_4O_6$: C, 61.06; H, 5.35; N, 12.38. Found: C, 60.85; H, 5.13; N, 12.42. The second major compound to elute was (+)-1,6-dihydro-2-methoxy-5methoxycarbonyl-4-methyl-6-(4-nitrophenyl)-1-{[(2-phenyl)ethyl]}carboxamidopyrimidine and this compound was crystallized from isopropyl ether (0.92 g, 36.4%); m.p. 138–140° C.; $[α]_D$=+171.81 ($CH_2Cl_2$, 11.31 g/100 mL) ; $^1$H-NMR (CDCl$_3$): δ 1.47 (d, J=7 Hz, 3 H), 2.42 (s, 3 H), 3.644 (s, 3 H), 3.917 (s, 3 H), 4.989 (quint, J=6.5 Hz, 2 H), 6.70 (s, 1 H), 6.81 (d, J=6.8 Hz, 1 H, NH), 7.22–7.35 (m, 5 H), 7.36 (d, J=8.6 Hz, 2 H), 8.04 (d, J=8.6 Hz, 2 H) ; Anal. Calcd. for C$_{23}$H$_{24}$N$_4$O$_6$: C, 61.06; H, 5.35; N, 12.38. Found: C, 60.95; H, 5.20; N, 12.38.

b. (+)-1-{N-[3-(4-Methoxycarbonyl-4-phenylpiperidin-1-yl)propyl]}carboxamido-5-methoxycarbonyl-4-methyl6-(4-nitrophenyl)-2-oxo-1,2,3,6-tetrahydropyrimidine.

A solution of (+)-1,6-dihydro-2-methoxy-5-methoxycarbonyl-4-methyl-6-(4-nitrophenyl)-1-{N-[(2-phenyl)ethyl]}carboxamidopyrimidine (0.226 g, 0.5 mmol) and 1,8-diazabicyclo[5.4.0]-unde-7-ene (DBU) (0.076 g, 0.5 mmol) in CH$_2$Cl$_2$ (10 mL) was stirred and refluxed for 4 hours and the solvent evaporated. The product was purified by column chromatography using 30% EtOAc in hexane as the eluent. The product was found to be a mixture of the amine-imine tautomers (0.120 g, 78.7%); [α]$_D$=+14.5 (CH$_2$Cl$_2$, 6 g/100 mL).

To a well-stirred solution of (+)-1,6-dihydro-5-methoxycarbonyl-2-methoxy-4-methyl-6-(4-nitrophenyl) pyrimidine (0.12 g, 0.393 mmol) and pyridine (0.5 mL) in CH$_2$Cl$_2$ (10 mL) at 0–5° C., 4-nitrophenyl chloroformate (0.095 g, 0.472 mmol) was added in 5 min and the mixture was allowed to warm to room temperature. After 2 h, saturated aqueous NaHCO$_3$ solution (10 mL) was added and the stirring continued for 30 min. The two layers were separated, the CH$_2$Cl$_2$ layer was washed with saturated aqueous NaHCO$_3$ solution (3×5 mL), dried (Na$_2$SO$_4$), and the solvent evaporated. The residue was redissolved in THF (10 mL) and mixed with K$_2$CO$_3$ (0.11 g, 0.8 mmol). To this, a solution of 3-[4-methoxycarbonyl-4-phenylpiperidin-1-yl]propylamine (0.138 g, 0.5 mmol) in THF (5 mL) was added and the mixture was stirred for 2 hours. The solid was removed by filtration and the solution was cooled to 0–5° C. To this, 6N HCl (0.5 mL) was added and the stirring continued. After 3 hours, solvents were evaporated completely, the residue was redissolved in CH$_2$Cl$_2$ (20 mL), washed with 10% NaHCO$_3$ (4×5 mL), and dried (MgSO$_4$). Solvent was evaporated and the residue was purified by column chromatography using 1:1 hexane/EtOAc to 100% EtOAc as gradient eluent. The oily product was crystallized from hexane and EtOAc (0.19 g, 82%); m.p. 138–140° C.; [α]$_D$=+108 (CH$_2$Cl$_2$, 6.65 g/100 mL); $^1$H-NMR (CDCl$_3$): δ 1.60–1.80 (m, 2 H), 1.85–1.95 (m, 2 H), 2.03–2.10 (m, 2 H), 2.28–2.33 (m, 2 H), 2.35 (s, 3 H), 2.48–2.50 (m, 2 H), 3.20–3.40 (m, 2 H), 3.60 (s, 3 H), 3.68 (s, 3 H), 6.75 (s, 1 H), 7.20–7.34 (m, 5 H), 7.46 (d, J=8.8 Hz, 2 H), 7.60 (br s, 1 H, N H), 8.07 (d, J=8.8 Hz, 2 H), 8.78 (br t, 1 H, NH); Anal. Calcd. for C$_{30}$H$_{35}$N$_5$O$_8$.0.2 CH$_2$Cl$_2$.0.2 EtOAc: C, 59.27; H, 5.94; N, 11.15. Found: C, 59.07; H, 5.76; N, 10.99.

c. (-)-1-{N-[3-(4-Methoxycarbonyl-4-phenylpiperidin-1-yl)propyl]}carboxamido-5-methoxycarbonyl-4-methyl6-(4-nitrophenyl)-2-oxo-1,2,3,6-tetrahydropyrimidine.

A solution of (-)-1,6-dihydro-2-methoxy-5-methoxycarbonyl-4-methyl-6-(4-nitrophenyl)-1-{N-[(2-phenyl)ethyl]}carboxamidopyrimidine (0.35 g, 0.774 mmol) and 1,8-diazabicyclo[5.4.0]-unde-7-ene (DBU) (0.117 g, 0.774 mmol) in CH$_2$Cl$_2$ (10 mL) was stirred and refluxed for 8 hours and the solvent evaporated. The product was purified by column chromatography using 30% EtOAc in hexane as the eluent. The product, (-)-1,6-dihydro-5-methoxycarbonyl-2-methoxy-4-methyl-6-(4-nitrophenyl) pyrimidine, was found to be a mixture of the amine-imine tautomers (0.170 g, 72%). To a well-stirred solution of (-)-1,6-dihydro-5-methoxycarbonyl-2-methoxy-4-methyl-6-(4-nitrophenyl)pyrimidine (0.152 g, 0.5 mmol) and pyridine (0.5 mL) in CH$_2$Cl$_2$ (10 mL) at 0–5° C., 4-nitrophenyl chloroformate (0.121 g, 0.6 mmol) was added in 5 min and the mixture was allowed to warm to room temperature. After 2 hours, saturated aqueous NaHCO$_3$ solution (10 mL) was added and the stirring continued for 30 min. The two layers were separated, the CH$_2$Cl$_2$ layer was washed with saturated aqueous NaHCO$_3$ solution (3×5 mL), dried (Na$_2$SO$_4$), and the solvent evaporated. The residue was redissolved in THF (10 mL) and mixed with K$_2$CO$_3$ (0.165 g, 1.2 mmol). To this, a solution of 3-[4-methoxycarbonyl-4-phenylpiperidin-1-yl]propylamine (0.166 g, 0.6 mmol) in THF (5 mL) was added and the mixture was stirred for 2 hours. The solid was removed by filtration and the solution was cooled to 0–5° C. To this, 6N HCl (0.5 mL) was added and the stirring continued. After 3 hours, solvents were evaporated completely, the residue was redissolved in CH$_2$Cl$_2$ (20 mL), washed with 10% NaHCO$_3$ (4×5 mL), and dried (MgSO$_4$). Solvent was evaporated and the residue was purified by column chromatography using 1:1 hexane/EtOAc to 100% EtOAc as gradient eluent. The oily product was crystallized from hexane and EtOAc (0.19 g, 64%); m.p. 138–140° C.; [α]$_D$=–106 (CH$_2$Cl$_2$, 3.95 g/100 mL); $^1$H-NMR (CDCl$_3$): δ 1.60–1.80 (m, 2 H), 1.85–1.95 (m, 2 H), 2.03–2.10 (m, 2 H), 2.28–2.33 (m, 2 H), 2.35 (s, 3 H), 2.48–2.50 (m, 2 H), 3.20–3.40 (m, 2 H), 3.60 (s, 3 H), 3.68 (s, 3 H), 6.75 (s, 1 H), 7.20–7.34 (m, 6 H), 7.46 (d, J=8.8 Hz, 2 H), 8.07 (d, J=8.8 Hz, 2 H), 8.78 (br t, 1 H, NH) ; Anal. Calcd. for C$_{30}$H$_{35}$N$_5$O$_8$.0.4 CH$_2$Cl$_2$: C, 58.18; H, 5.75; N, 11.16. Found: C, 58.25; H, 5.67; N, 10.98.

EXAMPLE 15

1-{N-[3-(4-Ethoxycarbonyl-4-phenylpiperidin-1-yl) propyl]}carboxamido-5-methoxycarbonyl-4-methyl6-(4-nitrophenyl)-2-oxo-1,2,3,6-tetrahydropyrimidine.

To a stirred mixture of 1,6-dihydro-2-methoxy-5-methoxycarbonyl-4-methyl-6-(4-nitrophenyl)-1-[(4-nitrophenyloxy)carbonyl]pyrimidine (0.235 g, 0.5 mmol), K$_2$CO$_3$ (0.138 g, 1 mmol) in anhydrous THF (10 mL) at room temperature under argon atmosphere, a solution of 3-[4-ethoxycarbonyl-4-phenylpiperidin-1-yl]propylamine (0.174 g, 0.6 mmol, 1.2 eq) in THF (5 mL) was added and the stirring was continued for 4.5 h. The solid was removed by filtration and the solution was cooled to 0–5° C. To this, 6N HCl (0.5 mL) was added and the stirring continued. After 1 hour, solvents were evaporated completely, the residue was redissolved in CH$_2$Cl$_2$ (20 mL), washed with 1N NaHCO$_3$ (2×10 mL), and dried (MgSO$_4$). Solvent was evaporated and the residue was purified by column chromatography using 1:1 hexane/EtOAc to 100% EtOAc as gradient eluent. The oily product was crystallized from hexane and EtOAc (0.182 g, 60%); m.p. 79–80° C.; $^1$H-NMR (CDCl$_3$): δ 1.13 (t, J=7 Hz, 3 H), 1.62–1.78 (m, 2 H), 1.87–2.0 (m, 2 H), 2.06–2.18 (m, 2 H), 2.2–2.31 (m, 2 H), 2.37(s, 3 H), 2.50–2.55 (m, 2 H), 2.72–2.80 (m, 2 H), 3.25–3.40 (m, 2 H), 3.68 (s, 3 H), 4.07 (q, J=7 Hz, 2 H), 6.75 (s, 1 H), 7.18–7.36 (m, 6 H), 7.48 (d, J=8.7 Hz, 2 H), 8.11 (d, J=8.7 Hz, 2 H), 8.79 (br t, 1 H, NH); Anal. Calcd. for C$_{31}$H$_{37}$N$_5$O$_8$.0.5 C$_6$H$_{12}$.1.25 H$_2$O: C, 62.71; H, 7.06; N, 11.55. Found: C, 62.90; H, 7.20; N, 11.33.

EXAMPLE 16

5-Benzyloxycarbonyl-1-{N-[3-(4-methoxycarbonyl-4-phenylpiperidin-1-yl)propyl]}carboxamido-4-methyl-6-(3,4-methylenedioxyphenyl)-2-oxo-1,2,3, 6-tetrahydropyrimidine.

a. Benzyl 2-{(3,4-methylenedioxyphenyl)methylene}-3-oxobutyrate.

A mixture of 3,4-methylenedioxybenzaldehyde (15.013 g, 0.1 mol), benzyl acetoacetate (20.18 g, 0.105 mol), piperidine (0.41 g, 476 mL, 4.8 mmol), and acetic acid (0.288 g, 274 mL, 4.8 mmol) in 2-propanol (500 mL) was stirred at room temperature for 48 hours. The white solid, benzyl 2-{(3,4-methylenedioxyphenyl)methylene}-3-oxobutyrate, formed was filtered, washed with 2-propanol (2×50 mL) and dried (29.84 g, 92%); m.p. 137–138° C.

b. 5-Benzyloxycarbonyl-1,6-dihydro-2-methoxy-4-methyl-6-(3,4-methylenedioxyphenyl)pyrimidine.

A mixture of benzyl 2-{(3,4-methylenedioxyphenyl)methylene}-3-oxobutyrate (16.266 g, 0.05 mol), O-methylisourea hydrogen sulfate (10.32 g, 0.06 mol), and $NaHCO_3$ (8.4 g, 0.1 mol) in EtOH (400 mL) was stirred and heated at 85–90° C. for 48 h. The solid was removed by filtration and ethanol was evaporated from the filtrate. The residue was redissolved in EtOAc (300 mL), washed with water (2×100 mL), dried ($Na_2SO_4$), and the solvent evaporated. The crude product was purified by flash column chromatography on silica gel using 10% through 30% EtOAc in hexane as the gradient eluent, to leave the product as a viscous oil (11.8 g, 62%). The $^1$H-NMR analysis of the product showed it to be a 1:1 mixture of the amine/imine tautomers and was used as such in the next step.

c. 5-Benzyloxycarbonyl-1,6-dihydro-2-methoxy-4-methyl-6-(3,4-methylenedioxyphenyl)-1-[(4-nitrophenyloxy)carbonyl]pyrimidine.

To a well-stirred solution of 5-benzyloxycarbonyl-1,6-dihydro-2-methoxy-4-methyl-6-(3,4-methylenedioxyphenyl)pyrimidine (10.0 g, 0.0263) and pyridine (5 mL) in $CH_2Cl_2$ (500 mL) at 0–5° C., 4-nitrophenyl chloroformate (7.56 g, 0.038 mol) was added in 5 min and the mixture was allowed to warm to room temperature. After 16 hours, saturated aqueous $NaHCO_3$ solution (100 mL) was added and the stirring continued for 30 min. The two layers were separated, the $CH_2Cl_2$ layer was washed with saturated aqueous $NaHCO_3$ solution (3×50 mL), dried ($Na_2SO_4$), and the solvent evaporated. The residue on trituration with isopropyl ether gave the product as white crystals (12.8 g, 89%); m.p. 146–147° C.; $^1$H-NMR ($CDCl_3$): δ 2.46 (s, 3 H), 3.93 (s, 3 H), 5.19, 5.92 (AB q, J=12.6 Hz, 2 H), 5. 92 (s, 2 H), 6.22 (s, 1 H), 6.68–6.78 (m, 3 H), 7.15–7.29 (m, 5 H), 7.30 (d, J=9.1 Hz, 2 H), 8.22 (d, J=9.1 Hz, 2 H); Anal. Calcd. for $C_{28}H_{23}N_3O_9 \cdot 0.25\ H_2O \cdot 0.25\ CH_2Cl_2$: C, 59.40; H, 4.23; N, 7.36. Found: C, 59.42; H, 4.07; N, 7.30.

d. 5-Benzyloxycarbonyl-1-{N-[3-(4-methoxycarbonyl-4-phenylpiperidin-1-yl)propyl]}carboxamido-4-methyl-6-(3,4-methylenedioxyphenyl)-2-oxo-1,2,3,6-tetrahydropyrimidine.

To a stirred mixture of 5-benzyloxycarbonyl-1,6-dihydro-2-methoxy-4-methyl-6-(3,4-methylenedioxyphenyl)-1[(4-nitrophenyloxy)carbonyl]pyrimidine (1.091 g, 2 mmol), $K_2CO_3$ (0.552 g, 4 mmol) in anhydrous THF (20 mL) at room temperature under argon atmosphere, a solution of 3-[4-methoxycarbonyl-4-phenylpiperidin-1-yl]propylamine (0.663 g, 2.4 mmol, 1.2 eq) in THF (10 mL) was added and the stirring was continued for 2 hours. The solid was removed by filtration and the solution was cooled to 0–5° C. To this, 6N HCl (2 mL) was added and the stirring continued. After 3 hours, the solvent was evaporated completely, the residue was redissolved in $CH_2Cl_2$ (20 mL), washed with 10% $NaHCO_3$ (2×10 mL), and dried ($MgSO_4$). Solvent was evaporated and the residue was purified by column chromatography using 1:1 hexane/EtOAc to 100% EtOAc as gradient eluent, to afford the pure product as a white foam (0.55 g, 86%); m.p. 100–102° C.; $^1$H-NMR ($CDCl_3$): δ 1.64–1.80 (m, 2 H), 1.80–1.99 (m, 2 H), 2.0–2.09 (m, 2 H), 2.24–2.29 (m, 2 H), 2.33 (s, 3 H), 2.48–2.50 (m, 2 H), 2.76–2.83 (m, 2 H), 3.21–3.37 (m, 2 H), 3.60 (s, 3 H), 5.02, 5.18 (AB q, J=12.5 Hz, 2 H), 5.88 (s, 2 H), 6.61–6.78 (m, 3 H), 6.80 (s, 1 H), 7.14–7.39 (m, 11 H), 8.75 (br t, 1 H, NH) ; Anal. Calcd. for $C_{37}H_{40}N_4O_8 \cdot 0.3\ H_2O$: C, 65.92; H, 6.07; N, 8.31. Found: C, 65.95; H, 6.00; N, 8.18.

EXAMPLE 17

5-Methoxycarbonyl-1-{N-[3-(4-methoxycarbonyl-4-phenylpiperidin-1-yl)propyl]}carboxamido-4-methyl- 6-3,4-methylenedioxyphenyl)-2-oxo-1,2,3, 6-tetrahydropyrimidine.

To a stirred solution of 5-benzyloxycarbonyl-1-{N-[3-(4-methoxycarbonyl-4-phenylpiperidin-1-yl)propyl]}carboxamido-4-methyl-6-(3,4-methylenedioxyphenyl)-2-oxo-1,2,3,6-tetrahydropyrimidine (0.320 g, 0.48 mmol) in methanol (20 mL) and HCOOH (1 mL) at 0–5° C., 10% Pd-C (0.26 g) was added in portions and the cooling bath was removed. TLC analysis of the reaction mixture at frequent intervals showed the completion of the reaction after 2 hours. The catalyst was removed by filtration and the solvent was evaporated to leave 1-{N-[3-(4-methoxycarbonyl-4-phenylpiperidin-1-yl)propyl]}carboxamido-4-methyl-6-3,4-methylenedioxyphenyl)-2-oxo-1,2,3,6-tetrahydropyrimidine-5-carboxylic acid as a white solid (0.275 g, 99%). The product was used in the next step without any further purification and characterization. A mixture of 1-{N-[3-(4-methoxycarbonyl-4-phenylpiperidin-1-yl)propyl]}carboxamido-4-methyl-6-(3,4-methylenedioxyphenyl)-2-oxo-1,2,3,6-tetrahydropyrimidine-5-carboxylicacid (0.2 g, 0.346 mmol), 1-(3-dimethylaminopropyl)-3-ethylcarbodiimide hydrochloride (0.382 g, 2 mmol), and 4-(N,N-dimethylamino)pyridine (0.488 g, 4 mmol), in methanol (20 mL) was stirred and refluxed for 5 h and the solvent evaporated. The residue was redissolved in $CH_2Cl_2$ (15 mL), washed with saturated aqueous ammonium chloride solution (3×10 mL), and dried ($Na_2SO_4$). Evaporation of the solvent left the pure product as white powder (0.202 g, 99%); m.p. 139–141° C.; $^1$H-NMR ($CDCl_3$): δ 1.62–1.80 (m, 2 H), 1.95–2.20 (m, 4 H), 2.35 (s, 3 H), 2.30–2.55 (m, 4 H), 2.76–2.90 (m, 2 H), 3.21–3.40 (m, 2 H), 3.61 (s, 3 H), 3.67 (s, 3 H), 5.89 (s, 2 H), 6.61–6.82 (m, 3 H), 6.63 (s, 1 H), 7.21–7.35 (m, 6 H), 8.79 (br t, 1 H, NH); Anal. Calcd. for $C_{31}H_{36}N_4O_8 \cdot 0.3$ EtOAc: C, 62.47; H, 6.25; N, 9.05. Found: C, 62.64; H, 6.25; N, 8.87.

EXAMPLE 18

5-(2-Cyanoethoxycarbonyl)-4-ethyl-1,6-dihydro-1-{N-[3-(4-methoxycarbonyl-4-phenylpiperidin-1-yl)propyl]}carboxamido-2-methoxy-6-(4-nitrophenyl)pyrimidine.

a. 2-Cyanoethyl 3-{(4-nitrophenyl)methylene}-4-oxopentanoate.

A mixture of ethyl propionylacetate (25 g, 0.173 mol) and 3-hydroxypropionitrile (18.48 g, 0.26 mol) was stirred and heated at 200–205° C. for 2 hours and the ethanol formed was removed by distillation. The residue was subjected to high vacuum distillation and the fraction distilling at 120–125° C. at 0.4 mm Hg was collected to get 2-cyanoethyl propionylacetate (21.5 g, 73.4%). A mixture of 4-nitrobenzaldehyde (14.46 g, 0.957 mol), 2-cyanoethyl propionylacetate (17.0 g, 0.1005 mol), piperidine (0.41 g, 476 mL, 4.8 mmol), and acetic acid (0.288 g, 274 mL, 4.8 mmol) in 2-propanol (400 mL) was stirred at room temperature for 24 h. The white solid, 2-cyanoethyl 3-{(4-nitrophenyl)methylene}-4-oxopentanoate, was filtered, washed with 2-propanol (2×50 mL) dried and used without further purification (Yield: 28.34 g, 97%); m.p. 98–100° C.

b. 5-(2-Cyanoethoxycarbonyl)-1,6-dihydro-2-methoxy-4-ethyl-6-(4-nitrophenyl)pyrimidine.

A mixture of 2-cyanoethyl 3-{(4-nitrophenyl) methylene}-4-oxopentanoate (5.00 g, 16.54 mmol), O-methylisourea hydrogen sulfate (3.422 g, 19.85 mmol), and NaHCO$_3$ (2.78 g, 33.08 mol) in EtOH (70 mL) was stirred and heated at 85–90° C. for 5 hours. The solid was removed by filtration and ethanol was evaporated from the filtrate. The residue was redissolved in EtOAc (300 mL), washed with water (2×100 mL), dried (Na$_2$SO$_4$), and the solvent evaporated. The crude product was purified by flash column chromatography on silica gel using CHCl$_3$/methanol (30:1) as the eluent, to leave the product as a white solid (2.95 g, 50%). The $^1$H-NMR analysis of the product showed it to be a 5:1 mixture of the amine/imine tautomers and was used as such in the next step.

C. 5-(2-Cyanoethoxycarbonyl)-4-ethyl-1,6-dihydro-2-methoxy-6-(4-nitrophenyl)-1-[(4-nitrophenyloxy)carbonyl]pyrimidine.

To a well-stirred solution of 5-(2-cyanoethoxycarbonyl)-4-ethyl-1,6-dihydro-2-methoxy-6-(4-nitrophenyl)pyrimidine (2.64 g, 7.36 mmol) and pyridine (1.19 mL, 14.72 mmol) in CH$_2$Cl$_2$ (100 mL) at 0–5° C., 4-nitrophenyl chloroformate (1.485 g, 7.36 mmol) was added in 5 min and the mixture was allowed to warm to room temperature. After 16 h, saturated aqueous NaHCO$_3$ solution (25 mL) was added and the stirring continued for 30 min. The two layers were separated, the CH$_2$Cl$_2$ layer was washed with saturated aqueous NaHCO$_3$ solution (3×50 mL), dried (Na$_2$SO$_4$), and the solvent evaporated. The crude product was purified by flash column chromatography on silica gel using CHCl$_3$/EtOAc (25:1) as the eluent to give the product as a viscous oil (1.70 g, 44%); $^1$H-NMR (CDCl$_3$): δ1.24 (t, J=7 Hz, 3 H), 2.61–2.68 (m, 2 H), 2.88–2.92 (m, 2 H), 3.97 (s, 3 H), 4.32 (t, J=7 Hz, 2 H), 6.34 (s, 1 H), 7.37 (d, J=9.2 Hz, 2 H), 7.50 (d, J=8.7 Hz, 2 H), 8.18 (d, J=8.7 Hz, 2 H), 8.28 (d, J=9.2 Hz, 2 H).

d. 5-(2-Cyanoethoxycarbonyl)-4-ethyl-1,6-dihydro-1-{N-[3-(4-methoxycarbonyl-4-phenylpiperidin-1-yl)propyl]}carboxamido-2-methoxy-6-(4-nitrophenyl)pyrimidine.

To a stirred mixture of 5-(2-cyanoethoxycarbonyl)-4-ethyl-1,6-dihydro-2-methoxy-6-(4-nitrophenyl)-1-[(4-nitrophenyloxy)carbonyl]pyrimidine (0.940 g, 2 mmol) and K$_2$CO3 (0.552 g, 4 mmol) in anhydrous THF (20 mL) at room temperature under argon atmosphere, a solution of 3-[4-methoxycarbonyl-4-phenylpiperidin-1-yl]propylamine (0.882 g, 3 mmol, 1.5 eq) in THF (5 mL) was added and the stirring was continued for 1 h. Solvent was evaporated from the reaction mixture, the residue was redissolved in CH$_2$Cl$_2$ (50 mL), washed with 5% NaHCO$_3$ (3×25 mL), brine (50 mL), and dried (MgSO$_4$). Solvent was evaporated and the residue was purified by flash chromatography on silica gel using 10% methanol in EtOAc as the eluent to give the desired product as an oil, which on trituration with hexane and drops of EtOAc became a white powder (1.71 g, 80%); m.p. 62–63° C.; $^1$H-NMR (CDCl$_3$): δ 1.16 (t, J=7.5 Hz, 3 H), 1.62–1.78 (m, 2 H), 1.80–1.84 (m, 2 H), 2.06–2.18 (m, 2 H), 2.28–2.36 (m, 2 H), 2.50–2.53 (m, 4 H), 2.58–2.63 (m, 2 H), 2.70–2.84 (m, 4 H), 3.25–3.40 (m, 2 H), 3.61 (s, 3 H), 3.92 (s, 3 H), 4.26 (m, 2 H), 6.66 (s, 1 H), 6.82 (br t, 1 H, NH), 7.22–7.33 (m, 6 H), 7.43 (d, J=7.8 Hz, 2 H), 8.10 (d, J=7.8 Hz, 2 H); Anal. Calcd. for C$_{34}$H$_{40}$N$_6$O$_8$.0.1 C$_6$H$_{12}$.0.5 H$_2$O: C, 61.44; H, 6.27; N, 12.93. Found: C, 61.44; H, 6.27; N, 12.11.

EXAMPLE 19

(+)-5-Carboxamido-4-ethyl-1-{N-[3-(4-methoxycarbonyl-4-phenylpiperidin-1-yl)propyl]}carboxamido-6-(4-nitrophenyl)-2-oxo-1,2,3,6-tetrhydropyrimidine (Scheme 4).

a. 2-Cyanoethyl 3-{(4-nitrophenyl)methylene}-4-oxopentanoate.

A mixture of ethyl propionylacetate (25 g, 0.173 mol) and 3-hydroxypropionitrile (18.48 g, 0.26 mol) was stirred and heated at 200–205° C. for 2 h and the ethanol formed was removed by distillation. The residue was subjected to high vacuum distillation and the fraction distilling at 120–125° C. at 0.4 mm of Hg was collected to get 2-cyanoethyl propionylacetate (21.5 g, 73.4%).

A mixture of 4-nitrobenzaldehyde (14.46 g, 0.957 mol), 2-cyanoethyl propionylacetate (17.0 g, 0.1005 mol), piperidine (0.41 g, 476 mL, 4.8 mmol), and acetic acid (0.288 g, 274 mL, 4.8 mmol) in 2-propanol (400 mL) was stirred at room temperature for 24 h. The white solid, 2-cyanoethyl 3-{(4-nitrophenyl)methylene}-4-oxopentanoate, formed was filtered, washed with 2-propanol (2×50 mL) and dried (28.34 g, 97%); m.p. 98–100° C.

b. 5-(2-Cyanoethoxycarbonyl)-1,6-dihydro-2-methoxy-4-ethyl-6-(4-nitrophenyl)pyrimidine.

A mixture of 2-cyanoethyl 3-{(4-nitrophenyl) methylene}-4-oxopentanoate (5.00 g, 16.54 mmol), O-methylisourea hydrogen sulfate (3.422 g, 19.85 mmol), and NaHCO$_3$ (2.78 g, 33.08 mol) in EtOH (70 mL) was stirred and heated at 85–90° C. for 5 h. The solid was removed by filtration and ethanol was evaporated from the filtrate. The residue was redissolved in EtOAc (300 mL), washed with water (2×100 mL), dried (Na$_2$SO$_4$), and the solvent evaporated. The crude product was purified by flash column chromatography on silica gel using CHCl$_3$/methanol (30:1) as the eluent, to leave the product as a white solid (2.95 g, 50%). The $^1$H-NMR analysis of the product showed it to be a 5:1 mixture of the amine/imine tautomers and was used as such in the next step.

c. 5-(2-Cyanoethoxycarbonyl)-4-ethyl-1,6-dihydro-2-methoxy-6-(4-nitrophenyl)-1-[(4-nitrocarbonyl]pyrimidine.

To a well-stirred solution of 5-(2-cyanoethoxycarbonyl)-4-ethyl-1,6-dihydro-2-methoxy-6-(4-nitrophenyl)pyrimidine (2.64 g, 7.36 mmol) and pyridine (1.19 mL, 14.72 mmol) in CH$_2$Cl$_2$ (100 mL) at 0–5° C., 4-nitrophenyl chloroformate (1.485 g, 7.36 mmol) was added in 5 min and the mixture was allowed to warm to room temperature. After 16 h, saturated aqueous NaHCO$_3$ solution (25 mL) was added and the stirring continued for 30 min. The two layers were separated, the CH$_2$Cl$_2$ layer was washed with saturated aqueous NaHCO$_3$ solution (3×50 mL), dried (Na$_2$SO$_4$), and the solvent evaporated. The crude product was purified by flash column chromatography on silica gel using CHCl$_3$/EtOAc (25:1) as the eluent to give the product as a viscous oil (1.70 g, 44%); $^1$H-NMR (CDCl$_3$): δ 1.24 (t, J=7 Hz, 3 H), 2.61–2.68 (m, 2 H), 2.88–2.92 (m, 2 H), 3.97 (s, 3 H), 4.32 (t, J=7 Hz, 2 H), 6.34 (s, 1 H), 7.37 (d, J=9.2 Hz, 2 H), 7.50 (d, J=8.7 Hz, 2 H), 8.18 (d, J=8.7 Hz, 2 H), 8.28 (d, J=9.2 Hz, 2 H).

d. 5-(2-Cyanoethoxycarbonyl)-4-ethyl-1,6-dihydro-2-methoxy-6-(4-nitrophenyl)-1-{N-[(2phenyl)ethyl]}carboxamidopyrimidine.

To a stirred solution of 5-(2-cyanoethoxycarbonyl)-4-ethyl-1,6-dihydro-2-methoxy-6(4-nitrophenyl)-1-[(4-nitrophenyloxy)carbonyl]pyrimidine (17.5 g, 33.43 mmol) in anhydrous THF (200 mL) at room temperature under argon atmosphere, (R)-(+)-a-methylbenzylamine (4.86 g, 40.11 mmol) was added and the stirring was continued for 16 h. Solvent was evaporated from the reaction mixture and the residue was purified by flash chromatography on silica gel using toluene/EtOAc (20:3) as the eluent. The first major product to elute was (+)-5-(2-cyanoethoxycarbonyl)-4-ethyl-1,6-dihydro-2-methoxy-6-(4-nitrophenyl)-1-{N-[(2-phenyl)ethyl]}carboxamidopyrimidine and obtained as a viscous oil (6.11 g, 36.2%); $[\alpha]_D$=+299.5 (c=1.95, CHCl$_3$); $^1$H-NMR (CDCl$_3$): δ 1.18 (t, J=7 Hz, 3 H), 1.47 (d, J=7 Hz, 3 H), 2.61 (t, 2 H), 2.7–2.92 (m, 2 H), 3.98 (s, 3 H), 4.20–4.32 (m, 2 H), 4.96 (quint, J=6.5 Hz, 2 H), 6.66 (s, 1 H), 6.82 (d, J=6.8 Hz, 1 H, NH), 7.22–7.36 (m, 5 H), 7.45 (d, J=8.6 Hz, 2 H), 8.11 (d, J=8.6 Hz, 2 H). The second major compound to elute was (−)-5-(2-cyanoethoxycarbonyl)-4-ethyl-1,6-dihydro-2-methoxy-6-(4-nitrophenyl)-1-{N-[(2-pheny)ethyl]}carboxamidopyrimidine and obtained as a viscous oil (5.92 g, 35%); $[\alpha]_D$=−105.1 (c=3.9, CHCl$_3$) ; $^1$H-NMR (CDCl$_3$): 67 1.20 (t, J=7 Hz, 3 H), 1.48 (d, J=7 Hz, 3 H), 2.62 (t, 2 H), 2.82 (q, 2 H), 3.94 (s, 3 H), 4.20–4.32 (m, 2 H), 4.96 (quint, J=6.5 Hz, 2 H), 6.69 (s, 1 H), 6.84 (d, J=6.8 Hz, 1 H, NH), 7.22–7.36 (m, 5 H), 7.39 (d, J=8.6 Hz, 2 H), 8.06 (d, J=8.6 Hz, 2 H).

e. (+)-5-(2-Cyanoethoxycarbonyl)-1,6-dihydro-2-methoxy-4-ethyl-6-(4-nitrophenyl)pyrimidine.

To a stirred solution of (+)-5-(2-cyanoethoxycarbonyl)-4-ethyl-1,6-dihydro-2-methoxy-6-(4-nitrophenyl)-1-{N-[(2-phenyl)ethyl]}carboxamidopyrimidine (2.62 g, 5.182 mmol) in toluene (40 mL) was added 1,8-diazabicyclo[5,4,0]-undec-7-ene (0.237,1.55 mmol) at room temperature and the resulting solution was heated at 90° C. for 3.5 minutes. The solvent was evaporated and the residue was purified by flash column chromatography on silica gel using 9:1 CHCl$_3$/EtOAc as the eluent, to give 1.32 g (71%)of (+)-5-(2-cyanoethoxycarbonyl)-1,6-dihydro-2-methoxy-4-ethyl-6-(4-nitrophenyl)pyrimidine; $[\alpha]_D$=+4.0 (c=3.25, CHCl$_3$).

f.(+)-5-(2-Cyanoethoxycarbonyl)-4-ethyl-1,6-dihydro-2-methoxy-6-(4-nitrophenyl)-1-[(4-nitrophenyloxy)carbonyl]pyrimidine.

To a well-stirred solution of 5-(2-cyanoethoxycarbonyl)-4-ethyl-i,6-dihydro-2-methoxy-6-(4-nitrophenyl)pyrimidine (1.62 g, 4.52 mmol) and 4-(N,N-dimethylamino) pyridine (0.663 g, 5.43 mmol) in CH$_2$Cl$_2$ (50 mL) at 0–5° C., 4-nitrophenyl chloroformate (1.094 g, 5.43 mmol) was added in 5 minutes and the mixture was allowed to warm to room temperature. After 3 hours the solvent evaporated and the product was purified by flash column chromatography on silica gel using CHCl$_3$/EtOAc (25:1) as the eluent to give the product as a white solid (2.25 g, 95%); $^1$H-NMR (CDCl$_3$): δ 1.24 (t, J=7 Hz, 3 H), 2.61–2.68 (m, 2 H), 2.88–2.92 (m, 2 H), 3.97 (s, 3 H), 4.32 (t, J=7 Hz, 2 H), 6.34 (s, 1 H), 7.37 (d, J=9.2 Hz, 2 H), 7.50 (d, J=8.7 Hz, 2 H), 8.18 (d, J=8.7 Hz, 2 H), 8.28 (d, J=9.2 Hz, 2 H); $[\alpha]_D$=+317.2 (c=3.9, CHCl$_3$)

g. (+)-5-(2-cyanoethoxycarbonyl)-4-ethyl-1-{N-[3-(4-methoxycarbonyl-4-phenylpiperidin-1-yl)propyl]}carboxamido-6-(4-nitrophenyl)-2-oxo-1,2,3,6-tetrhydropyrimidine.

To a stirred mixture of (+)-5-(2-cyanoethoxycarbonyl)-4-ethyl-1,6-dihydro-2-methoxy-6-(4-nitrophenyl)-1-[(4-nitrophenyloxy)carbonyl]pyrimidine (3.60 g, 6.878 mmol) in anhydrous THF (100 mL) at room temperature under argon atmosphere, a solution of 3-[4-methoxycarbonyl-4-phenylpiperidin-1-yl]propylamine (2.47 g, 8.94 mmol, 1.3 eq) in THF (10 mL) was added and the stirring was continued for 12 hours. The mixture was cooled to 0° C. and aqueous 6N hydrochloric acid (10 mL). The mixture was allowed to warm to room temperature and the stirring was continued for 5 h. Solvent was evaporated from the reaction mixture, the residue was purified by flash chromatography on silica gel using ethyl acetate (800 mL) followed by chloroform-methanol-2M ammonia in methanol (90/8/4) as the eluent, to obtain the desired product as a white powder (4.40 g, 98.5%); $^1$H-NMR (CDCl$_3$): δ 1.23 (t, J=7.5 Hz, 3 H), 2.0–2.1 (m, 2 H), 2.40–2.95 (m, 12 H), 3.25–3.50 (m, 4 H), 3.65 (s, 3 H), 4.27–4.32 (m, 2 H), 6.64 (s, 1 H), 7.20–7.33 (m, 5 H), 7.49 (d, J=7.8 Hz, 2 H), 8.08 (d, J=7.8 Hz, 2 H), 8.70–8.90 (m, 2 H); $[\alpha]_{D=+}$112.1 (c=2.15, CHCl$_3$); This product was used in the next step without any additional analysis.

h. (+)-5-Carboxamido-4-ethyl-1-{N-[3-(4-methoxycarbonyl-4-phenylpiperidin-1-yl)propyl]}carboxamido-6-(4-nitrophenyl)-2-oxo-1,2,3,6-tetrhydropyrimidine.

To a stirred solution of 5-(2-cyanoethoxycarbonyl)-4-ethyl-1-{N-[3-(4-methoxycarbonyl-4-phenylpiperidin-1-yl)propyl]}carboxamido-6-(4-nitrophenyl)-2-oxo-1,2,3,6-tetrhydropyrimidine (4.40 g, 6.8 mmol) in acetone (50 mL) at 0° C., sodium hydroxide solution (1N, 27.2 mL, 4 eq.) was added drop wise and the stirring was continued until the disappearance of the starting material (1 hour). Most of the acetone from the mixture was evaporated under reduced pressure while keeping the temperature at 0° C. and the residue was adjusted to pH 7.0 by the addition of 1N hydrochloric acid. The white precipitate of (+)-4-ethyl-1-{N-[3-(4-methoxycarbonyl-4-phenylpiperidin-1-yl)propyl]}carboxamido-6-(4-nitrophenyl)-2-oxo-1,2,3,6-tetrhydropyrimidine-5-carboxylic acid formed was filtered and dried under vacuum (3.59 g, 89%). $^1$H-NMR (CDCl$_3$): δ 1.07 (t, J=7.5 Hz, 3 H), 1.55–1.70 (m, 2 H), 1.72–1.84 (m, 2 H), 1.84–2.15 (m, 2 H), 2.20–2.40 (m, 4 H), 2.70–2.90 (m, 2 H), 3.10–3.40 (m, 4 H), 3.51 (s, 3 H), 6.54 (s, 1 H), 7.18–7.38 (m, 6 H), 7.41 (d, J=7.8 Hz, 2 H), 8.15 (d, J=7.8 Hz, 2 H), 8.79 (br t, 1 H, N H), 10.05 (br S, 1 H, COO<u>H</u>); This product was used in the next step without any additional analysis.

A mixture of (+)-4-ethyl-1-{N-[3-(4-methoxycarbonyl-4-phenylpiperidin-1-yl)propyl]}carboxamido-6-(4-nitrophenyl)-2-oxo-1,2,3,6-tetrhydropyrimidine-5-carboxylic acid (0.350 g, 0.59 mmol), 1-(3-dimethylaminopropyl)-3-ethylcarbodiimide hydrochloride (0.2264 g, 1.181 mmol, 2 eq.), and 4-(N,N-dimethylamino) pyridine (0.1443 g, 1.181 mmol, 2 eq) in anhydrous dichloromethane was stirred at room temperature for 2 h. To this, 40% aqueous ammonia (0.6 mL) was added and the stirring was continued for 12 h. The mixture was diluted with 100 mL of dichloromethane and washed with saturated aqueous ammonium chloride solution (3×20 mL). Solvent was evaporated from the dried (magnesium sulfate) dichloromethane solution and the residue was purified by column chromatography on silica gel using chloroform-methanol-2M ammonia in methanol (500/16/8) as the eluent, to obtain the desired product as a white powder (0.24 g, 69%); m.p. 107–109° C.; $^1$H-NMR (CDCl$_3$): δ 1.20 (t, J=7.5 Hz, 3 H), 1.66–1.72 (m, 2 H), 1.79–2.00 (m, 3 H), 2.00–2.20 (m, 2 H), 2.29–2.35 (m, 2 H), 2.42–2.60 (m, 2 H), 2.62–2.82 (m, 3 H), 3.20–3.40 (m, 2 H), 3.60 (s, 3 H), 5.70 (br m, 2 H, N<u>H</u>$_2$), 6.59 (s, 1 H), 7.20–7.39 (m, 6 H), 7.52 (d, J=7.8 Hz, 2 H), 8.13 (d, J=7.8 Hz, 2 H), 8.82 (t, 1 H) ; $[\alpha]_D$=+115.71 (c=1.4, CHCl$_3$) ; Anal. Calcd. for C$_{30}$H$_{36}$N$_6$O$_7$.0.8 H$_2$O: C, 59.36; H, 6.24; N, 13.84. Found: C, 59.47; H, 6.07; N, 13.64.

EXAMPLE 20

(+)-5-Carboxamido-6-(3,4-difluorophenyl)-4-ethyl-1-{N-[3-(4-methoxycarbonyl-4-phenylpiperidin-1-)propyl]}carboxamido-2-oxo-1,2,3,6-tetrhydropyrimidine (Scheme5).

a. Benzyl 3-[(3,4-difluorophenyl)methylene]-4-oxopentanoate.

A solution of benzyl propionylacetate (36.3 g, 176 mmol), 3,4-difluorobenzaldehyde (25.0 g, 176 mmol), piperidine (0.86 mL, 9.0 mmol) and acetic acid (0.49 mL, 9.0 mmol) were refluxed with removal of water using Dean-Stark apparatus for 5h. The solvent was removed in vacuo and the residue was dissolved in EtOAc. It was washed with water (100 mL) followed by brine (100 mL) and dried over anhydrous $Na_2SO_4$. Solvent was evaporated to get pale yellow syrup (60.2 g). It was used in the next step without further purification.

b. 5-(Benzyloxycarbonyl)-1,6-dihydro-2-methoxy-4-ethyl-6-(3,4-difluorophenyl)pyrimidine.

A suspension of benzyl 3-[(3,4-difluorophenyl) methylene]-4-oxopentanoate (16.0 g, 48.0 mmol), O-methylisourea hydrogen sulfate (16.65 g, 97.02 mmol), $NaHCO_3$ (16.3 g, 130.2 mmol) in DMF (190 mL) was stirred at 70° C. for 20h. After cooling to room temperature, the mixture was filtered and the filtrate was diluted with EtOAc (300 mL) and then washed with water (4×100 mL), brine (200 mL) and dried over $Na_2SO_4$. After removal of solvent, the residue was purified by column chromatography ($SiO_2$, EtOAc/Hexane, 10%–30%) to get 5-(benzyloxycarbonyl)-1,6-dihydro-2-methoxy-4-methyl-6-(3,4-difluorophenyl)pyrimidine as a colorless oil (10.6 g, 58%). The NMR analysis showed it to be a mixture of amine/imine tautomers and was used as is in the next step.

c. 5-(Benzyloxycarbonyl)-4-ethyl-1,6-dihydro-2-methoxy-6-(3,4-difluorophenyl)-1-[(4-nitrophenyloxy)carbonyl]pyrimidine.

To a well stirred solution of 5-(benzyloxy carbonyl)-1,6-dihydro-2-methoxy-4-ethyl-6-(3,4-difluorophenyl) pyrimidine (17.0 g, 44.04 mmol) and 4-dimethylaminopyridine (6.99 g, 57.25 mmol) in $CH_2Cl_2$ (200 mL) was added a powder of 4-nitrophenyl chloroformate 11.54 g, 57.25 mmol) at room temperature. The reaction mixture was stirred for 12 hours and then the solvent was removed in vacuo. The residue was purified by chromatography (SiO2, EtOAc/Hexane 10–30%) to get 5-(benzyloxycarbonyl)-4-ethyl-1,6-dihydro-2-methoxy-6-(3,4-difluorophenyl)-1-[(4-nitrophenyloxy)carbonyl] pyrimidine as a colorless viscous oil(12.6 g, 50%). $^1$H NMR ($CDCl_3$): δ 1.24 (t, J=7.2 Hz, 3H), 2.81–2.98 (m, 3H), 3.97 (s, 3H), 5.14 ($AB_q$, $δ_A$=5.08, $δ_B$=5.20, J=12.3 Hz, 2H), 6.28 (s, 3H), 7.03–7.29 (m, 8H), 7.35 (d, J=9.2 Hz, 2H), 8.26 (d, J=9.2 Hz, 2H).

d. 5-(Benzyloxycarbonyl)-4-ethyl-1,6-dihydro-1-{N-[2-phenyl)ethyl]}carboxamido-2-methoxy-6-(3,4-difluorophenyl)pyrimidine.

To a stirred mixture of 5-(benzyloxycarbonyl)-4-ethyl-1,6-dihydro-2-methoxy-6-(3,4-difluorophenyl)-1-[(4-nitrophenyloxy)carbonyl]pyrimidine (12.6 g, 22.86 mmol) in THF (150 mL) was added a solution of R-(+)-a-methyl benzylamine (3.53 mL, 27.44 mmol) at room temperature. The stirring was continued for 12 hours. Solvent was removed in vacuo. The yellow residue was dissolved in chloroform (200 mL) and was washed with 10% $K_2CO_3$ solution (2×30 mL). The organic layer was dried over $Na_2SO_4$, filtered and solvent was removed in vacuo. The resulting mixture of diastereomers was separated by column chromatography over silica gel with 9:1 Pet. ether:Ether to 4:1 Pet. ether:Ether. First major product to elute was (+)-5-(benzyloxycarbonyl)-4-ethyl-1,6-dihydro-1-{N-[2-phenyl) ethyl]}carboxamido-2-methoxy-6-(3,4-diflurophenyl) pyrimidine. Colorless oil, Rf=0.31(4:1 Pet ether:ether), wt.= 3.8 g (60%), $[α]_D$=+267.05 (c=0.76, $CHCl_3$)$^1$H NMR: δ 1.22 (t, J=7.5 Hz, 3H), 1.52 (d, J=6.9 Hz, 3H),2.88 (q, J=6.0 Hz, 2H), 3.99 (s, 3H), 4.99 (m, 1H), 5.09 ($AB_q$, $δ_A$=5.00, $δ_B$=5.19, J=12.6 Hz, 2H), 6.66 (s, 1H), 6.99–7.36 (m, 13H).; Second major product to elute was (−)-5-(benzyloxycarbonyl)-4-ethyl-1,6-dihydro-1-{N-[2-phenyl) ethyl]}carboxamido-2-methoxy-6-(3,4-difluorophenyl) pyrimidine. Colorless oil. Rf=0.22(4:1 Pet ether:ether), wt.= 3.2 g (51.2%), $[α]_D$=−146.89 (c=0.38, $CHCl_3$), $^1$H NMR: δ 1.22 (t, J=7.2 Hz, 3H), 1.49 (d, J=6.6 Hz, 3H),2.88 (q, J=6.0 Hz, 2H), 3.94 (s, 3H), 5.03 (m, 1H), 5.11 ($AB_q$, $δ_A$=5.02, $δ_B$=5.19, J=12.6 Hz, 2H), 6.68 (s, 1H), 6.91–7.34 (m, 13H).

e. (+)-5-(Benzyloxycarbonyl)-1,6-dihydro-2-methoxy-4-ethyl-6-(3,4-difluorophenyl)pyrimidine.

To a stirred solution of (+)-5-(benzyloxycarbonyl)-4-ethyl-1,6-dihydro-1-{N-[2-phenyl)ethyl]}carboxamido-2-methoxy-6-(3,4-difluorophenyl)pyrimidine (1.83 mmol, 1.0 g) in toluene (10 mL) was added 1,8-diazabicyclo[5,4,0]-undec-7-ene (0.81 mmol,0.12 mL) at room temperature and the resulting solution was heated to reflux for 5 h and then stirred for 12 h at room temperature. The solvent was evaporated and the residue was purified by flash column chromatography on silica gel with 3:1 EtOAc/Hexanes as the eluting system. 0.56 g of the (+)-5-(benzyloxycarbonyl)-1,6-dihydro-2-methoxy-4-ethyl-6-(3,4-difluorophenyl) pyrimidine was obtained (77%).

f. (+)-5-(Benzyloxycarbonyl)-4-ethyl-1,6-dihydro-2-methoxy-6-(3,4-difluorophenyl)-1-[(4-nitrophenyloxy) carbonyl]pyrimidine.

To a well stirred solution of (+)-5-(benzyloxycarbonyl)-1,6-dihydro-2-methoxy-4-ethyl-6-(3,4-difluorophenyl) pyrimidine (17.0 g, 44.04 mmol) and 4-dimethylaminopyridine (6.99 g, 57.25 mmol) in $CH_2Cl_2$ (200 mL) was added a powder of 4-nitrophenyl chloroformate 11.54 g, 57.25 mmol) at room temperature. The reaction mixture was stirred for 12 hours and then the solvent was removed in vacuo. The residue was purified by chromatography ($SiO_2$, EtOAc/Hexane 10–30%) to get (+)-5-(benzyloxycarbonyl) -4-ethyl-1,6-dihydro-2-methoxy-6-(3,4-difluorophenyl)-1-[(4-nitrophenyloxy)carbonyl] pyrimidine as a colorless viscous oil(19.3 g, 76%).

g. (+)-5-(Benzyloxycarbonyl)-6-(3,4-difluorophenyl)-4-ethyl-1-{N-[3-(4-methoxycarbonyl-4-phenylpiperidin-1-yl) propyl]}carboxamido-2-oxo-1,2,3,6-tetrhydropyrimidine. To a stirred mixture of (+)-5-(benzyloxycarbonyl)-4-ethyl1, 6-dihydro-2-methoxy-6-(3,4-difluorophenyl)-1-[(4-nitrophenyloxy)carbonyl]pyrimidine (0.55 g, 1.12 mmol) in THF (5 mL) was added a solution of 3-[4-methoxycarbonyl-4-phenylpiperidin-1-yl]propylamine (0.31 g, 1.12 mmol) in THF (5 mL) at room temperature. The stirring was continued for 12 hours. A solution of 10% HCl in water (2 mL) was added and stirred for 2 h. The solvent was then removed in vacuo and the residue was extracted with ethyl acetate (3×10 mL). It was washed with 10% aq. KOH solution, dried over $Na_2SO_4$ and solvent was removed in vacuo to obtain (+)-5-(benzyloxycarbonyl)-6-(3,4-difluorophenyl)-4-ethyl-1-{N-[3-(4-methoxycarbonyl-4-phenylpiperidin-1-yl)propyl] }carboxamido-2-oxo-1,2,3,6-tetrhydropyrimidine as a white foamy compound (0.73 g, 96.6%) the purity of which was characterized as its HCl salt. It was used in the next step without further purification. Anal. Calcd. for $C_{37}H_{41}ClF_2N_4O_6.0.5CHCl_3$: C, 58.43; H, 5.43; N, 7.27. Found: C, 58.11, H; 5.85; N, 7.64.

h. 6-(3,4-Difluorophenyl)-4-ethyl-1-{N-[3-(4-methoxycarbonyl-4-phenylpiperidin-1-yl)propyl] }carboxamido-1,2,3,6-tetrhydro-2-oxopyrimidine-5-carboxylic acid.

To a suspension of 10% Pd-C (0.14 g, 20% by wt.) in MeOH (3 mL) was added the solution of (+)-5-(benzyloxycarbonyl)-6-(3,4-difluorophenyl)-4-ethyl-1-{N-

[3-(4-methoxycarbonyl- 4-phenylpiperidin-1-yl)propyl]}carboxamido-2-oxo-1,2,3,6-tetrhydropyrimidine at room temperature with constant stirring. A balloon filled with $H_2$ was attached and the reaction mixture was stirred for 48 hours. The black suspension was filtered through a pad of celite and the filtrate was concentrated in vacuo. The residue was purified by column chromatography ($SiC_2$, 10% MeOH in EtOAc) to obtain (+)-6-(3,4-difluorophenyl)-4-ethyl-1-{N-[3-(4-methoxycarbonyl-4-phenylpiperidin-1-yl)propyl]}carboxamido-1,2,3,6-tetrhydro-2-oxopyrimidine-5-carboxylic acid as a white solid. M.P. 184–186° C.; $[\alpha]_D$=+142.2 (c=0.25, $CHCl_3$) The purity was checked by combustion analysis as a HCl salt. Anal. Calcd. for $C_{30}H_{35}ClF_2N_4O_6\cdot0.3CHCl_3$: C, 55.40; H, 5.42; N, 8.53. Found: C, 55.34; H; 5.80; N, 8.13.

i. (+)-5-Carboxamido-6-(3,4-difluorophenyl)-4-ethyl1-{N-[3-(4-methoxycarbonyl-4-phenylpiperidin-1-yl)propyl]}carboxamido-2-oxo-1,2,3,6-tetrhydropyrimidine.

To a solution of (+)-6-(3,4-difluorophenyl)-4-ethyl1-{N-[3-(4-methoxycarbonyl-4-phenylpiperidin-1-yl)propyl]}carboxamido-1,2,3,6-tetrhydro-2-oxopyrimidine-5-carboxylic acid (0.22 g, 0.375 mmol) in $CH_2Cl_2$ (3 mL) was added 4-N,N-dimethylamino pyridine (0.14 g, 1.12 mmol) and 1-(3-dimethylaminopropyl)-3-ethylcarbodiimide-hydrochloride (0.21 g, 1.12 mmol) under argon and the resulting solution was stirred at room temperature for 2h. Three drops of saturated $NH_4OH$ was then added and the solution was stirred for 48 h. The solution was washed with water (5 ml) and dried over $Na_2SO_4$. The solvent was removed in vacuo and the residue was purified by column chromatography ($SiC_2$, 10% MeOH in $CHCl_3$) to obtain 5-carboxamido-6-(3,4-difluorophenyl)-4-ethyl-1-{N-[3-(4-methoxycarbonyl-4-phenylpiperidin-1-yl)propyl]}carboxamido-2-oxo-1,2,3,6-tetrhydropyrimidine as a beige solid (0.1 g, 45w). Characterized as HCl salt. M.P. 136–138° C., $[\alpha]_D$=+111.44 (c=0.18, MeOH): δ 1.21 (t, J=7.5 Hz, 3H), 1.60–1.75 (m, 2H), 1.92–2.1 (m, 8H), 2.33 (t, J=6.6 Hz, 2H), 2.44–2.52 (m, 2H), 2.53–2.84 (m, 4H), 3.27–3.32 (m, 2H), 3.60 (s, 3H), 5.60 (br s,2H), 6.47 (s, 1H), 7.05–7.33 (m, 8H), 8.80 (br t, 1H), Anal. Calcd. for $C_{30}H_{35}ClF_2N_4O_6\cdot1.0$ $CHCl_3$: C, 50.35; H, 5.04; N, 9.47. Found: C, 50.40; H; 5.33; N, 9.13.

EXAMPLE 21

6-(3,4-Difluorophenyl)-5-methoxycarbonyl-4-methyl-2-oxo-1-{N-[4-(2-pyridyl)-piperidine-1-yl]propyl}carboxamido-1,2,3,6-tetrahydropyrimidine dihydrochloride (Scheme 7).

a. 1-Benzyl-4-cyano-4-(2-pyridyl)piperidine.

To a mixture of N,N-bis-(2-chloroethyl)benzylamine (E.Szarvasi, Eur. J. Med. Chem. Chim. Ther. 11(2), 115–124, 1976) (60 g, 22 mmol), 2-pyridylacetonitrile (2.51 ml, 22 mmol) and tetrabutylammonium hydrogen sulfate (0.26 g, 0.7 mmol) in toluene (10 ml), sodium hydroxide solution (2.43 g in 4.86 ml $H_2O$) was added over a 20 minute period. The reaction mixture was heated at 65° C. for 4 hours. The reaction mixture was cooled to room temperature, 10 ml of water was added and the solution partitioned between ethyl acetate (45 ml) and water. The organic layer was dried over sodium sulfate, filtered and concentrated. Purification of the crude product by column chromatography (hexane:EtOAc,2:3) gave 6.2 g (87%) of the title compound as a red solid; $^1$H-NMR ($CDCl_3$): δ 2.05 (d, J=13.1 Hz, 2 H), 2.30 (t, J=13.2 Hz, 2 H), 2.48 (t, J=13.2 Hz, 2 H), 2.97 (d, J=12.1 Hz, 2 H), 3.57 (s, 2 H), 7.19–7.27 (m, 6 H), 7.30 (d, J=7.6 Hz, 1 H), 7.60 (t, J=7.6 Hz, 1 H), 8.58 (d, J=4.6 Hz, 1 H).

b. 1-Benzyl-4-carboxamido-4-(2-pyridyl)piperidine.

To 1-benzyl-4-cyano-4-(2-pyridyl)piperidine (4.5 g, 14.3 mmol), 10 ml of conc.$H_2SO_4$ was added and the solution was stirred at room temperature for 24 hours. It was cooled to 0° C., diluted with ice pieces and poured into crushed ice. The mixture was then carefully neutralized with 50% NaOH solution. The reaction mixture was repeatedly extracted with chloroform (3×25 ml), dried over sodium sulfate, filtered and concentrated to give 4.5 g (95%)of the crude product which was used as such for the subsequent step; $^1$H-NMR ($CDCl_3$): δ 2.21–2.28 (m, 2 H), 2.47 (s, 6 H), 3.41 (s, 2 H), 5.23 (s, 1 H), 6.40 (s, 1 H), 7.12–7.29 (m, 6 H), 7.33 (d, J=7.6 Hz, 1 H), 7.63 (t, J=7.6 Hz, 1 H), 8.55 (d, J=4.6 Hz, 1 H).

c. 1-Benzyl-4-(2-pyridyl)-piperidine.

To 1-benzyl-4-carboxamido-4-(2-pyridyl)piperidine (4.5 g, 13.5 mmol) in anhydrous methanol (100 ml), HCl gas was bubbled through the solution at 0° C. for 15 minutes. The reaction mixture was then refluxed for 24 hours. It was cooled to room temperature, concentrated, neutralized with 50% NaOH and repeatedly extracted with chloroform (3×25 ml). The combined organic layer was then dried over sodium sulfate, filtered and concentrated. Flash chromatography (hexane:ethylacetate, 1:4) of the crude product yielded 1.72 g (50%) of the product as a syrup; $^1$H-NMR ($CDCl_3$); δ 1.8–1.94 (m, 4 H), 2.11 (t, J=11.4 Hz, 2 H), 2.70–2.72 (m, 1 H),3.02 (d, J=11.4 Hz, 2 H), 3.54 (s, 2 H), 7.07–7.36 (m, 7 H), 7.58 (t, J=7.6 Hz, 1 H), 8.52 (d, J=4.6 Hz, 1 H).

d. 3-[4-(2-Pyridyl)-piperidine-1-yl]propylamine (Scheme 6).

To 1-Benzyl-4-(2-pyridyl)-piperidine (3.26 g, 12.9 mmol) in dry methanol (25 ml), 10% palladium hydroxide (1.9 g) was added and the solution was hydrogenated at 200 psi for 24 hours. The solution was filtered over celite, concentrated to give 2.1 g (99%) of 4-(2-pyridyl)-piperidine which was used as such for the subsequent step. A mixture of 3-bromopropylamine hydrobromide (20 g, 91.3 mmol), potassium carbonate (37.85 g, 273.9 mmol) and di-tert-butyldicarbonate (21.90 g, 100 mmol) in methanol was stirred at room temperature for 24 hours. The reaction mixture was concentrated and partitioned between 250 ml EtOAc and 50 ml water, dried over sodium sulfate, filtered and concentrated. Purification of the crude product by column chromatography (Hexane: EtOAc, 4.5:0.5) gave 17.5 g (80%) of the product as a pale yellow oil. To a stirred solution of the 4-(2-pyridyl)-piperidine (1.86 g, 11.4 mmol) in dioxane (20 ml), N-(tert-butoxycarbonyl)-3-bromopropylamine (2.82 g, 11.4 mmol) and potassium carbonate (3.16 g, 22.9 mmol) were added and the solution refluxed for 24 hours. The reaction mixture was cooled to room temperature, concentrated and partitioned between 40 ml chloroform and 5 ml water. The organic layer was dried over sodium sulfate, filtered and concentrated. The crude product was purified by column chromatography (ethyl acetate: methanol, 4:1) to yield 1.86 g (49%) of the required product as a colorless oil; $^1$H-NMR ($CDCl_3$): δ 1.45 (s, 9 H),1.54–1.69 (m, 8 H), 2.21–2.68 (m, 2 H), 2.74–2.80 (m, 1 H), 3.02–3.22 (m, 4 H), 5.41 (s, 1H), 7.13–7.17 (m, 1 H), 7.33 (d, J=7.93 Hz, 1 H).7.63 (t, J=7.6 Hz, 1 H), 8.54 (d, J=4.6 Hz, 1 H). To N-(tert-butoxycarbonyl)-3-[4-(2-pyridyl)-piperidin-1-yl]propylamine (0.15g, 0.45 mmol) in 5 ml of dichloromethane, 1 ml of trifluoroacetic acid was added and the solution stirred at room temperature for 1 hour. The solution was concentrated, neutralized with 10% KOH solution and extracted into 25 ml of dichloromethane. The organic layer was dried over sodium sulfate, filtered and concentrated to give 0.098 g (100w) of 3-[4-(2-pyridyl)- piperidin-1-yl]propylamine which was used as such for the subsequent step (step h).

e. Methyl 2-{(3,4-difluorophenyl)methylene}-3-oxobutyrate.

A mixture of 3,4-difluorobenzaldehyde (14.2 g, 0.1 mol), methyl acetoacetate (12.2 g, 0.105 mol), piperidine (0.430 g, 5 mmol), and acetic acid (0.30 g, 5 mmol) in benzene (150 mL) was stirred and refluxed with a Dean-Stark trap for 8 hours. Benzene was evaporated, the residue was dissolved in ethyl acetate (200 mL) and washed with brine (50 mL), saturated potassium bisulfate solution (50 mL), and saturated sodium bicarbonate solution in sequence. The ethyl acetate solution was dried (magnesium sulfate), solvent removed under reduced pressure and the residue was purified by column chromatography (SiO2, EtOAc/hexane, 10%–15%). The product, methyl 2-{(3,4-difluorophenyl) methylene}-3-oxobutyrate, was obtained as a yellow oil (0.98 g, 98.3%) and was used in the next step without any further characterization.

f. 6-(3,4-Difluorophenyl)-1,6-dihydro-2-methoxy-5-methoxycarbonyl-4-methylpyrimidine.

A mixture of methyl 2-{(3,4-difluorophenyl)methylene}-3-oxobutyrate (8.8 g, 36.6 mmol), O-methylisourea hydrogen sulfate (9.4 g, 55 mmol), and NaHCO$_3$ (12.3 g, 0.146 mol) in DMF (30 mL) was stirred and heated at 70° C. for 16 hours. The mixture was cooled, diluted with EtOAc (300 mL) and washed with water (5×300 mL), brine (300 mL), and dried (MgSO$_4$). Solvent was evaporated and the crude product was purified by flash column chromatography on silica gel using 10% through 20% EtOAc in hexane as the gradient eluent, to leave the product as an oil (3.82 g, 30.2%); $^1$H-NMR (CDCl$_3$): δ 2.32,2.39 (2 s, 3 H), 3.58, 3.64 (2 s, 3 H), 3.72, 3.85 (2 s, 3 H), 5.55 (s, 1 H), 6.13–7.8 (m, 4 H)

g. 6-(3,4-Difluorophenyl)-1,6-dihydro-2-methoxy-5-methoxycarbonyl-4-methyl-1-[(4-nitrophenyloxy)carbonyl]pyrimidine.

To a solution of 6-(3,4-difluorophenyl)-1,6-dihydro-2-methoxy-5-methoxycarbonyl-4-methylpyrimidine (2.82 g, 9.52 mmol) and 4-dimethylaminopyridine (1.16 g, 9.52 mmol) in CH$_2$Cl$_2$ (50 mL),at 0–5° C., 4-nitrophenyl chloroformate (1.82 g, 9.04 mmol) was added and the mixture was allowed to warm to room temperature. After 12 hours solvent was evaporated and the residue was purified by flash column chromatography (SiO$_2$, EtOAc/hexane, 10%–15%) to obtain the product as white crystals (3.72, 84.7%); m.p. 172–174° C.; $^1$H-NMR (CDCl$_3$): δ 2.51 (s, 3 H), 3.72 (s, 3 H), 3.97 (s, 3 H), 6.26 (s, 1 H), 7.0–7.3 (m, 3 H), 7.38 (d, J=9.3 Hz, 2 H), 8.32 (d, J=9.3 Hz, 2 H).

h. 6-(3,4-Difluorophenyl)-5-methoxycarbonyl-4-methyl-2-oxo-1-{N-[4-(2-pyridyl)-piperidine-1-yl]propyl}carboxamido-1,2,3,6-tetrahydropyrimidine dihydrochloride.

To 6-(3,4-difluorophenyl)-1,6-dihydro-2-methoxy-5-methoxycarbonyl-4-methyl-1-(4-nitrophenoxy)carbonylpyrimidine (0.04 g,0.086 mmol) in 10 ml of dry dichloromethane, 3-[4-(2-pyridyl)-piperidine-1-yl] propylamine (0.038 g, 0.17 mmol) was added and the solution was stirred at room temperature for 24 hours. The reaction mixture was stirred for another 1 hour after addition of 2 ml of 6N HCl. After neutralization with 10% aqueous KOH solution, the reaction mixture was extracted into dichloromethane (3×10 ml). The organic layer was dried over sodium sulfate, filtered and concentrated. The crude product was purified by flash chromatography (EtOAc: MeOH, 4.5:0.5) to give 0.040 g (89%) as a syrup; $^1$H-NMR (CDCl$_3$): δ 1.73–2.11 (m, 7 H) 2.41 (s, 6 H), 2.69 (m, 1 H), 3.04 (d, J=12.1 Hz, 2 H), 3.31–3.48 (m, 2 H), 3.71 (s, 3 H), 6.70 (s, 1 H), 7.24–7.27 (m, 5 H), 7.61 (t, J=8.0 Hz, 2 H), 8.51 (d, J=4.6 Hz, 1 H), 8.89 (t, J 5.1 Hz, 2 H).

To the free base (0.04g, 0.07 mmol) in 4 ml of dichloromethane, 5 ml of 1N HCl in ether was added, and the solution concentrated under reduced pressure. Recrystallization from ether gave 0.046 g (98%) of 6-(3,4-difluorophenyl)-5-methoxycarbonyl-4-methyl-2-oxo-1-{N-[4-(2-pyridyl)-piperidine-1-yl]propyl}carboxamido-1,2,3,6-tetrahydropyrimidine dihydrochloride as a white solid; m.p. 170–174° C.; Anal. Calcd. for C$_{27}$H$_{33}$Cl$_2$F$_2$N$_5$O$_4$.1.0 H$_2$O: C, 52.43; H,5.70, N11.30. Found: C, 52.16; H 5.35; N 11.10.

EXAMPLE 22

6-(3,4-Benzofurazan-5-yl)-5-methoxycarbonyl-4-methyl-2-oxo-1-{N-[4-(2-pyridyl)-piperidin-1-]propyl}carboxamido-1,2,3,6-tetrahydropyrimidine dihydrochloride (Scheme 8).

5-Methylbenzfuroxan.

4-Methyl-2-nitroaniline (100 g, 0.650 mol) was suspended in saturated alcoholic sodium hydroxide solution (1.50 1). To this suspension was added with cooling (5° C.) commercial aqueous sodium hypochlorite till the red color disappeared. The fluffy yellow precipitate formed was filtered, washed with cold water and recrystallized from ethanol to get 5-Methylbenzfuroxan (88.2 g, 89 % yield) as a pale solid.

5-Methylbenzofurazan.

To 5-Methylbenzfuroxan (88.2 g, 0.59. mol) in refluxing EtOH (75 ml) was added dropwise P(OEt)$_3$ (150 ml). When addition was complete, refluxing was continued for 1 more hour. The solvent was removed by rotary evaporation and the residue shaken with water (200 mL) and allowed to stand overnight at (0~5° C.). The brown solid so obtained was filtered, washed with water and chromatograghed on silica gel to yield 5-Methylbenzofurazan (70 g, 87%) as white needle.

5-Dibromomethylbenzofurazan.

5-Methylbenzofurazan (70 g, 0.52 mol), NBS (325 g), and benzoyl peroxide (0.5 g) were refluxed with stirring in carbon tetrachloride (1.5 L) with exclusion of moisture for 30 hours. The reaction mixture was washed with water (2–0.5L), dried (NaSO$_4$), and the solvent was removed in vacuo. The residue was chromatographed (silica, EtOAc-hexane, 1:150) to give 122 g (80%) of the title compound. The resulting white solid was used in the next step without any further characterization.

5-Formylbenzofurazan.

To a refluxing mixture of the dibromomethylbenzofurazan (122 g, 418 mmol) in EtOH (1 L) was added AgNO$_3$ (163 g) in 2 L of water. Refluxing was continued for 2 hours. The mixture was cooled and the AgBr was removed by filtration through Celite, and the solvent was concentrated to a small volume. The resulting solution was extracted with toluene (10×100 mL), dried (MgSO$_4$), and the solvent was removed in vacuo. The residue was chromatographed on silica (EtOAc-hexane, 8:1000) to give 48.2 g of the title aldehyde (78%) as a white solid.

a. Methyl 2-{(benzofuran-5-yl)methylene}-3-oxobutyrate.

A mixture of 5-Formylbenzofurazan (0.6 g, 4.1 mmol), methyl acetoacetate (0.52 g, 4.5 mmol), piperidine (0.019 g, 0.225 mmol), and acetic acid (0.014 g, 0.225 mmol) in benzene (30 mL) was stirred and refluxed with a Dean-Stark trap for 8 h. Benzene was evaporated, the residue was dissolved in ethyl acetate (80 mL) and washed with brine (50 mL), saturated potassium bisulfate solution (50 mL), and saturated sodium bicarbonate solution in sequence. The ethyl acetate solution was dried (magnesium sulfate), solvent removed under reduced pressure and the residue was purified by column chromatography (SiO2, EtOAc/hexane, 10%–15%). The product, methyl 2{(benzofuran-5-yl)methylene}-3-oxobutyrate, was obtained as an oil (0.98 g, 98.3%) and was used in the next step without any further characterization.

b. 6-(Benzofurazan-5-yl)-1,6-dihydro-2-methoxy-5-methoxycarbonyl-4-methylpyrimidine.

A mixture of methyl2-{(benzofuran-5-yl)methylene}-3-oxobutyrate (1.02 g, 4.1 mmol), O-methylisourea hydrogen sulfate (1.06 g, 6.2 mmol), and $NaHCO_3$ (1.3 g, 16.4 mmol) in DMF (15 mL) was stirred and heated at 70° C. for 16 h. The mixture was cooled, diluted with EtOAc (50 mL) and washed with water (5×50 mL), brine (50 mL), and dried ($MgSO_4$). Solvent was evaporated and the crude product was purified by flash column chromatography on silica gel using 10% through 20% EtOAc in hexane as the gradient eluent, to leave the product as an oil (0.52 g, 43%); $^1$H-NMR ($CDCl_3$): δ 2.38,2.42 (2 s, 3 H), 3.60, 3.66 (2 s, 3 H), 3.74, 3.82 (2 s, 3 H), 5.53, 5.68 (2 s, 1 H), 6.31, 6.32 (br s, 1 H), 7.0–7.8 (m, 3 H).

c. 6-(Benzofurazan-5-yl)-1,6-dihydro-2-methoxy-5-methoxycarbonyl-4-methyl-1-[(4-nitrophenyloxy)carbonyl]pyrimidine.

To a solution of 6-(benzofuran-5-yl)-1,6-dihydro-2-methoxy-5-methoxycarbonyl-4-methylpyrimidine (0.485 g, 1.6 mmol) and 4-dimethylaminopyridine (0.2 g, 1.6 mmol) in $CH_2Cl_2$ (20 mL),at 0–5° C., was added 4-nitrophenyl chloroformate (0.307 g, 1.52 mmol) and the mixture was allowed to warm to room temperature. After 12 hours solvent was evaporated and the residue was purified by flash column chromatography (SiO2, EtOAc/hexane, 10%–15%) to obtain the product as white crystals (0.665 g, 89%); m.p. 180–183° C.; $^1$H-NMR ($CDCl_3$): δ 2.54 (s, 3 H), 3.75 (s, 3 H), 3.98 (s, 3 H), 6.37 (s, 1 H), 7.40 (d, J=9.3 Hz, 2 H), 7.52 (d, J=9.0 Hz, 1 H), 7.68 (s, 1 H), 7.84 (d, J=9.0 Hz, 1 H), 8.32 (d, J=9.3 Hz, 2 H)

d. 6-(3,4-Benzofurazan-5-yl)-5-methoxycarbonyl-4-methyl-2-oxo-1-{N-[4-(2-pyridyl)-piperidin-1-]propyl}carboxamido-1,2,3,6-tetrahydropyrimidine dihydrochloride.

To 6-(benzofurazan-5-yl)-1,6-dihydro-2-methoxy-5-methoxycarbonyl-4-methyl-1-(4-nitrophenoxy)carbonylpyrimidine (0.04 g,0.085 mmol) in 10 ml of dry dichloromethane, 3-[4-(2-pyridyl)-piperidine-1-yl] propylamine (0.037 g, 0.17 mmol) was added and the solution was stirred at room temperature for 24 hours. The reaction mixture was stirred for another 1 hour after addition of 2 ml of 6N HCl. After neutralization with 10% aqueous KOH solution, the reaction mixture was extracted into dichloromethane (3×10 ml). The organic layer was dried over sodium sulfate, filtered and concentrated. The crude product was purified by flash chromatography (EtOAc: MeOH, 4.5:0.5) to give 0.040 g (89%) as a syrup ; $^1$H-NMR ($CDCl_3$): δ 1.74–2.10 (m, 7 H), 2.46 (s, 6 H), 2.70–2.72 (m, 1 H), 3.05 (d, J=12.1 Hz, 2 H), 3.34–3.48 (m, 2 H), 3.76 (s, 3 H), 6.82 (s, 1 H), 7.11–7.32 (m, 3 H), 7.54–7.78 (m, 4 H), 8.53 (d, J=4.6 Hz, 1 H), 8.89 (t, J=5.16 Hz, 2 H). To the free base (0.04g, 0.07 mmol)in 4 ml of dichloromethane, 5 ml of 1N HCl in ether was added, and the solution concentrated under reduced pressure.

Recrystallization from ether gave 0.040 g (87%) of 6-(3,4-benzofurazan-5-yl)-5-methoxycarbonyl-4-methyl-2-oxo-1-{N-[4-(2-pyridyl)-piperidine-1-yl]propyl}carboxamido-1,2,3,6-tetrahydropyrimidine dihydrochloride as a white solid; m.p. 200–204° C.; Anal. Calcd. for $C_{27}H_{33}Cl_2N_7O_5$.2.5 $H_2O$: C, 49.77; H,5.88. Found: C, 49.41; H 5.20.

EXAMPLE 23

6-(3,4-Difluorophenyl)-1,6-dihydro-5-methoxycarbonyl-1-(5-(4-methoxycarbonyl-4-phenylpiperidin-1-yl)-pentyl)-2,4-dimethylpyrimidine (Scheme 9).

a. 6-(3,4-Difluorophenyl)-1,6-dihydro-2,4-dimethyl-5-methoxycarbonylpyrimidine.

To a solution of acetamidine hydrochloride (1.53 g, 16.2 mmol.) in DMF (10 mL) were added a solution of potassium tert-butoxide (1.33 g, 11.8 mmol.) in DMF (10 mL) and a solution of methyl {2-(3,4-difluorophenyl)methylene}-3-oxobutanoate (2.6 g, 10.8 mmol.) in DMF (10 mL) at 0° C. After the mixture was stirred for 0.5 hour at 0° C., p-toluenesulfonic acid monohydrate (4.1 g, 21.5 mmol.) was added. The mixture was heated at 100–120° C. for 2 hrs. The reaction mixture was cooled to room temperature, quenched with aqueous NaOH solution (2N, 60 mL), and extracted with ether. The organic layer was dried over $Na_2SO_4$ and evaporated. The residue was flash chromatographed over silica gel (eluent: ethyl acetate) to give the product in 59% yield (1.8 g) as a yellow solid: $^1$H NMR (300 MHz, $CDCl_3$) δ 1.98 (3H, s), 2.31 (3H, s), 3.59 (3H, s), 5.47 (1H, s), 7.03–7.05 (3H, m).

b. 1-(5-Chloropentyl)-6-(3,4-difluorophenyl)-1,6-dihydro-2,4-dimethyl-5-methoxycarbonylpyrimidine.

To a suspension of NaH (90 mg, 60% dispersion in mineral oil, 2.25 mmol.) in THF (7 mL) was added a solution of the above yellow solid (0.6 g, 2.14 mmol.) in THF (8 mL) at 0° C. After 20 min, 1-bromo-5-chloropentane (1 mL, d 1.408, 7.59 mmol.) was added. The reaction mixture was then refluxed overnight. After the removal of the solvent, the residue was flash chromatographed over silica gel (eluent: ethyl acetate) to give the product in 75% yield (0.614 g) as a yellow oil: $^1$H NMR (300 MHz, $CDCl_3$) δ 1.42–1.75 (6H, m), 2.17 (3H, s), 2.28 (3H, s), 3.05–3.45 (2H, m), 3.49 (2H, t, J=5.88Hz), 3.63 (3H, s), 5.23 (1H, s), 7.01–7.15 (3H, m).

c. 6-(3,4-Difluorophenyl)-1,6-dihydro-5-methoxycarbonyl-1-(5-(4-methoxycarbonyl-4-phenylpiperidin-1-yl)-pentyl)-2,4-dimethylpyrimidine.

A mixture of the above yellow oil (0.667 g, 1.73 mmol.), 4-methoxycarbonyl-4-phenylpiperidine (0.76 g, 3.47 mmol.), potassium carbonate (0.96 g, 6.95 mmol.), sodium iodide (0.52 g, 3.47 mmol.) and 1,4-dioxane (15 mL) was refluxed overnight. The undissolved solid was then filtered off and the solvent was evaporated. The residue was flash chromatographed over silica gel (eluent: 80:20 v/v ethyl acetate-2M ammonia in methanol) to give the title compound in 78% yield (0.768 g) as a yellow oil: CIMS, m/z 568 (MH$^+$); $^1$H NMR (300 MHz, $CDCl_3$): δ 1.23–1.28 (2H, m), 1.43–1.51 (2H, m), 1.77–2.13 (8H, m), 2.16 (3H, s), 2.28 (3H, s), 2.47–2.55 (2H, m), 2.74–2.81 (2H, m), 3.00–3.12 (1H, m), 3.22–3.38 (1H, m), 3.613 (3H, s), 3.615 (3H, s), 5.22 (1H, s), 6.99–7.35 (3H, m)

Treatment of the free base with 2 equivalents of 1M HCl in ether gave the HCl salt as a yellow foam: m.p. 170–176° C. Anal. Calc. for $C_{32}H_{39}F_2N_3O_4$.2HCl.2.3$H_2O$: C, 56.35; H, 6.74; N, 6.16; Found: C, 56.34; H, 6.62; N, 5.86.

Pharmacological Profiles of the Compounds in Cloned Human Adrenergic Receptors

Binding affinities were measured for selected compounds of the invention at six cloned human alpha-1 and alpha-2 receptor subtypes, as well as at the L-type calcium channel. The protocols for these experiments are given below.

Protocol for the Determination of the Potency of $α_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic receptors as follows:

$\alpha_{1A}$ Human Adrenergic Receptor:

The entire coding region of α1A (1719 bp), including 150 base pairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene) and the plasmid pGCcos3neo (plasmid containing the aminoglycoside transferase gene) into LM(tk⁻), CHO, and NIH3T3 cells, using calcium phosphate technique. The cells were grown, in a controlled environment (37° C., 5% $CO_2$), as monolayers in Dulbecco's modified Eagle's Medium (GIBCO, Grand Island, N.Y.) containing 25mM glucose and supplemented with 10% bovine calf serum, 100 units/ml penicillin g, and 100 μg/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

$\alpha_{1B}$ Human Adrenergic Receptor:

The entire coding region of α1B (1563 bp), including 200 base pairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above.

$\alpha_{1C}$ Human Adrenergic Receptor:

The entire coding region of α1C (1401 bp), including 400 base pairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6kb HincII genomic clone, a central 1.8 EcoRI hippocampal cDNA clone, and a 3' 0.6Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays:

Transfected cells from culture flasks were scraped into 5ml of 5mM Tris-HCl, 5mM EDTA, pH 7.5, and lysed by sonication. The cell lysates were centrifuged at 1000 rpm for 5 min at 4° C., and the supernatant was centrifuged at 30,000×g for 20 min at 40° C. The pellet was suspended in 50mM Tris-HCl, 1mM $MgCl_2$, and 0.1% ascorbic acid at pH 7.5. Binding of the α1 antagonist [$^3$H]prazosin (0.5 nM, specific activity 76.2 Ci/mmol) to membrane preparations of LM(tk-) cells was done in a final volume of 0.25 ml and incubated at 37° C. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

$\alpha_2$ Human Adrenergic Receptors:

To determine the potency of $\alpha_1$ antagonists at the $\alpha_2$ receptors, LM(tk-) cell lines stably transfected with the genes encoding the $\alpha_{2A}$, $\alpha_{2B}$ and $\alpha_{2C}$ receptors were used. The cell line expressing the $\alpha_{2A}$ receptor is designated L-$\alpha_{2A}$, and was deposited on Nov. 6, 1992 under ATCC Accession No. CRL 11180. The cell line expressing the $\alpha_{2B}$ receptor is designated L-NGC-$\alpha_{2B}$, and was deposited on Oct. 25, 1989 under ATCC Accession No. CRL10275. The cell line expressing the $\alpha_{2C}$ receptor is designated L-$\alpha_{2C}$, and was deposited on Nov. 6, 1992 under ATCC Accession No. CRL-11181. Cell lysates were prepared as described above (see Radioligand Binding Assays), and suspended in 25mM glycylglycine buffer (pH 7.6 at room temperature). Equilibrium competition binding assay were performed using [3H]rauwolscine (0.5nM), and nonspecific binding was determined by incubation with 10 μgM phentolamine. The bound radioligand was separated by filtration through GF/B filters using a cell harvester.

Determination of the Activity of $\alpha_1$ Antagonists at Calcium Channels

The potency of $\alpha_1$ antagonists at calcium channels was determined in competition binding assays of [3H] nitrendipine to membrane fragments of rat cardiac muscle, essentially as described by Glossman and Ferry (Methods in Enzymology 109:513–550, 1985). Briefly, the tissue was minced and homogenized in 50mM Tris-HCl (pH 7.4) containing 0.1mM phenylmethylsulfonyl fluoride. The homogenates were centrifuged at 1000 g for 15 minutes, the resulting supernatant was centrifuged at 45,000 g for 15 minutes. The 45,000 g pellet was suspended in buffer and centrifuged a second time. Aliquots of membrane protein were incubated for 30 minutes at 37° C. in the presence of [3H]nitrendipine (1nM), and nonspecific binding was determined in the presence of 10 μM nifedipine. The bound radioligand was separated by filtration through GF/B filters using a cell harvester.

The compounds described above were assayed using cloned human alpha adrenergic receptors and the rat calcium channel. The preferred compounds were found to be selective $\alpha_{1C}$ antagonists. The binding affinities of compounds 19–23 are illustrated in the following table. Binding affinities of compounds 19–23 at cloned human α1a, α1b and α1c receptors.

| | hα1a | | | hα1b | | | hα1c | | |
|---|---|---|---|---|---|---|---|---|---|
| Example | pKi | SEM | n | pKi | SEM | n | pKi | SEM | n |
| 19 | 6.14 | 0.02 | 3 | 6.21 | 0.09 | 3 | 9.74 | 0.02 | 3 |
| 20 | 6.46 | 0.04 | 3 | 6.59 | 0.08 | 3 | 9.68 | 0.05 | 3 |
| 21 | 6.01 | 0.03 | 3 | 6.33 | 0.06 | 3 | 9.41 | 0.09 | 3 |
| 22 | 6.24 | 0.06 | 3 | 6.37 | 0.06 | 3 | 9.54 | 0.09 | 3 |
| 23 | 6.17 | 0.04 | 4 | 6.32 | 0.06 | 4 | 8.99 | 0.12 | 4 | h = human

Scheme 1 General synthetic schemes for the synthesis of the piperidine sidechains
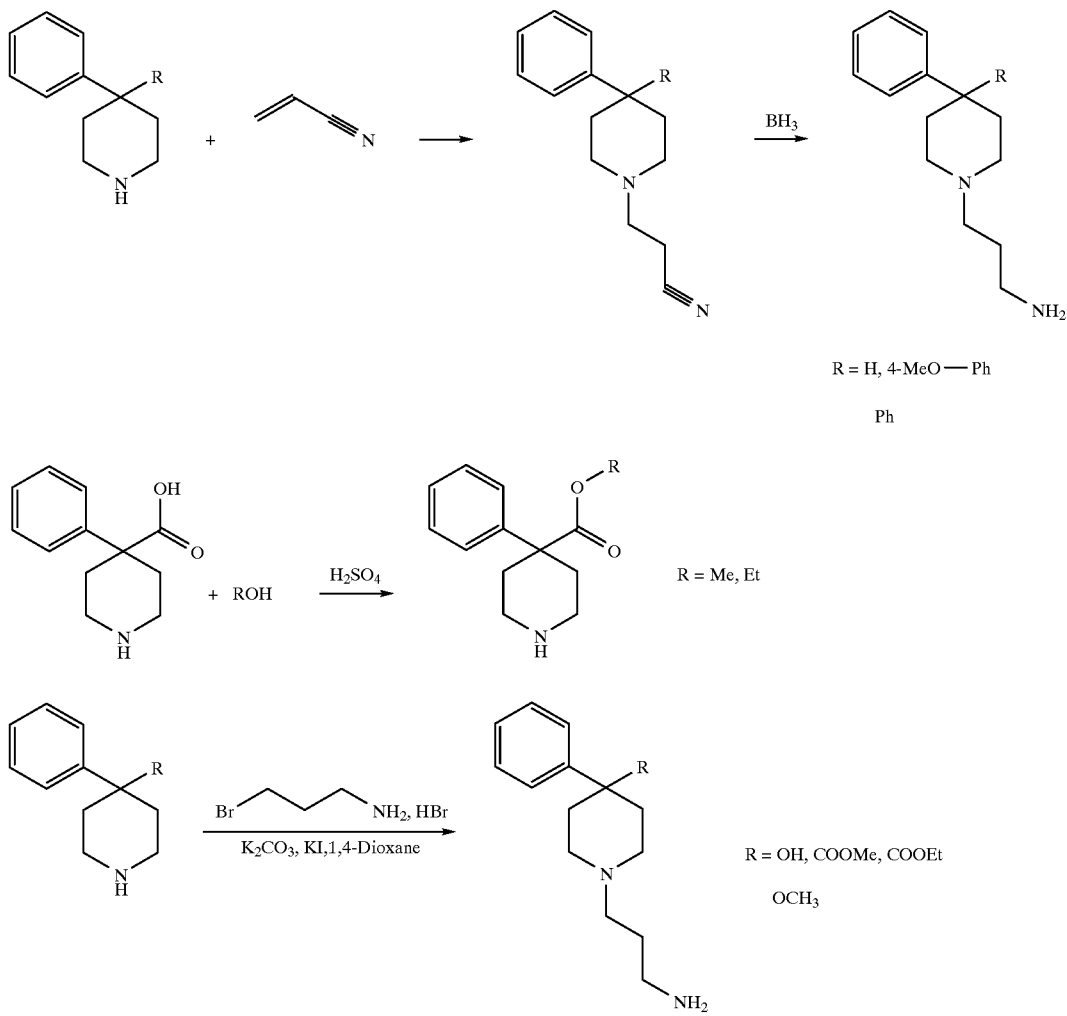
Scheme 1 (continued) General synthetic scheme for examples 1-17
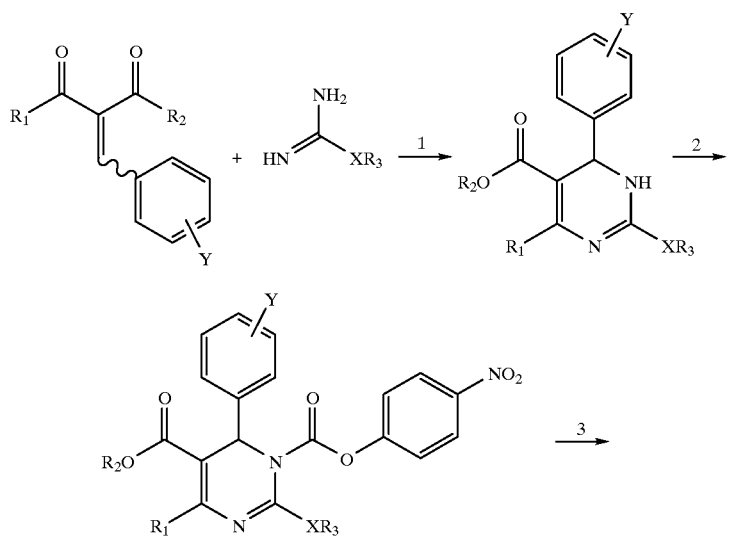

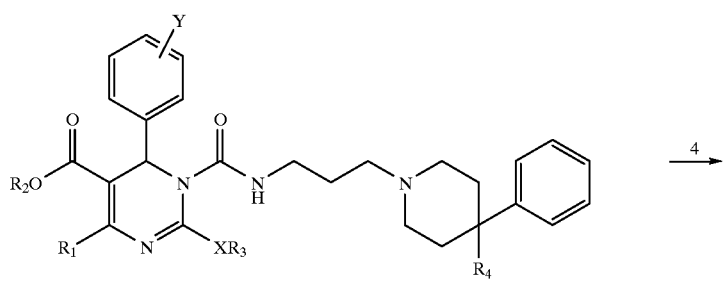
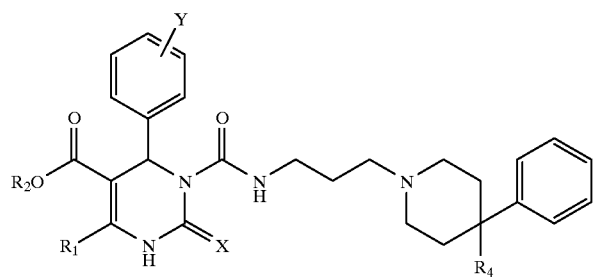
1. NaOAc, DMF.
2. 4-Nitrophenyl chloroformate, NaHCO$_3$, CH$_2$Cl$_2$, H$_2$O.
3.
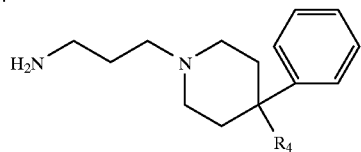
4. HCl/THF or EtSH/TFA.
Scheme 2 Synthetic scheme for example 14
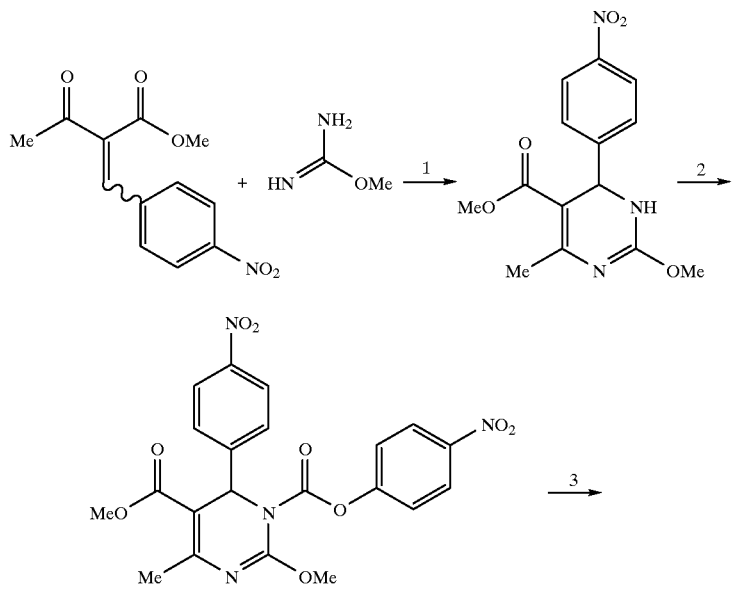

-continued
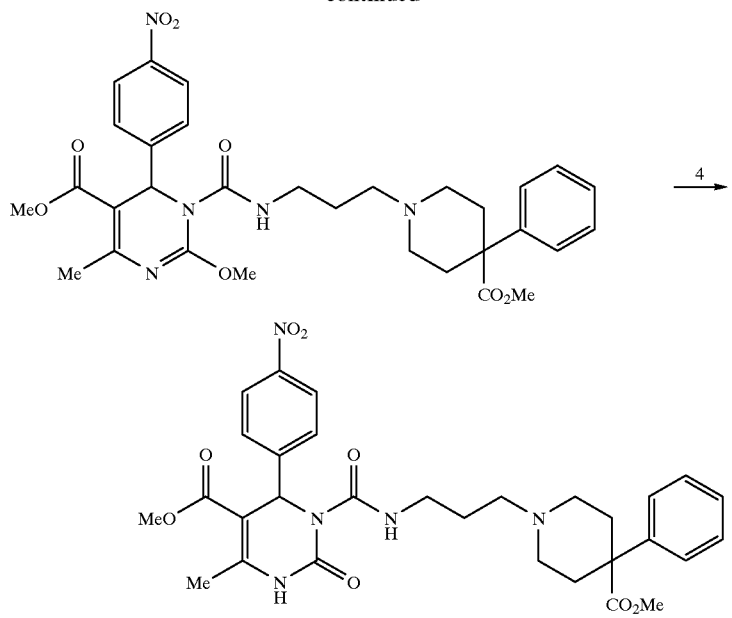
1. NaOAc, DMF.
2. 4-Nitrophenyl chloroformate, NaHCO₃, CH₂Cl₂, H₂O.
3. 3[(4-Methoxycarbonyl-4-phenyl)piperidine-1-yl]propylamine, THF.
4. 6N HCl/THF.
Scheme 3 Synthetic scheme for examples 14a and 14b
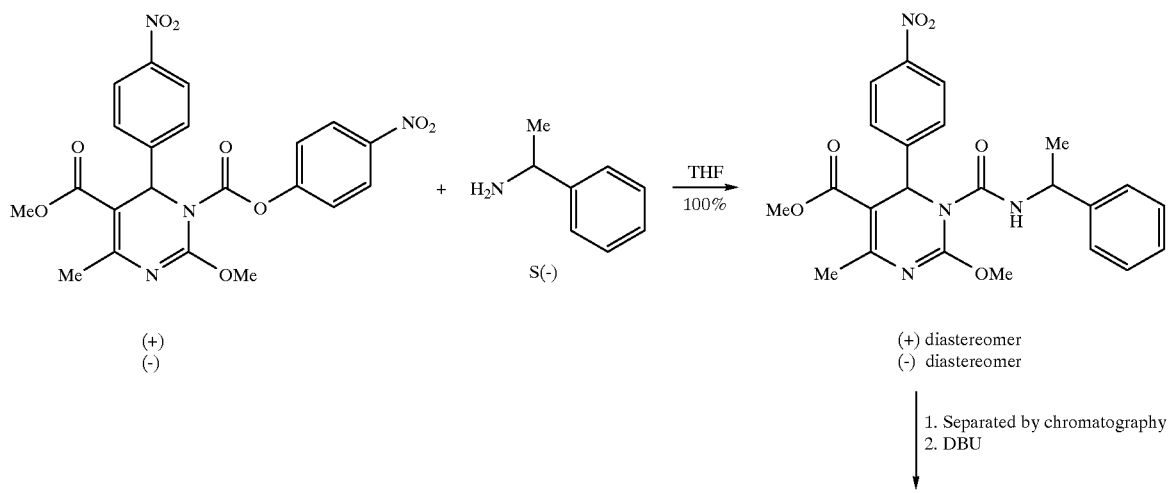
1. Separated by chromatography
2. DBU

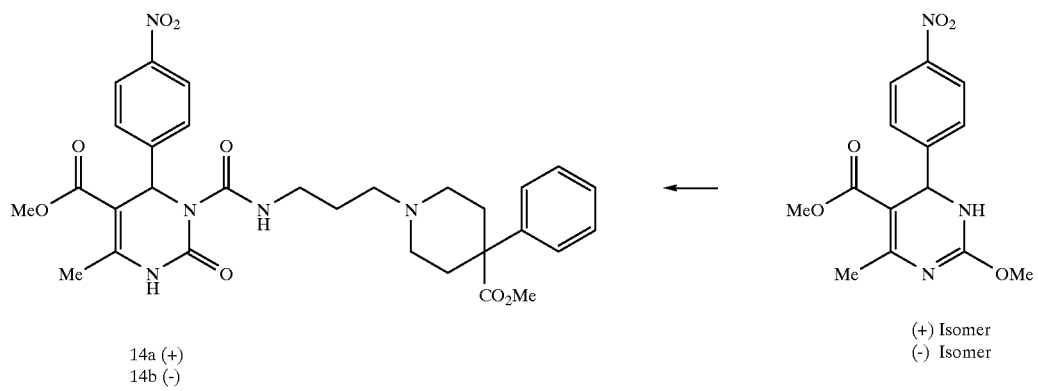
14a (+)
14b (−)
(+) Isomer
(−) Isomer
Scheme 4 Synthetic scheme for example 19
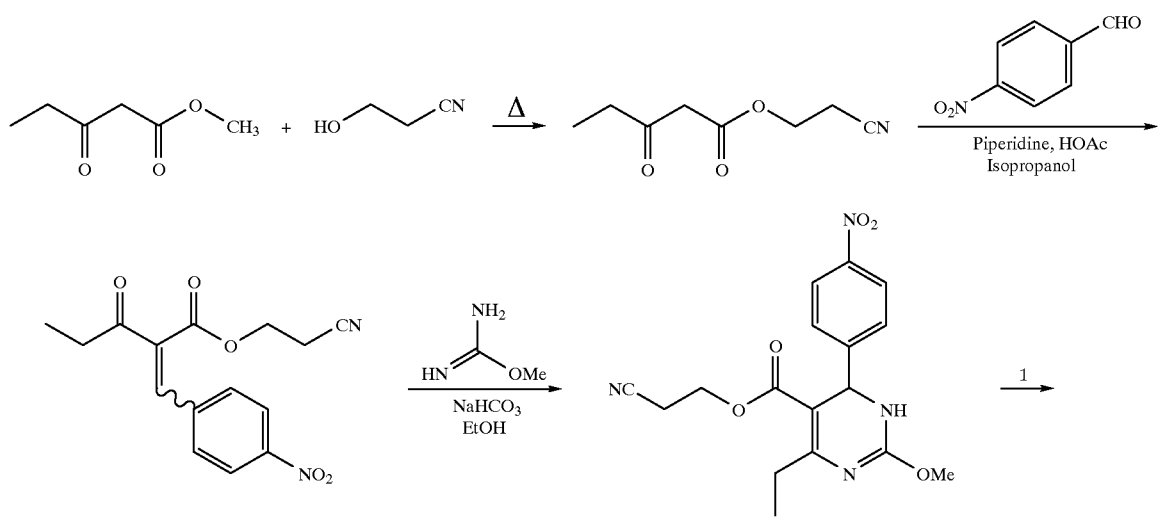

-continued
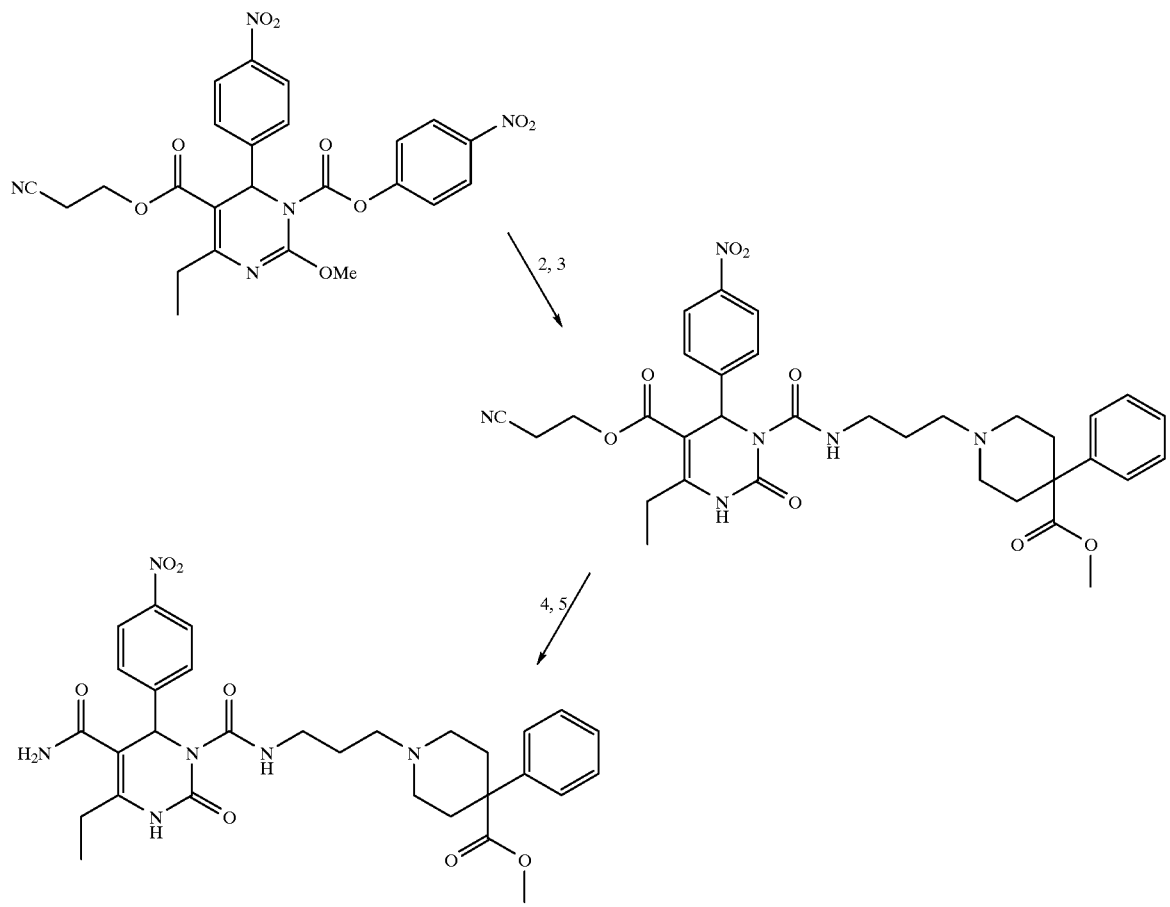
1. 4-Nitrophenyl chloroformate, NaHCO₃, CH₂Cl₂, H₂O.
2. 3-[(4-Methoxycarbonyl-4-phenyl)piperidin-1-yl]propylamine.
3. 6N HCl.
4. NaOH, Acetone.
5. DMAPECD, DMAP, NH₃, CH₂Cl₂.
Scheme 5 Synthetic scheme for example 20
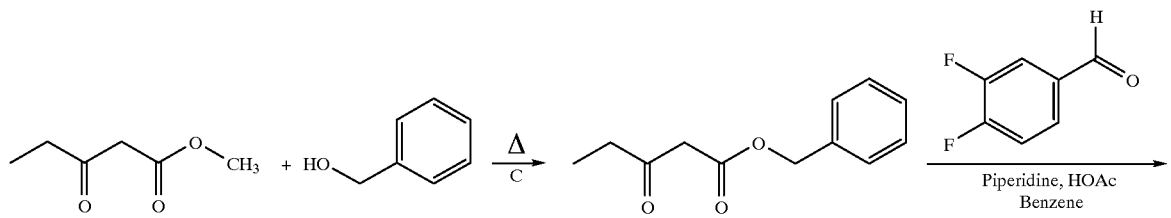

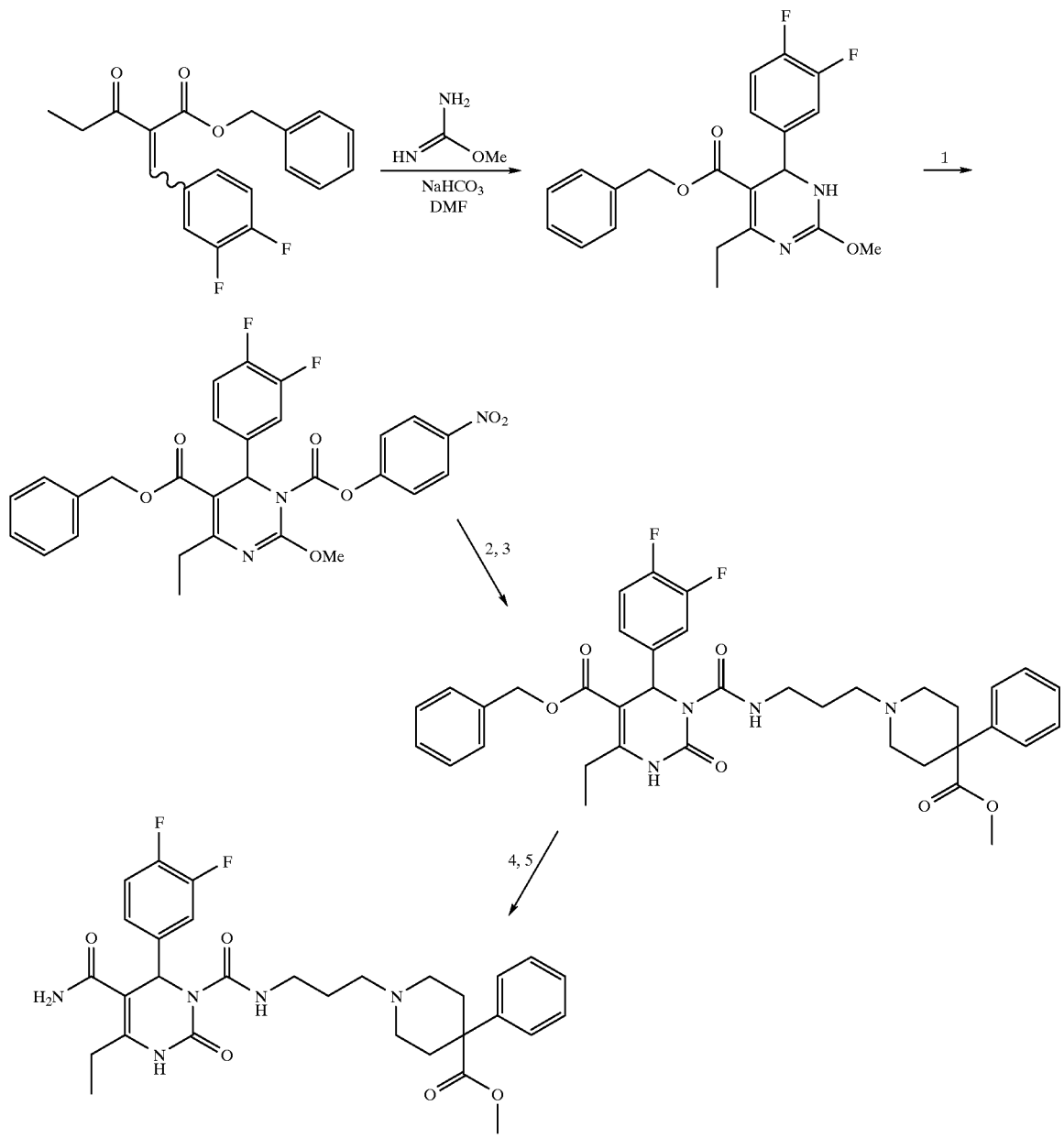
1. 4-Nitrophenyl chloroformate, DMAP, THF
2. 3-[(4-Methoxycarbonyl-4-phenyl)piperidin-1-yl]propylamine.
3. 6N HCl.
4. H₂, Pd-C, MeOH.
5. DMAPECD, DMAP, NH₄OH, CH₂Cl₂.
Scheme 6 Synthetic scheme for the preparation of
3-[4-(2-Pyridyl)-piperidin-1-yl]propylamine (Example 21 part d)
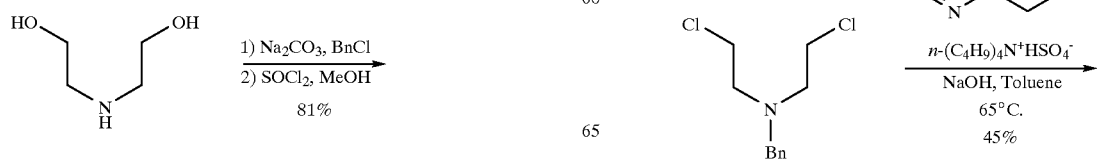

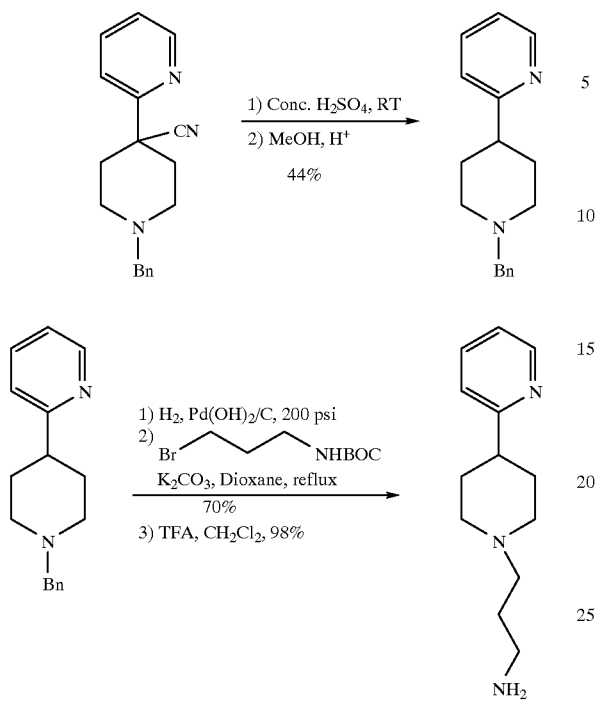
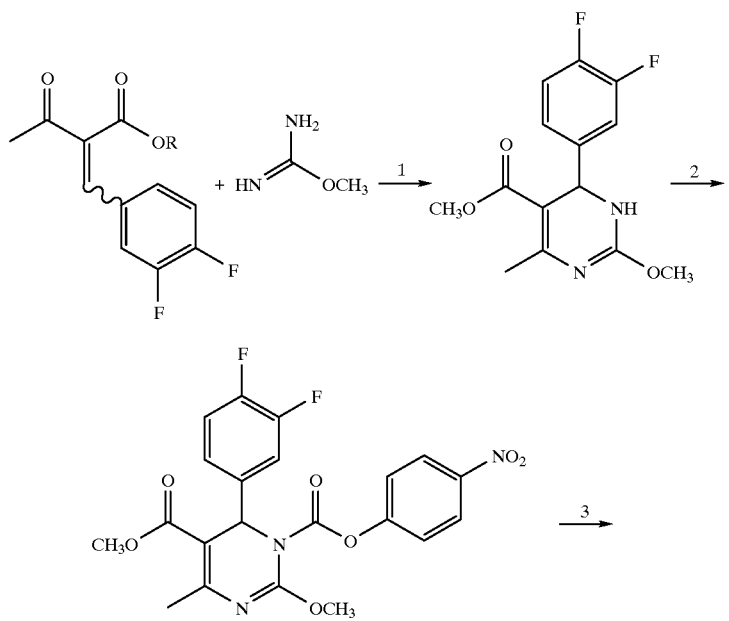
Scheme 7 Synthetic scheme for example 21

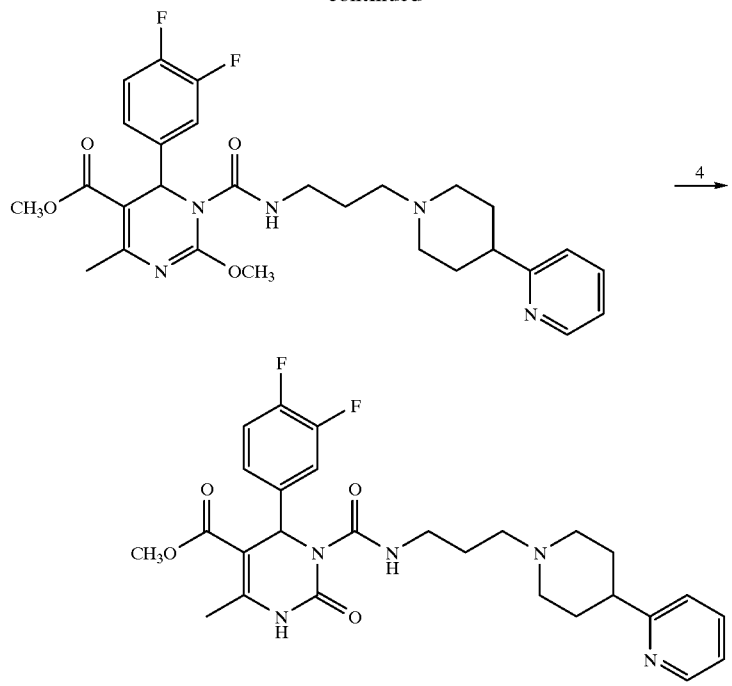
1. NaOAc, DMF.
2. 4-Nitrophenyl chloroformate, NaHCO₃, CH₂Cl₂, H₂O.
3. 3-[(4-Pyridyl)-piperidin-1-yl]propylamine, CH₂Cl₂.
4. 6N HCl/THF.
Scheme 8 Synthetic scheme for example 22
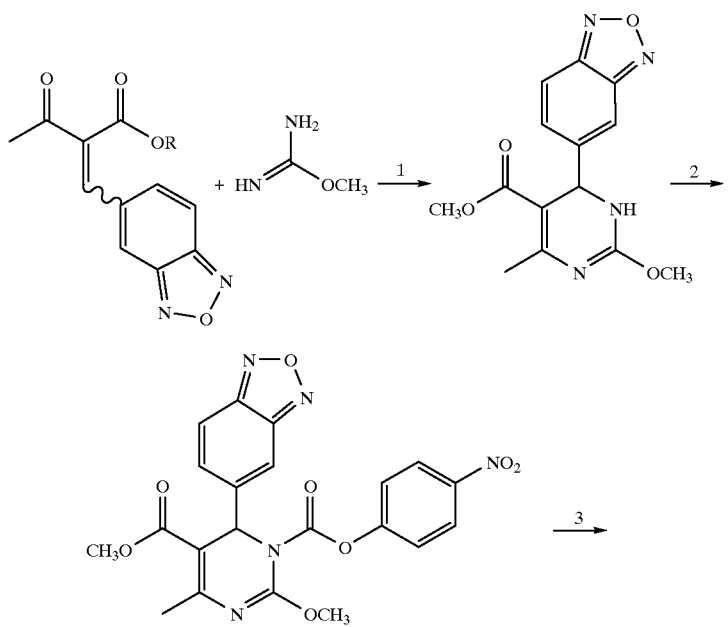

-continued
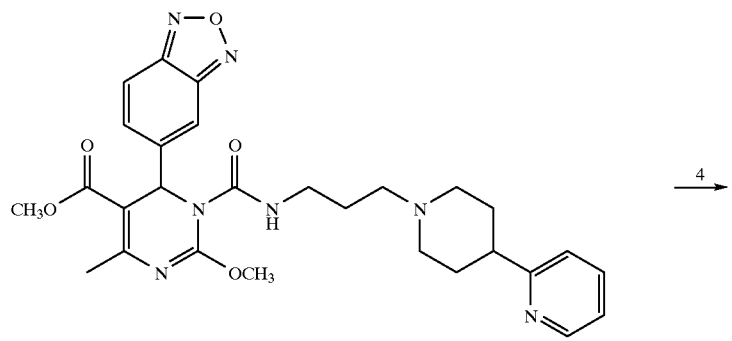
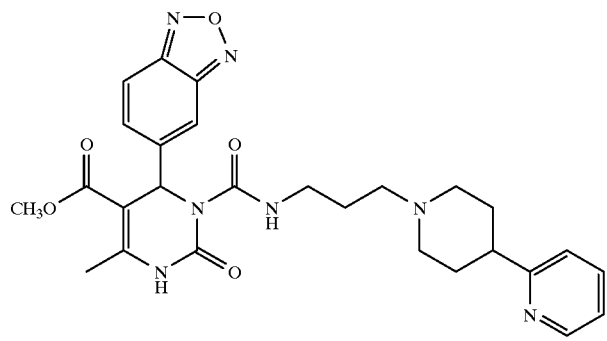
1. NaOAc, DMF.
2. 4-Nitrophenyl chloroformate, NaHCO₃, CH₂Cl₂, H₂O.
3. 3-[(4-Pyridyl)-piperidin-1-yl]propylamine, CH₂Cl₂.
4. 6N HCl/THF.
Scheme 9 Synthetic scheme for example 23
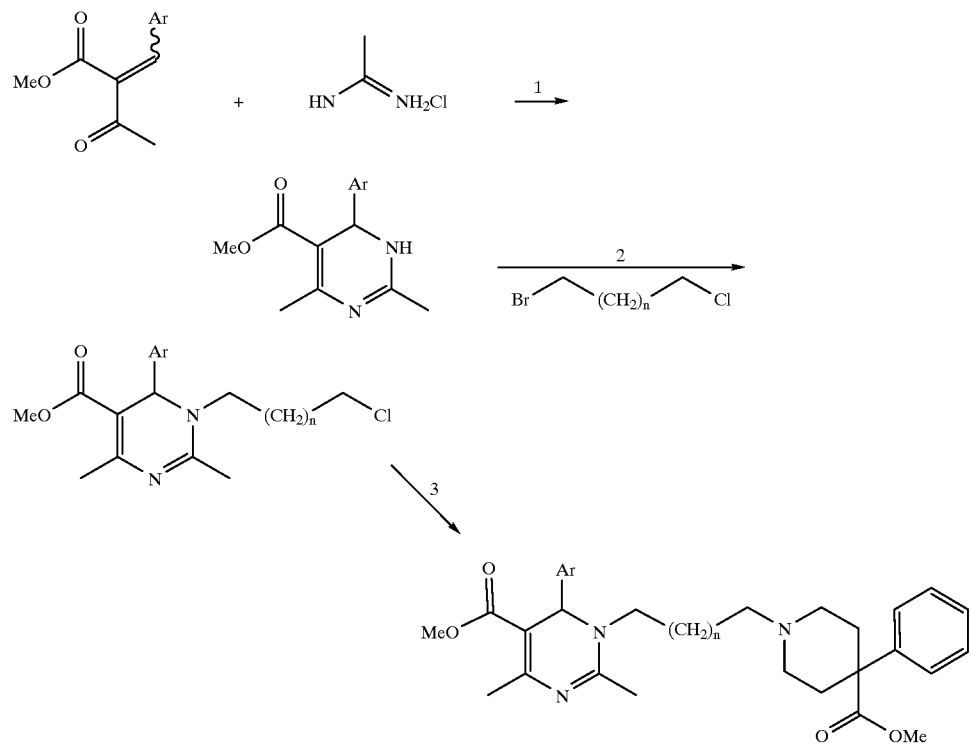

-continued 1. (a) t-BuOK, DMF, 0° C.; (b) TsOH H₂O, DMF, 100-120° C.
2. NaH, THF, reflux.
3. 4-Methoxycarbonyl-4-phenylpiperidine, K₂CO₃, NaI, 1,4-dioxane, reflux.

What is claimed is:
1. A compound having the structure:

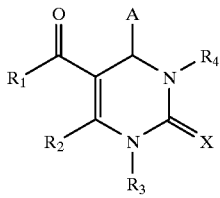

wherein A is

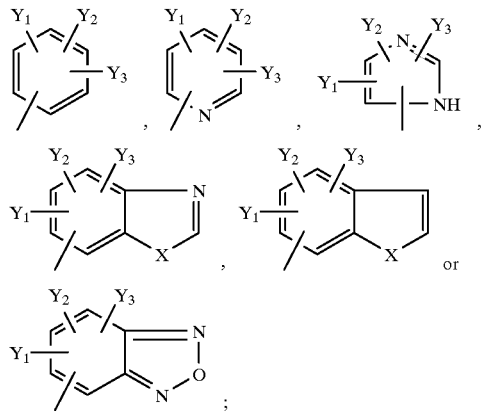

wherein each of $Y_1$, $Y_2$ and $Y_3$ is independently H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, —I, —NO₂, —N₃, —CN, —OR₆, —OCOR₆, —COR₆, —CONHR₆, —CON(R₆)₂, —COOR₆, —CF₃ or together constitute a methylenedioxy group;
wherein X is S, O or NH;
wherein $R_1$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl; —NHR₆, —N(R₆)₂ or —OR₆;
wherein $R_2$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_1$–$C_{10}$-alkyl, cycloalkyl-$C_1$–$C_{10}$-monofluoroalkyl or cycloalkyl-$C_1$–$C_{10}$-polyfluoroalkyl; —CN, —CH₂XR₆, —CH₂X(CH₂)ₙNHR₆, —(CH₂)ₙNHR₆, —CH₂X(CH₂)ₙN(R₆)₂, —CH₂X(CH₂)ₙN₃ or CH₂X(CH₂)ₙNHCXR₇;
wherein n is an integer from 0 to 5 and wherein X is as defined above;
wherein $R_3$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl;
wherein $R_4$ is

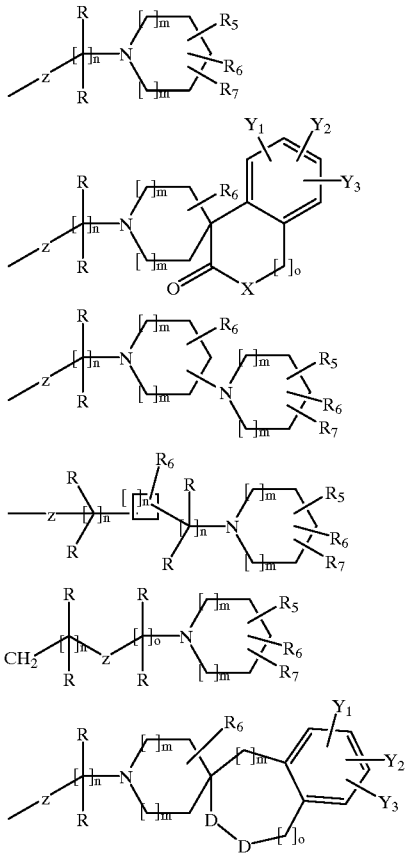

wherein each R is independently H; F; straight chained or branched $C_1$–$C_7$ alkyl, monofluoroalkyl or polyfluoroalkyl, $C_2$–$C_7$ alkenyl or alkynyl;
wherein $R_5$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl; phenyl, thiophenyl, pyridyl, pyrrolyl, furanyl, imidazolyl or indolyl; —COOR₆, —COR₆, —CONHR₆, —CN, —OH or —OR₆;
wherein each m is independently an integer from 0 to 3;
wherein o is an integer from 1 to 3; wherein each n is independently an integer from 0 to 5;
wherein each $R_6$ is independently H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl;
wherein $R_7$ is phenyl, pyridyl, thiophenyl, furanyl, pyrazinyl, pyrrolyl, naphthyl, indolyl, imidazolyl, benzfurazanyl, benzfuranyl or benzimidazolyl; $C_1$–$C_7$ alkyl, monofluoroalkyl or polyfluoroalkyl, $C_2$–$C_7$ alkenyl or alkynyl wherein the alkyl, monofluoroalkyl, polyfluoroalkyl, alkenyl or alkynyl is substituted with pyridyl, thiophenyl, furanyl, pyrazinyl, pyrrolyl, indolyl, imidazolyl, benzfurazanyl, benzfuranyl or benzimidazolyl;

provided that if $R_7$ is phenyl, $R_5$ cannot be H or straight chained or branched $C_1$–$C_7$ alkyl when $R_6$ is H or straight chained or branched $C_1$–$C_7$ alkyl;

wherein each of $Y_1$, $Y_2$ and $Y_3$ is as defined above; wherein X is as defined above;

wherein Z is $C_2$ alkenyl or alkynyl, $CH_2$, O, $CONR_6$, S, SO, $SO_2$ or $NR_6$; and wherein each D is independently $CH_2$, O, S, $NR_6$, CO or CS; or a pharmaceutically acceptable salt thereof.

2. The (−) enantiomer of the compound of claim 1.
3. The (+) enantiomer of the compound of claim 1.
4. The compound of claim 1 having the structure:

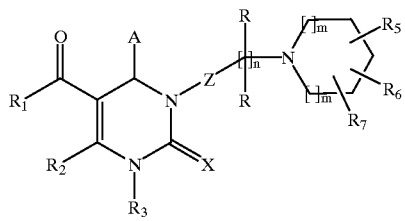

5. The compound of claim 4 having the structure:

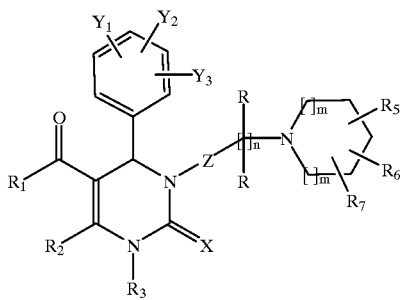

6. The compound of claim 5 having the structure:

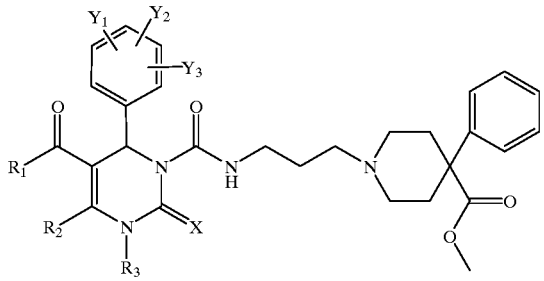

7. The compound of claim 6 having the structure:

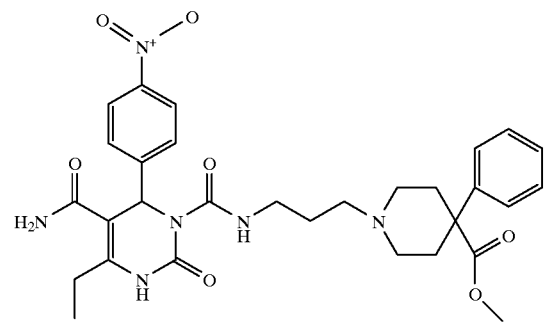

8. The compound of claim 6 having the structure:

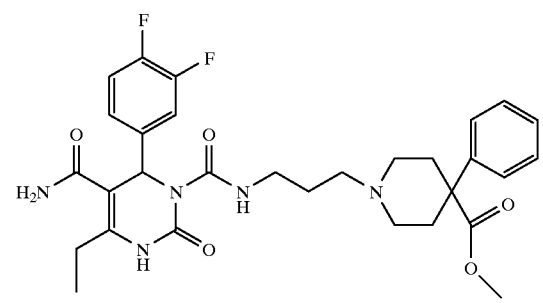

9. The compound of claim 5 having the structure:

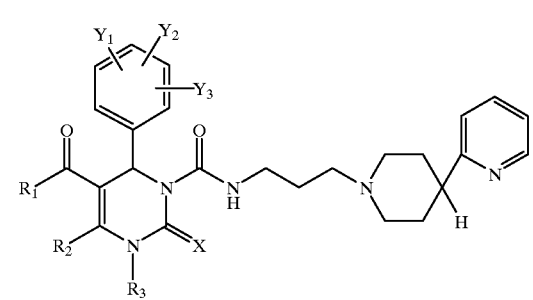

10. The compound of claim 9 having the structure:

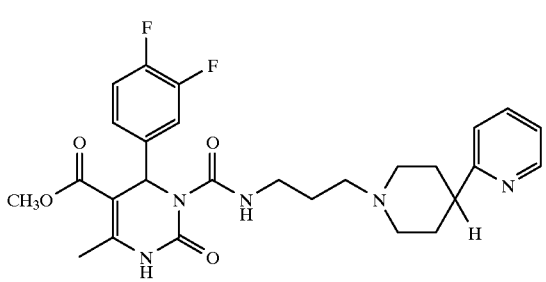

11. The compound of claim 9 having the structure:

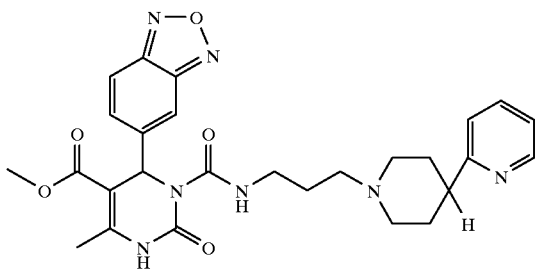

12. A compound having the structure:

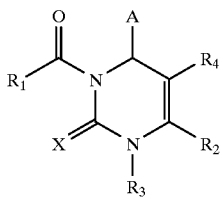

wherein A is

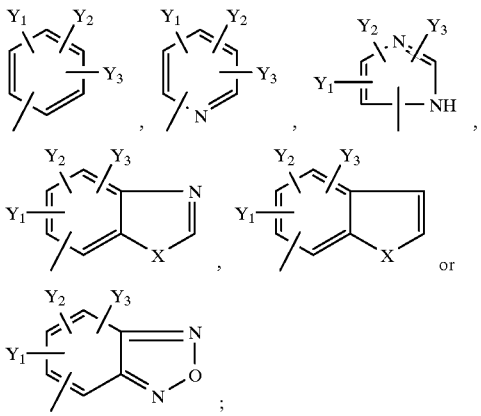

wherein each of $Y_1$, $Y_2$ and $Y_3$ is independently H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, —I, —$NO_2$, —$N_3$, —CN, —$OR_6$, —$OCOR_6$, —$COR_6$, —$CONHR_6$, —$CON(R_6)_2$, —$COOR_6$, —$CF_3$ or together constitute a methylenedioxy group;

wherein X is S, O or NH;

wherein $R_1$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl; —$NHR_6$, —$N(R_6)_2$ or —$OR_6$;

wherein $R_2$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl; $C_3$–$C_{10}$ cycloalkyl-$C_1$–$C_{10}$-alkyl, cycloalkyl-$C_1$–$C_{20}$-monofluoroalkyl or cycloalkyl-$C_1$–$C_{10}$-polyfluoroalkyl; —CN, —$CH_2XR_6$, —$CH_2X(CH_2)_nNHR_6$, —$(CH_2)_nNHR_6$, —$CH_2X(CH_2)_nN(R_6)_2$, —$CH_2X(CH_2)_nN_3$ or $CH_2X(CH_2)_nNHCXR_7$;

wherein n is an integer from 0 to 5 and wherein X is as defined above;

wherein $R_3$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl;

wherein $R_4$ is

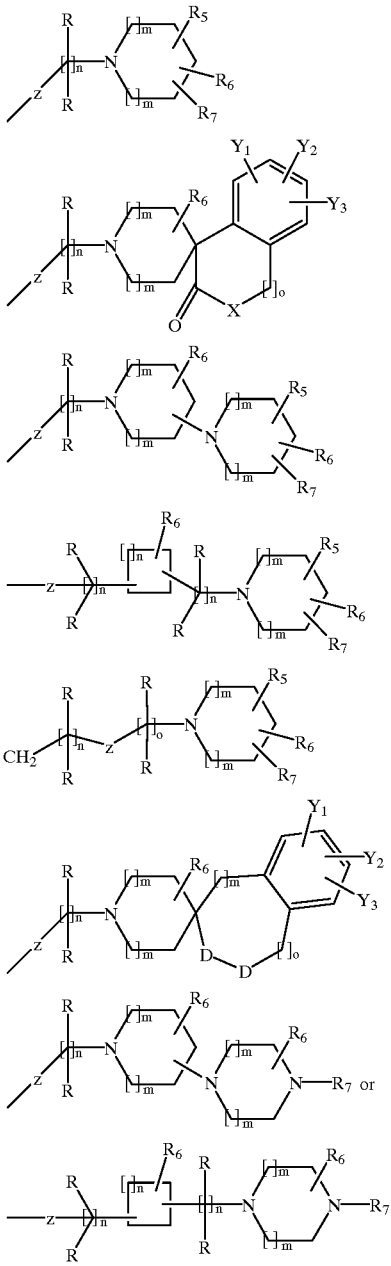

wherein each R is independently H; F; straight chained or branched $C_1$–$C_7$ alkyl, monofluoroalkyl or polyfluoroalkyl, $C_2$–$C_7$ alkenyl or alkynyl;

wherein $R_5$ is H; straight chained or branched $C_1$–$C_7$ alkyl, monofluoroalkyl or polyfluoroalkyl, $C_2$–$C_7$ alkenyl or alkynyl; $C_3$–$C_7$ cycloalkyl, monofluorocycloalkyl, polyfluorocycloalkyl or cycloalkenyl; phenyl, thiophenyl, pyridyl, pyrrolyl, furanyl, imidazolyl or indolyl; —COOR$_6$, —COR$_6$, —CONHR$_6$, —CN, —OH or —OR$_6$;

wherein each m is independently an integer from 0 to 3; wherein o is an integer from 1 to 3; wherein each n is independently an integer from 0 to 5;

wherein each R$_6$ is independently H; straight chained or branched C$_1$–C$_7$ alkyl, monofluoroalkyl or polyfluoroalkyl, C$_2$–C$_7$ alkenyl or alkynyl; C$_3$–C$_7$ cycloalkyl, monofluorocycloalkyl, polyfluorocycloalkyl or cycloalkenyl;

wherein R$_7$ is phenyl, pyridyl, thiophenyl, furanyl, pyrazinyl, pyrrolyl, naphthyl, indolyl, imidazolyl, benzfurazanyl, benzfuranyl or benzimidazolyl; C$_1$–C$_7$ alkyl, monofluoroalkyl or polyfluoroalkyl, C$_2$–C$_7$ alkenyl or alkynyl wherein the alkyl, monofluoroalkyl, polyfluoroalkyl, alkenyl or alkynyl is substituted with pyridyl, thiophenyl, furanyl, pyrazinyl, pyrrolyl, indolyl, imidazolyl, benzfurazanyl, benzfuranyl or benzimidazolyl;

provided that if R$_7$ is phenyl, R$_5$ cannot be H or straight chained or branched C$_1$–C$_7$ alkyl when R$_6$ is H or straight chained or branched C$_1$–C$_7$ alkyl;

wherein each of Y$_1$, Y$_2$ and Y$_3$ is as defined above; wherein X is as defined above;

wherein Z is C$_2$ alkenyl or alkynyl, CH$_2$, O, CONR$_6$, S, SO, SO$_2$ or NR$_6$; and wherein each D is independently CH$_2$, O, S, NR$_6$, CO or CS; or a pharmaceutically acceptable salt thereof.

13. The (−) enantiomer of the compound of claim 12.
14. The (+) enantiomer of the compound of claim 12.
15. The compound of claim 12 having the structure:

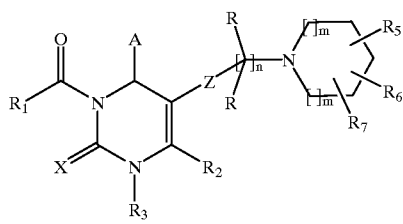

16. The compound of claim 15 having the structure:

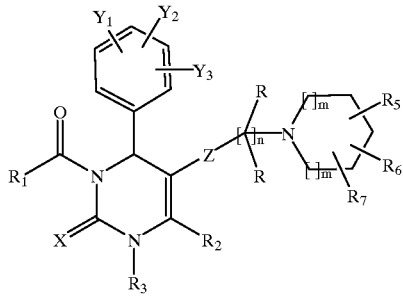

17. The compound of claim 16 having the structure:

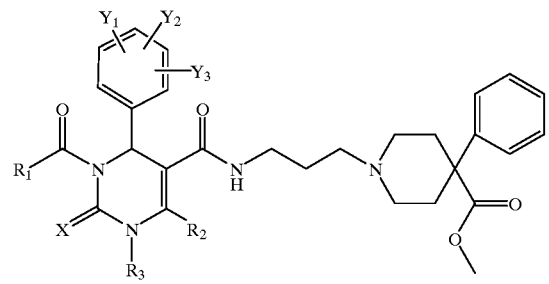

18. The compound of claim 16 having the structure:

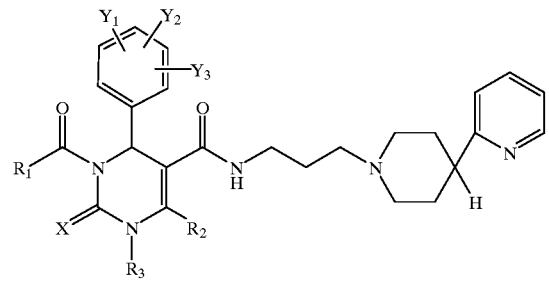

19. A pharmaceutical composition comprising a therapeutically effective amount of the compound of claims 1, 12, and a pharmaceutically acceptable carrier.
20. The pharmaceutical composition of claim 19 wherein the therapeutically effective amount is an amount from about 0.01 mg to about 500 mg.
21. The pharmaceutical composition of claim 20 wherein the therapeutically effective amount is from about 0.1 mg to about 60 mg.
22. The pharmaceutical composition of claim 21 wherein the therapeutically effective amount is from about 1 mg to about 20 mg.
23. The pharmaceutical composition of claim 19, wherein the carrier is a liquid and the composition is a solution.
24. The pharmaceutical composition of claim 19, wherein the carrier is a solid and the composition is a tablet.
25. The pharmaceutical composition of claim 19, wherein the carrier is a gel and the composition is a suppository.
26. A pharmaceutical composition comprising a therapeutically effective amount of the compound of claims 1 or 12, in combination with a therapeutically effective amount of finasteride and a pharmaceutically acceptable carrier.
27. The pharmaceutical composition of claim 26 wherein the therapeutically effective amount of the compound of claims 1 or 12 is an amount from about 0.01 mg to about 500 mg and the therapeutically effective amount of the finasteride is about 5 mg.
28. The pharmaceutical composition of claim 27 wherein the therapeutically effective amount of the compound of claims 1 or 12 is an amount from about 0.1 mg to about 60 mg and the therapeutically effective amount of finasteride is about 5 mg.
29. The pharmaceutical composition of claim 28 wherein the therapeutically effective amount of the compound of claims 1 or 12 is an amount from about 1 mg to about 20 mg and the therapeutically effective amount of finasteride is about 5 mg.

* * * * *

UNITED STATES PATENT AND TRADEMARK OFFICE
CERTIFICATE OF CORRECTION

PATENT NO.   : 5,942,517
DATED        : August 24, 1999
INVENTOR(S)  : Dhanapalan Nagarathnam et al.

It is certified that error appears in the above-identified patent and that said Letters Patent is hereby corrected as shown below:

Column 2,
Line 22, "alc" should read -- $\alpha_{1c}$ --

Column 5,
Line 7, "$C_3$-$C_7$" should read -- $C_1$-$C_7$ --
Line 7, "monof luoroalkyl" should read -- monofluoroalkyl --

Column 8,
Structure should be:

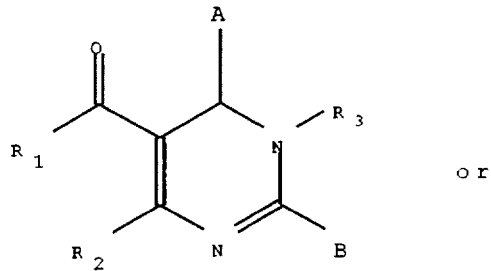 or 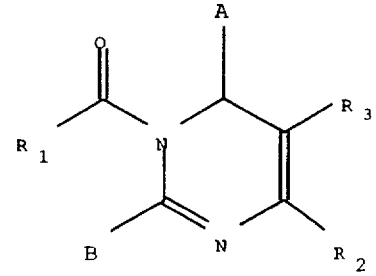

Column 11,
Line 62, "hydrof luoric acid" should read -- hydrofluoric acid --

Column 24,
Line 55, "33.6w" should read -- 33.6% --

Column 31,
Line 39, "5- (2-cyanoethoxycarbonyl) -4-ethyl -i,6-dihydro-2-methoxy-6- (4-nitrophenyl) pyrimidine" should read -- 5- (2-cyanoethoxycarbonyl) - 4-ethyl-1, 6-dihydro-2-methoxy-6- (4-nitrophenyl) pyrimidine --

UNITED STATES PATENT AND TRADEMARK OFFICE
CERTIFICATE OF CORRECTION

PATENT NO. : 5,942,517
DATED : August 24, 1999
INVENTOR(S) : Dhanapalan Nagarathnam et al.

It is certified that error appears in the above-identified patent and that said Letters Patent is hereby corrected as shown below:

Column 32,
Line 63, "(+) -5-Carboxamido-6-(3,4-difluorophenyl) -4-ethyl -1-{N- [3-(4-methoxycarbonyl-4-phenylpiperidin-1-propyl|} carboxamido-2-oxo-1,2,3, 6-tetrhydopyrimidine" should read -- (+) -5-Carboxamido-6- (3,4-difluorophenyl) -4-ethyl-1-{N-[3-(4-methoxycarbonyl-4-phenylpiperidin-1-yl)propxyl]} carboxamido-2-oxo-1,2,3,6-tetrhydropyrimidine --

Column 36,
Line 67, "100w" should read -- 100% --

Column 38,
Line 16, "6-3, benzofuranzan-5-yl) -5-methoxycarbonyl-4-methyl 2-oxo-1-{N-[4-(2-pyridyl)-piperidin-1-]propyl} carboxamido-1,2,3,6-tetrahydopyrimidine dihydrochloride" should read -- 6-3,4 benzofurazan-5-yl) -5-methoxycarbonyl-4-methyl 2-oxo-1-{N- [4- (2-pyridyl) -piperidin-1 yl-] propyl} carboxamido-1,2,3,6-tetrahydopyrimidine dihydrochloride --

The following structure should be inserted as the last two structures of claim 1:

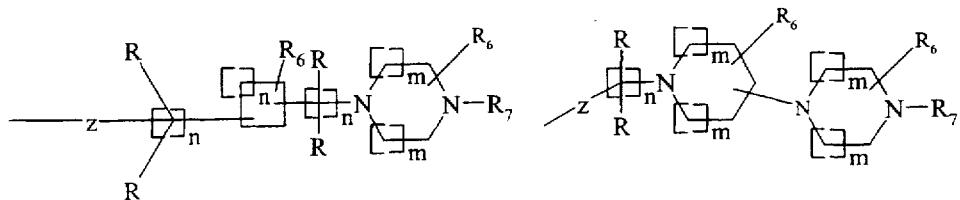

UNITED STATES PATENT AND TRADEMARK OFFICE
CERTIFICATE OF CORRECTION

PATENT NO. : 5,942,517
DATED : August 24, 1999
INVENTOR(S) : Dhanapalan Nagarathnam et al.

It is certified that error appears in the above-identified patent and that said Letters Patent is hereby corrected as shown below:

Claim 7,
The structure should be:

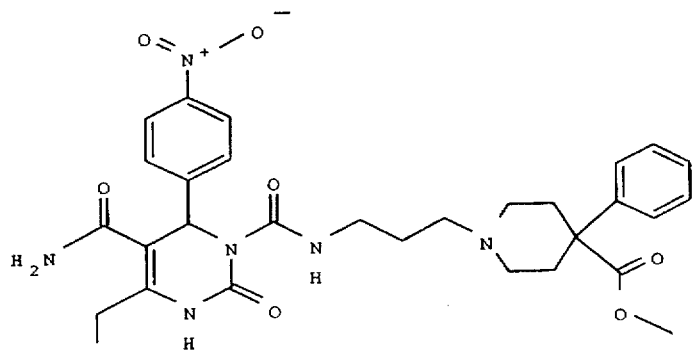

Column 65,
Line 66, "$C_1$-$C_{20}$" should read -- $C_1$-$C_{10}$ --

Signed and Sealed this

Twelfth Day of February, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO. : 5,942,517
DATED : August 24, 1999
INVENTOR(S) : Dhanapalan Nagarathnam et al.

It is certified that error appears in the above-identified patent and that said Letters Patent is hereby corrected as shown below:

Column 2,
Line 22, "alc" should read -- $\alpha_{1c}$ --

Column 5,
Line 7, "$C_3$-$C_7$" should read -- $C_1$-$C_7$ --
Line 7, "monof luoroalkyl" should read -- monofluoroalkyl --

Column 8,
Structure should be:

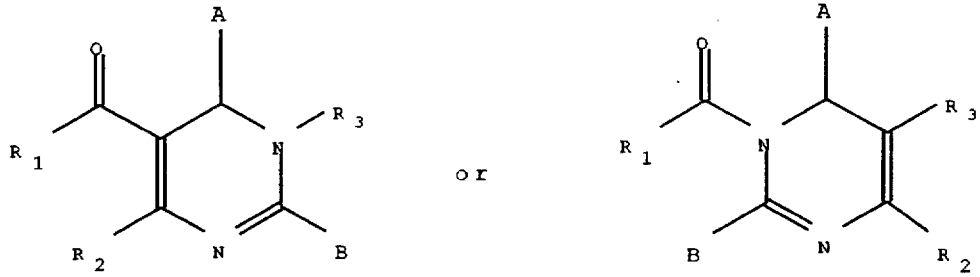

Column 11,
Line 62, "hydrof luoric acid" should read -- hydrofluoric acid --

Column 24,
Line 55, "33.6w" should read -- 33.6% --

Column 31,
Line 39, "5- (2-cyanoethoxycarbonyl) -4-ethyl -i,6-dihydro-2-methoxy-6- (4-nitrophenyl) pyrimidine" should read -- 5- (2-cyanoethoxycarbonyl) - 4-ethyl-1, 6-dihydro-2-methoxy-6- (4-nitrophenyl) pyrimidine --

UNITED STATES PATENT AND TRADEMARK OFFICE
CERTIFICATE OF CORRECTION

PATENT NO.    : 5,942,517
DATED         : August 24, 1999
INVENTOR(S)   : Dhanapalan Nagarathnam et al.

It is certified that error appears in the above-identified patent and that said Letters Patent is hereby corrected as shown below:

Column 32,
Line 63, "(+) -5-Carboxamido-6-(3,4-difluorophenyl) -4-ethyl -1-{N- |3-(4-methoxycarbonyl-4-phenylpiperidin-1-propyl|} carboxamido-2-oxo-1,2,3, 6-tetrhydopyrimidine" should read -- (+) -5-Carboxamido-6- (3,4-difluorophenyl) -4-ethyl-1-{N-[3-(4-methoxycarbonyl-4-phenylpiperidin-1-yl)propyl]} carboxamido-2-oxo-1,2,3,6-tetrhydropyrimidine --

Column 36,
Line 67, "100w" should read -- 100% --

Column 38,
Line 16, "6-3, benzofuranzan-5-yl) -5-methoxycarbonyl-4-methyl 2-oxo-1-{N-[4-(2-pyridyl)-piperidin-1-]propyl} carboxamido-1,2,3,6-tetrahydopyrimidine dihydrochloride" should read -- 6-3,4 benzofurazan-5-yl) -5-methoxycarbonyl-4-methyl 2-oxo-1-{N- [4- (2-pyridyl) -piperidin-1 yl-] propyl} carboxamido-1,2,3,6-tetrahydopyrimidine dihydrochloride --

The following structure should be inserted as the last two structures of claim 1:

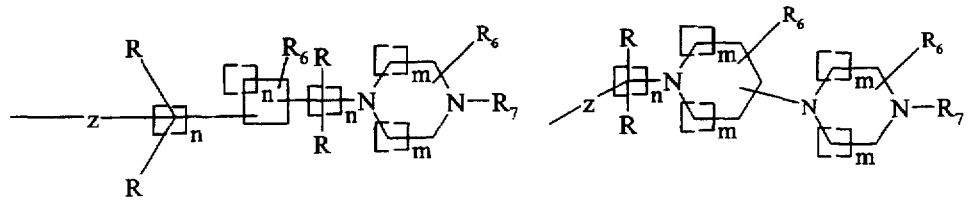

UNITED STATES PATENT AND TRADEMARK OFFICE
CERTIFICATE OF CORRECTION

PATENT NO. : 5,942,517
DATED : August 24, 1999
INVENTOR(S) : Dhanapalan Nagarathnam et al.

It is certified that error appears in the above-identified patent and that said Letters Patent is hereby corrected as shown below:

Claim 7,
The structure should be:

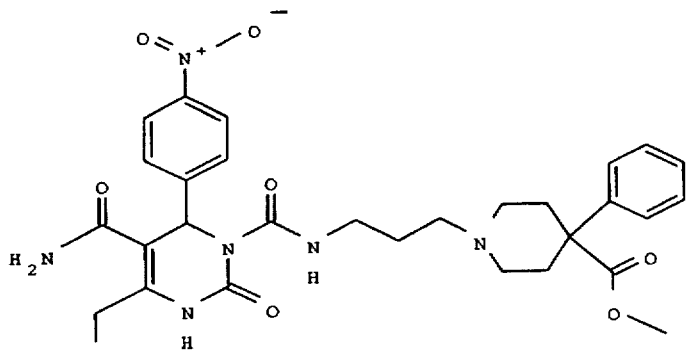

Column 65,
Line 66, "$C_1$-$C_{20}$" should read -- $C_1$-$C_{10}$ --

This certificate supercedes Certificate of Correction issued February 12, 2002.

Signed and Sealed this

Sixteenth Day of April, 2002

Attest:

*Attesting Officer*

JAMES E. ROGAN
*Director of the United States Patent and Trademark Office*